US012403141B2

(12) United States Patent
Anderson et al.

(10) Patent No.: US 12,403,141 B2
(45) Date of Patent: Sep. 2, 2025

(54) DEUTERATED MK2 PATHWAY INHIBITORS AND METHODS OF USING THE SAME

(71) Applicant: ACLARIS THERAPEUTICS, INC., Wayne, PA (US)

(72) Inventors: David Randolph Anderson, Salem, CT (US); Gary Anthony Decrescenzo, Parkville, MO (US)

(73) Assignee: Aclaris Therapeutics, Inc., Wayne, PA (US)

( * ) Notice: Subject to any disclaimer, the term of this patent is extended or adjusted under 35 U.S.C. 154(b) by 855 days.

(21) Appl. No.: 17/630,414

(22) PCT Filed: Jul. 31, 2020

(86) PCT No.: PCT/US2020/044558
§ 371 (c)(1),
(2) Date: Jan. 26, 2022

(87) PCT Pub. No.: WO2021/022186
PCT Pub. Date: Feb. 4, 2021

(65) Prior Publication Data
US 2022/0288070 A1    Sep. 15, 2022

Related U.S. Application Data

(60) Provisional application No. 62/881,026, filed on Jul. 31, 2019.

(51) Int. Cl.
*A61K 31/506* (2006.01)
*A61P 35/00* (2006.01)
*A61P 37/02* (2006.01)
*C07D 401/14* (2006.01)

(52) U.S. Cl.
CPC .......... *A61K 31/506* (2013.01); *A61P 35/00* (2018.01); *A61P 37/02* (2018.01); *C07D 401/14* (2013.01)

(58) Field of Classification Search
None
See application file for complete search history.

(56) References Cited

U.S. PATENT DOCUMENTS

| 9,115,089 B2 * | 8/2015 | Hockerman ............ A61P 17/02 |
| 2012/0252830 A1 | 10/2012 | Coppola et al. |
| 2014/0364442 A1 | 12/2014 | Hockerman et al. |
| 2015/0352092 A1 | 12/2015 | Hockerman et al. |
| 2019/0169127 A1 | 6/2019 | Lin et al. |
| 2023/0087078 A1 | 3/2023 | Lin et al. |

OTHER PUBLICATIONS

Dyck et al. Effects of deuterium substitution on the catabolismof beta-phenylethylamine: an in vivo study. J Neurochem. 1986, 46(2), 399-404 (Year: 1986).*
"Isotopic Enrichment" US Nuclear Regulatory Commission. https://www.nrc.gov/reading-rm/basic-ref/glossary/isotopic-enrichment.html (Year: 2021).*
Levernier, E. et al. Easy-to-Implement Hydrogen Isotope Exchange for the Labeling of N-Heterocycles, Alkylkamines, Benzylic Scaffolds, and Pharmaceuticals. JACS Au 2022, 2, 4, 801-808 (Year: 2022).*
Libretext. "Deuterated Compounds" https://chem.libretexts.org/@go/page/34054 (Year: 2024).*
European Search Report and Written Opinion for EP 20847487.4 dated Jun. 16, 2023.
Haller et al. An updated patent review of p38 MAP kinase inhibitors (2014-2019), Apr. 20, 2020, Expert Opinion on Therapeutic Patents 30(6):453-466.
Kaur et al. "Deuteration as a Tool for Optimization of Metabolic Stability and Toxicity of Drugs" Mar. 27, 2017, Global Journal Pharmacy & Pharmacology 1(4):1-11—ID 555566.
Shao et al. "Synthesis of d3-Poziotinib Hydrochloride and Stability of Liver Microsoes in vitro" Jul. 15, 2019, Journal of Yantai University 32(03):220-225 (with English abstract).
McMahon "VEGF Receptor Signaling in Tumor Angiogenesis" 2000, the Oncologist 5(supp 1):3-10.
Pinedo et al. "Translational Research: The Role of VEGF in Tumor Angiogenesis" 2000, the Oncologist 5(supp 1):1-2.
International Search Report and Written Opinion for corresponding Application No. PCT/US2020/044558 (mailed Oct. 28, 2020).

* cited by examiner (Continued)

*Primary Examiner* — Clinton A Brooks
*Assistant Examiner* — Nicola Maria Bauer
(74) *Attorney, Agent, or Firm* — DLA Piper LLP

(57) ABSTRACT

The present disclosure provides deuterated pyridinone-pyridinyl compounds and compositions useful in the treatment of p38 MAP Kinase mediated having the structures of Formula (I); wherein the A, B, and R groups are as defined in the detailed description. Methods of inhibition of p38 MAP Kinase activity in a human or animal subject are also provided.

7 Claims, 10 Drawing Sheets

Plasma time-course data for Example 1-D$_2$ and Example 1-H$_2$ at 0.1 mpk IV

Plasma time-course data for Example 1-D$_2$ and Example 1-H$_2$ at 0.3 mpk IV

Plasma time-course data for Example 1-D$_2$, Example 1-H$_2$ and Example 13-D$_6$ at 1 mpk IV Plasma time-course data for Example 1-D$_2$, Example 1-H$_2$ and Example 13-D$_6$ at 2 mpk PO Plasma time-course data for Example 3-D$_2$ and Example 3-H$_2$ at 0.1 mpk IV Plasma time-course data for Example 3-D$_2$ and Example 3-H$_2$ at 1 mpk IV Plasma time-course data for Example 3-D$_2$ and Example 3-H$_2$ at 1 mpk IV Plasma time-course data for Example 5-D$_2$ and Example 5-H$_2$ at 0.1 mpk IV Plasma time-course data for Example 5-$D_2$ and Example 5-$H_2$ at 1 mpk IV Plasma time-course data for Example 7-$D_2$ and Example 7-$H_2$ at 0.1 mpk IV Plasma time-course data for Example 7-$D_2$ and Example 7-$H_2$ at 1 mpk IV Plasma time-course data for Example 9-$D_2$ and Example 9-$H_2$ at 0.1 mpk IV Plasma time-course data for Example 9-D₂ and Example 9-H₂ at 1 mpk IV Plasma time-course data for Example 11-D₂ and Example 11-H₂ at 0.1 mpk IV Plasma time-course data for Example 11-D$_2$ and Example 11-H$_2$ at 1 mpk IV

Proposed metabolic pathways for Example 1-D$_2$ in rat, dog, minipig, monkey, and human hepatocytes

Proposed metabolic pathways for Example 1-H$_2$ in rat, dog, minipig, monkey, and human hepatocytes

DEUTERATED MK2 PATHWAY INHIBITORS AND METHODS OF USING THE SAME

CROSS-REFERENCE TO RELATED APPLICATIONS

This application claims the benefit of U.S. Provisional Application No. 62/881,026 filed Jul. 31, 2019, which is hereby incorporated by reference in its entirety for all purposes.

SUMMARY

Embodiments herein are directed to compounds having the structure of Formula (I), or a derivative thereof, where the A, B, and R groups are defined herein:

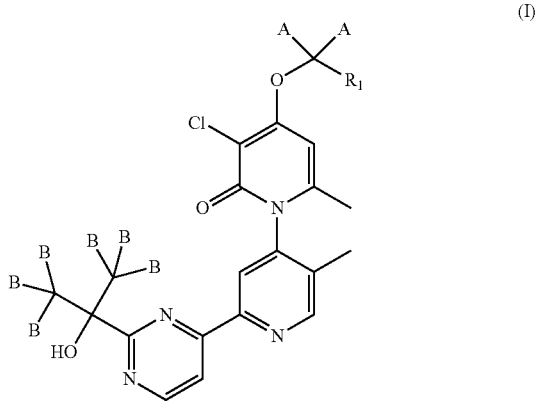

In various embodiments, provided are pharmaceutical compositions comprising a compound as described in the embodiments herein and one or more pharmaceutically acceptable excipients and/or additional pharmaceutically active compounds.

In other embodiments, there is provided methods for treating a condition comprising administering to a subject a therapeutically effective amount of a compound as described in the embodiments herein, alone or in combination with other pharmaceutically active compounds, wherein the condition to be treated includes, but is not limited to, autoimmune disorders, chronic inflammatory disorders, acute inflammatory disorders, auto-inflammatory disorders, pain, atherosclerosis, diabetes, fibrotic diseases, metabolic disorders, cancer, neoplasia, leukemia, lymphoma, rheumatoid arthritis, and idiopathic pulmonary fibrosis.

DETAILED DESCRIPTION

Figure 1:
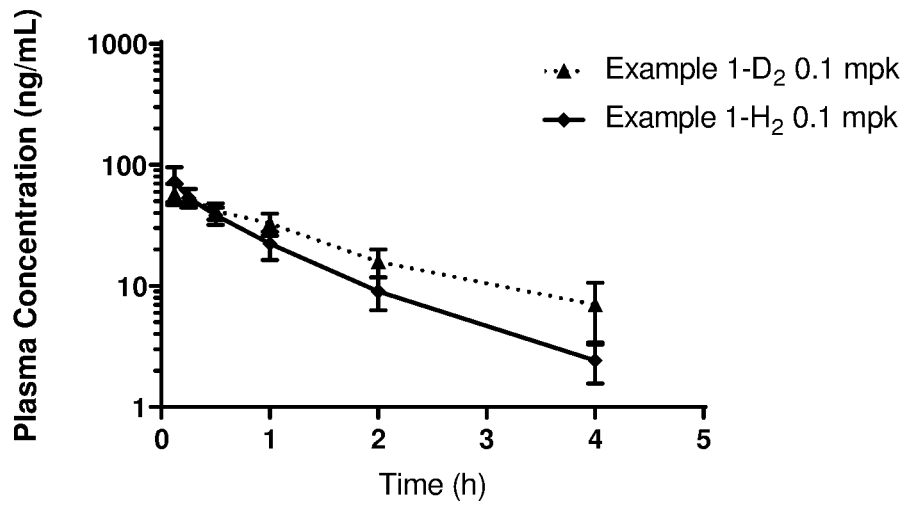
FIG. 1 shows the Plasma time-course data for Example 1-$D_2$ and Example 1-$H_2$ at 0.1 mg/kg (mpk) intravenous (IV).

Before the present compositions and methods are described, it is to be understood that this invention is not limited to the particular processes, compositions, or methodologies described, as these may vary. It is also to be understood that the terminology used in the description is for the purpose of describing the particular versions or embodiments only and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

Definitions

It must also be noted that as used herein and in the appended claims, the singular forms "a," "an," and "the" include plural reference unless the context clearly dictates otherwise. Thus, for example, reference to a "p38 MAP Kinase inhibitor" is a reference to one or more p38 MAP Kinase inhibitor and equivalents thereof known to those skilled in the art, and so forth.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean plus or minus 10% of the numerical value of the number with which it is being used. Therefore, about 50% means in the range of 45%-55%.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the pharmaceutical composition, composition or the method includes only the elements, steps, or ingredients specifically recited in the particular claimed embodiment or claim.

As used herein, the term "consisting essentially of" or "consists essentially of" means that the pharmaceutical composition, or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the composition or method that treats the specified condition (e.g., nutrient depletion) is the specifically recited therapeutic(s) in the particular embodiment or claim.

As used herein, two embodiments are "mutually exclusive" when one is defined to be something which is different from the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

As used herein, the term "a derivative thereof" refers to a salt thereof, a pharmaceutically acceptable salt thereof, an ester thereof, a free acid form thereof, a free base form thereof, a solvate thereof, a co-crystal thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, or a combination thereof.

As used herein, the term "pharmaceutically acceptable salt" refers to a salt prepared from a base or acid which is acceptable for administration to a patient, such as a mammal. The term "pharmaceutically acceptable salts" embraces salts commonly used to form alkali metal salts and to form addition salts of free acids or free bases. The nature of the salt is not critical, provided that it is pharmaceutically-acceptable. Such salts can be derived from pharmaceutically-acceptable inorganic or organic bases and from pharmaceutically-acceptable inorganic or organic acids.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH₃ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein.

Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH₂—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—).

Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)NH(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH$—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term, "compound," as used herein is meant to include all stereoisomers, geometric isomers, and tautomers of the structures depicted.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "halocycloalkyl" as used herein, alone or in combination, refers to a cycloalkyl radical having the meaning as defined above wherein one or more hydrogens are replaced with a halogen. Specifically embraced are monohalocycloalkyl, dihalocycloalkyl and polyhalochaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluorocyclopropyl, difluorocyclopropyl, fluorocyclobutyl, chlorocyclobutyl, and chlorocyclopentyl.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower alkyl," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between four and six ring members, of which between one and four may be heteroatoms chosen from N, O, and S (i.e., $C_3$-$C_6$ heterocycloalkyl). Examples of lower heterocycloalkyls include oxetane, azetidiene, pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

As used herein, an "N-oxide" is formed from the tertiary basic amines or imines present in the molecule, using a convenient oxidizing agent.

The terms "oxy" or "oxa," as used herein, alone or in combination, refer to —O—

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

As used herein, the term "atropisomeric purity" and "atropisomeric excess" (ae) are interchangeable and may refer to the measurement of the absolute difference between the mole fraction of each atropisomer and is most often expressed as a percentage. % atropisomeric excess may be determined by the formula:

$$\% \, ae = |A-B| \times 100$$

Where A and B are the respective mole fractions of the atropisomers in a mixture such that A+B=1. A racemic mixture has an atropisomeric excess of 0%, while a single completely pure atropisomer has an atropisomeric excess of 100%. As an example, a sample with 70% of P isomer and 30% of M will have an atropisomeric excess of 40%. This can also be thought of as a mixture of 40% pure P with 60% of a racemic mixture (which contributes 30% P and 30% M to the overall composition).

The term "substantially free" as used herein, alone or in combination, refers to a compound which is free from all other compounds within the limits of detection as measured by any means including nuclear magnetic resonance (NMR), gas chromatography/mass spectroscopy (GC/MS), or liquid chromatography/mass spectroscopy (LC/MS).

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl—C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written.

For example, an unsymmetrical group such as —C(O)N(R)— may be attached to the parent moiety at either the carbon or the nitrogen.

Stereogenic centers exist in the compounds disclosed herein. These centers are designated by the symbols "R" or "S," depending on the configuration of substituents around the stereogenic center. It should be understood that the invention encompasses all stereoisomeric forms, including diastereomeric, enantiomeric, and epimeric forms, as well as d-isomers and 1-isomers, and mixtures thereof. Individual stereoisomers of compounds can be prepared synthetically from commercially available starting materials which contain defined stereochemical configurations or by separation of mixtures of stereoisomeric products by conversion to a mixture of diastereomers followed by separation or recrystallization, chromatographic techniques, direct separation of stereoisomers by chiral chromatographic columns, or any other appropriate method known in the art. Starting compounds of particular configurations are either commercially available or can be made and resolved by techniques known in the art. Additionally, the compounds disclosed herein may exist as geometric isomers. The present invention includes all cis, trans, syn, anti, endo, exo, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients, or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"p38 MAP Kinase inhibitor" is used herein to refer to a compound that exhibits an $IC_{50}$ with respect to p38 MAP Kinase activity of no more than about 100 μM and more typically not more than about 50 μM, as measured in the p38 MAP Kinase enzyme assays described generally herein. In some embodiments, the compounds will exhibit an $IC_{50}$ with respect to p38 MAP Kinase of about 1 μM to about 50 μM. $IC_{50}$ is that concentration of inhibitor which reduces the activity of an enzyme (e.g., p38 MAP Kinase) to half-maximal level. Certain compounds disclosed herein have been discovered to exhibit inhibition against p38 MAP Kinase. In some embodiments, the compounds will exhibit an $IC_{50}$ with respect to p38 MAP Kinase of no more than about 300 nM. In some embodiments, the compounds will exhibit an $IC_{50}$ with respect to p38 MAP Kinase of no more than about 1 nM. In certain embodiments, compounds will exhibit an $IC_{50}$ with respect to p38 MAP Kinase of no more than about 50 μM; in further embodiments, compounds will exhibit an $IC_{50}$ with respect to p38 MAP Kinase of no more than about 10 μM; in yet further embodiments, compounds will exhibit an $IC_{50}$ with respect to p38 MAP Kinase of not more than about 5 μM; in yet further embodiments, compounds will exhibit an $IC_{50}$ with respect to p38 MAP Kinase of not more than about 1 μM, as measured in the p38 MAP Kinase assay described herein.

The phrase "therapeutically effective" is intended to qualify the amount of active ingredients used in the treatment of a disease or disorder or on the effecting of a clinical endpoint.

As used herein, the term "therapeutic" or "therapeutic agent" or "pharmaceutically active agent" means an agent utilized to treat, combat, ameliorate, prevent or improve an unwanted condition or disease of a patient. In part, embodiments of the present invention are directed to the treatment of p38 MAP Kinase mediated diseases.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The term "therapeutically acceptable" refers to those compounds, or a derivative thereof, which are suitable for use in contact with the tissues of patients without undue toxicity, irritation, and allergic response, are commensurate with a reasonable benefit/risk ratio, and are effective for their intended use.

The terms "treat," "treated," "treating", or "treatment" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total, whether induction of or maintenance of), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease and prolonging disease-free survival as compared to disease-free survival if not receiving treatment and prolonging disease-free survival as compared to disease-free survival if not receiving treatment.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a compound of embodiments herein, can include, but is not limited to, providing the compound into or onto the target tissue; providing the compound systemically to a patient by, e.g., intravenous injection whereby the therapeutic reaches the target tissue; providing the compound in the form of the encoding sequence thereof to the target tissue (e.g., by so-called gene-therapy techniques). "Administering" a composition may be accomplished by injection, topically, orally, or by any of these methods in combination with other known techniques.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The terms "excipient" and "pharmaceutically acceptable excipient" as used herein are intended to be generally synonymous, and is used interchangeably with, the terms "carrier," "pharmaceutically acceptable carrier," "diluent," "pharmaceutically acceptable diluent."

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Embodiments of the present invention are directed to compounds and pharmaceutical compositions comprising such compounds, which have been found to inhibit p38 MAP Kinase, together with methods of synthesizing and using the compounds including, without limitation, methods for the treatment of p38 MAP Kinase mediated diseases in a patient by administering the compounds. In some embodiments the compounds and pharmaceutical compositions are administered topically.

LIST OF ABBREVIATIONS

ACN acetonitrile
Boc tert-butyloxycarbonyl
Bu butyl
Bpy 2,2'-bipyridine
DCA dichloroacetic acid
DCI dicyclohexylcarbodiimide
DCM dichloromethane or methylenechloride
DIPEA diisopropylethylamine
DMA dimethylacetamide
DMAP 4-dimethylaminopyridine or N,N-dimethylaminopyridine
DME 1,2-dimethoxyethane
DMF N,N-dimethylformamide
DMSO dimethylsulfoxide
$CuBr_2$ copper(II)bromide EDAC N-(3-dimethylaminopropyl)-N'-ethylcarbodiimide hydrochloride
eq. equivalents
Et ethyl
EtOAC ethyl acetate
EtOH ethanol
HPLC high pressure liquid chromatography
h hour(s)
IPA isopropyl alcohol
$K_2CO_3$ potassium carbonate
KOtBu potassium tert-butoxide
LAH lithium aluminum hydride
LC/MS liquid chromatography mass spectrometry
LC/MS/MS liquid chromatography tandem mass spectrometry
mCPBA m-chloroperbenzoic acid
Me methyl
MeCN acetonitrile
MeOH methanol
$MgSO_4$ magnesium sulfate
mL milliliter
mmol millimole
NaH sodium hydride
$NaN(TMS)_2$ sodium bis(trimethylsilyl)amide
NCS N-chloro succinimide
NMR nuclear magnetic resonance
NMP N-methylpyrrolidone
Pd/C palladium on carbon
Ph phenyl
PPA polyphosphoric acid
TEA triethylamine
TFA trifluoroacetic acid
THF tetrahydrofuran
TOSMIC toluenesulfonylmethyl isocyanide
TSA p-toluenesulfonic acid.

Compounds

Embodiments herein are directed to compounds and pharmaceutical compositions comprising such compounds, which have been found to inhibit p38 MAP Kinase, together with methods of synthesizing and using the compounds. Some embodiments include methods for the treatment of diseases in a patient by administering the compounds of embodiments herein.

Certain compounds disclosed herein may possess useful p38 MAP Kinase inhibiting activity and may be used in the treatment or prophylaxis of a disease or condition in which p38 MAP Kinase plays an active role. Thus, embodiments are also directed to pharmaceutical compositions comprising one or more compounds disclosed herein together with a pharmaceutically acceptable carrier, as well as methods of making and using the compounds and compositions. Certain embodiments are directed to methods for inhibiting p38 MAP Kinase. Other embodiments are directed to methods for treating a p38 MAP Kinase mediated disorder in a patient in need of such treatment, comprising administering to said patient a therapeutically effective amount of a compound or composition according to the present invention. Also provided is the use of certain compounds disclosed herein in the manufacture of a medicament for the treatment of a disease or condition ameliorated by the inhibition of p38 MAP Kinase.

Also provided are embodiments wherein any embodiment herein may be combined with any one or more of the other embodiments, unless otherwise stated and provided the combination is not mutually exclusive.

Also provided is a compound chosen from the Examples disclosed herein. The compounds of embodiments herein may also refer to a derivative thereof, or a combination of the foregoing of the compounds of embodiments herein.

Compounds described herein may contain one or more stereogenic centers and may thus exist as stereoisomers. Embodiments herein includes all such possible stereoisomers as substantially pure resolved stereoisomers, racemic mixtures thereof, as well as mixtures of diastereomers. In some embodiments, the formulas are shown without a definitive stereochemistry at certain positions. In other embodiments, the compounds are isolated as single stereoisomers, but the absolute configurations of the stereogenic centers are unknown or only the relative stereochemical configuration (i.e., cis or trans isomerism) is known. In such embodiments, the formulas are shown with provisionally assigned absolute assignments to denote that they are single stereoisomers and relative stereochemical configuration is likewise described. Embodiments herein include all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any stereoisomer of a compound of the general formula may be obtained by stereospecific or stereoselective synthesis using optically pure or enantioenriched starting materials or reagents of known configuration. The scope of embodiments herein as described and claimed encompasses the racemic forms of the compounds as well as the individual enantiomers, diastereomers, stereoisomers and stereoisomer-enriched mixtures.

Conventional techniques for the preparation/isolation of individual enantiomers include chiral synthesis from a suitable enantioenriched or optically pure precursors or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of embodiments herein (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g., "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. This phenomenon creates stereoisomers which display axial chirality.

Oki (Oki, M; Topics in Stereochemistry 1983, 1) defined atropisomers as conformers that interconvert with a half-life of more than 1000 seconds at a given temperature. The scope of embodiments herein as described and claimed encompasses the racemic forms of the compounds as well as the individual atropisomers (an atropisomer "substantially free" of its corresponding enantiomer) and stereoisomer-enriched mixtures, i.e. mixtures of atropisomers.

Separation of atropisomers is possibly by chiral resolution methods such as selective crystallization. In an atropoenantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

The following scheme illustrates "atropisomerism" with reference to specific pyridinone-pyridine compounds of the invention:

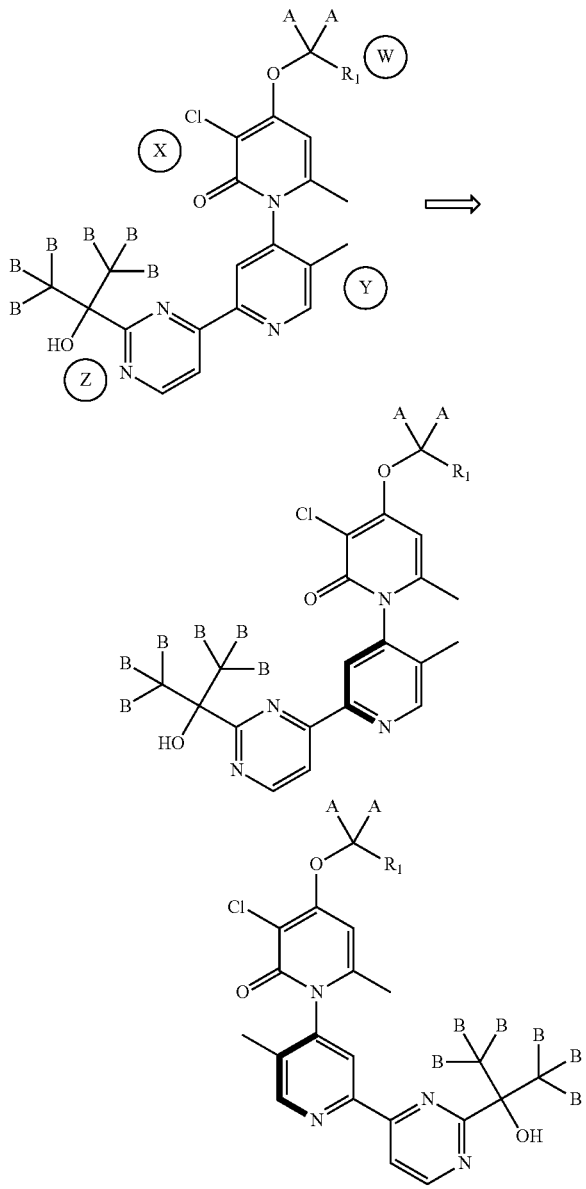

The bond between the X and Y rings of the compounds of the present invention is hindered and does not allow for facile rotation. The steric strain barrier to rotation is sufficiently high such that individual conformers can be isolated. The compounds of the invention do exist as atropisomers, i.e., chiral rotational isomers. The invention encompasses racemates, resolved atropisomers, and mixtures thereof. Atropisomers may be separated via supercritical fluid chromatography using a mobile phase of carbon dioxide and ethanol/methanol.

Atropisomers are generally stable but can often be equilibrated thermally. Atropisomers will have the same but opposite optical rotation. Each atropisomers may have different properties when bound to an enzyme or receptor with one isomer often being more potent than the other. Atropisomers are frequently used as pharmaceutical agents. Known examples include Vancomycin and derivatives.

The configuration of atropisomers can be described using the nomenclature (M)- and (P)— to describe the relative position of substituents as described in Bringmann, G. et. al., Angew. Chem. Int. Ed. 2005, 44, 5384 and references cited therein. Structures are designated as drawn but it is understood that either (P)— or (M)-isomers may be desirable.

Suitable pharmaceutically acceptable acid addition salts of the compounds of embodiments herein may be prepared from an inorganic acid or an organic acid. All of these salts may be prepared by conventional means from the corresponding compound of embodiments herein by treating, for example, the compound with the appropriate acid or base.

Pharmaceutically acceptable acids include both inorganic acids, for example hydrochloric, hydrobromic, hydroiodic, nitric, carbonic, sulfuric, phosphoric and diphosphoric acid; and organic acids, for example formic, acetic, trifluoroacetic, propionic, succinic, glycolic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, galacturonic, citric, fumaric, gluconic, glutamic, lactic, maleic, malic, mandelic, mucic, ascorbic, oxalic, pantothenic, succinic, tartaric, benzoic, acetic, xinafoic (1-hydroxy-2-naphthoic acid), napadisilic (1,5-naphthalenedisulfonic acid) and the like.

Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, chloroprocaine, diethanolamine, N-methylglucamine, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to embodiments herein are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

The compounds of embodiments herein may exist in both unsolvated and solvated forms. The term solvate is used herein to describe a molecular complex comprising a compound of embodiments herein and an amount of one or more pharmaceutically acceptable solvent molecules. The term hydrate is employed when said solvent is water. Examples of solvate forms include, but are not limited to, compounds of embodiments herein in association with water, acetone, dichloromethane, 2-propanol, ethanol, methanol, dimethylsulfoxide (DMSO), ethyl acetate, acetic acid, ethanolamine, or mixtures thereof. It is specifically contemplated that in embodiments herein one solvent molecule can be associated with one molecule of the compounds of embodiments herein, such as a hydrate.

Furthermore, it is specifically contemplated that in embodiments herein, more than one solvent molecule may be associated with one molecule of the compounds of embodiments herein, such as a dihydrate. Additionally, it is specifically contemplated that in embodiments herein less than one solvent molecule may be associated with one molecule of the compounds of embodiments herein, such as a hemihydrate. Furthermore, solvates of embodiments herein are contemplated as solvates of compounds of embodiments herein that retain the biological effectiveness of the non-solvate form of the compounds.

At positions of chemical structures that are labeled as "H" or where hydrogen atoms are unlabeled, the compound is assumed to have a natural abundance of deuterium at that position. At positions of chemical structures that are labeled with "D", the compound has a greater than natural abundance of deuterium at that position.

The term "isotopic enrichment" or "isotopic enrichment factor" describes to the extent of replacement of hydrogen with deuterium compared to the naturally occurring amount of deuterium in a sample. For example, a sample of a compound drawn as having 2 deuterium atoms and having and isotopic enrichment of 98% $d_2$ and 1.5% $d_1$ means that 98% of the sample contains 2 deuterium atoms at the specified positions, 1.5% of the sample contains one deuterium atom and one hydrogen atom at the specified position and 0.5% contains deuterium at natural abundance at the specified positions.

The isotopic enrichment factor can be determined using conventional analytical methods known to one of ordinary skilled in the art, including mass spectrometry (MS) and nuclear magnetic resonance (NMR).

Prodrugs of the compounds described herein are also within the scope of embodiments herein. Thus, certain derivatives of the compounds of embodiments herein, which derivatives may have little or no pharmacological activity themselves, when administered into or onto the body may be converted into compounds of embodiments herein having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with embodiments herein can, for example, be produced by replacing appropriate functionalities present in the compounds of embodiments herein with certain moieties known to those skilled in the art as 'promoieties' as described, for example, in Design of Prodrugs by H. Bundgaard (Elsevier, 1985).

In the case of compounds of embodiments herein that are solids, it is understood by those skilled in the art that the inventive compounds and salts may exist in different crystalline or polymorphic forms, or in an amorphous form, all of which are intended to be within the scope of embodiments herein.

The compounds disclosed herein can exist as and therefore include all stereoisomers, atropisomers, tautomers, conformational isomers and mixtures thereof in all proportions.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

In certain embodiments, compounds have a structure of Formula (I):

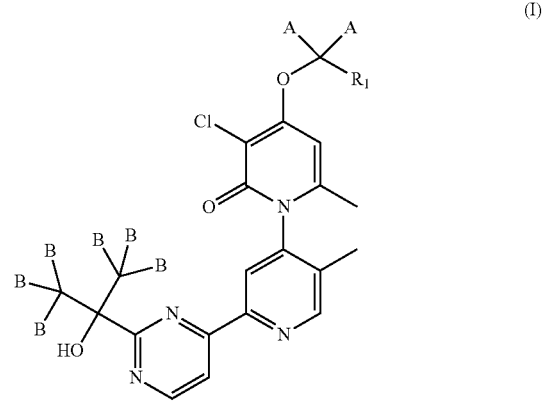

(I)

wherein:
A and B are independently selected from hydrogen and deuterium such that at least one instance of A or B is deuterium; and $R_1$ is selected from aryl and heteroaryl, where the aryl or heteroaryl is optionally substituted with one or more groups selected from: halogen, $C_{1-5}$alkyl, OH, O—$C_{1-5}$alkyl and CN, wherein each alkyl group may be optionally substituted with one or more halogens;

or a derivative thereof.

Embodiments of the invention are further illustrated by the following examples of compounds of Formula (I).

| Example Number | Structure | Compound Name |
|---|---|---|
| 1 | 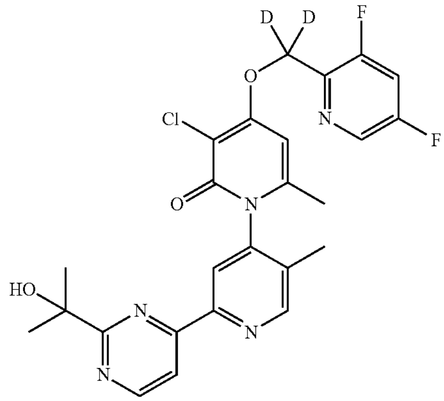 | 3-Chloro-4-((3,5-difluoropyridin-2-yl)methoxy-d$_2$)-2'-(2-(2-hydroxypropan-2-yl)pyrimidin-4-yl)-5',6-dimethyl-2H-[1,4'-bipyridin]-2-one, (atropisomer 1) |
| 2 | 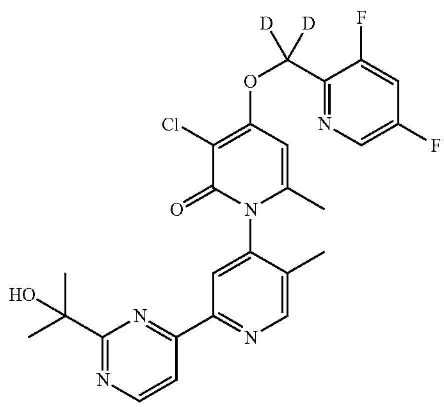 [SMILES: [2H]C([2H])(Oc1cc(C)n(-c2cc(-c3ccnc(C(C)(C)O)n3)ncc2C)c(=O)c1Cl)c1ncc(F)cc1F] | 3-Chloro-4-((3,5-difluoropyridin-2-yl)methoxy-d$_2$)-2'-(2-(2-hydroxypropan-2-yl)pyrimidin-4-yl)-5',6-dimethyl-2H-[1,4'-bipyridin]-2-one, (atropisomer 2) |
| 3 | 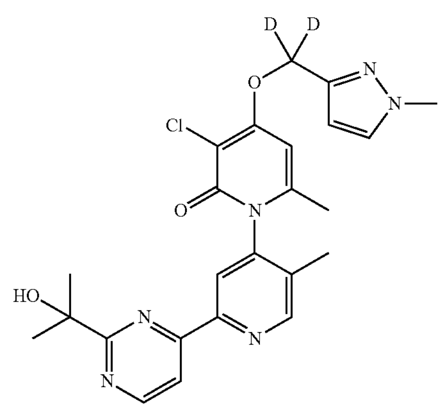 [SMILES: [2H]C([2H])(Oc1cc(C)n(-c2cc(-c3ccnc(C(C)(C)O)n3)ncc2C)c(=O)c1Cl)c1ccn(C)n1] | 3-Chloro-2'-(2-(2-hydroxypropan-2-yl)pyrimidin-4-yl)-5',6-dimethyl-4-((1-methyl-1H-pyrazol-3-yl)methoxy-d$_2$)-2H-[1,4'-bipyridin]-2-one, (atropisomer 1) |
| 4 | 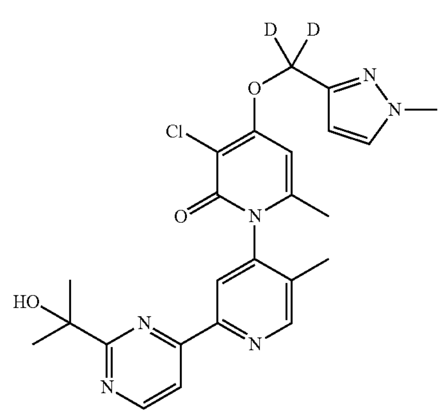 [SMILES: [2H]C([2H])(Oc1cc(C)n(-c2cc(-c3ccnc(C(C)(C)O)n3)ncc2C)c(=O)c1Cl)c1ccn(C)n1] | 3-Chloro-2'-(2-(2-hydroxypropan-2-yl)pyrimidin-4-yl)-5',6-dimethyl-4-((1-methyl-1H-pyrazol-3-yl)methoxy-d$_2$)-2H-[1,4'-bipyridin]-2-one, (atropisomer 2) |

-continued

| Example Number | Structure | Compound Name |
|---|---|---|
| 5 | 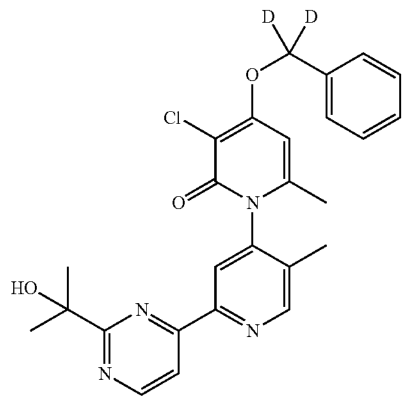 [SMILES: [2H]C([2H])(Oc1cc(C)n(-c2cc(-c3ccnc(C(C)(C)O)n3)ncc2C)c(=O)c1Cl)c1ccccc1] | 3-Chloro-2'-(2-(2-hydroxypropan-2-yl)pyrimidin-4-yl)-5',6-dimethyl-4-(phenylmethoxy-d$_2$)-2H-[1,4'-bipyridin]-2-one, (atropisomer 1) |
| 6 | 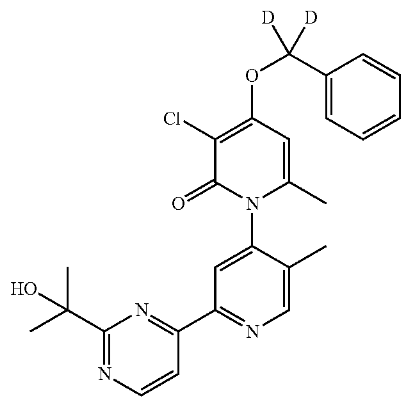 [SMILES: [2H]C([2H])(Oc1cc(C)n(-c2cc(-c3ccnc(C(C)(C)O)n3)ncc2C)c(=O)c1Cl)c1ccccc1] | 3-Chloro-2'-(2-(2-hydroxypropan-2-yl)pyrimidin-4-yl)-5',6-dimethyl-4-(phenylmethoxy-d$_2$)-2H-[1,4'-bipyridin]-2-one, (atropisomer 2) |
| 7 | 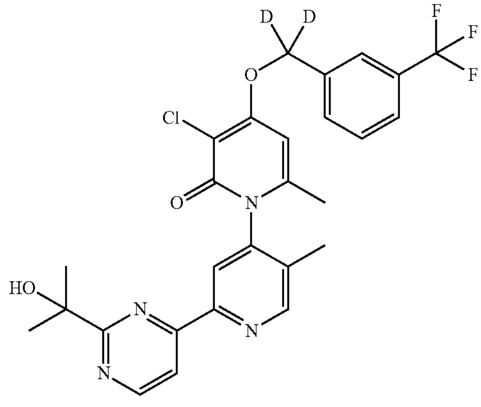 [SMILES: [2H]C([2H])(Oc1cc(C)n(-c2cc(-c3ccnc(C(C)(C)O)n3)ncc2C)c(=O)c1Cl)c1cccc(C(F)(F)F)c1] | 3-Chloro-2-(2-(2-hydroxypropan-2-yl)pyrimidin-4-yl)-5',6-dimethyl-4-((3-(trifluoromethyl)phenyl)methoxy-d$_2$)-2H-[1,4'-bipyridin]-2-one, (atropisomer 1) |

-continued

| Example Number | Structure | Compound Name |
|---|---|---|
| 8 | 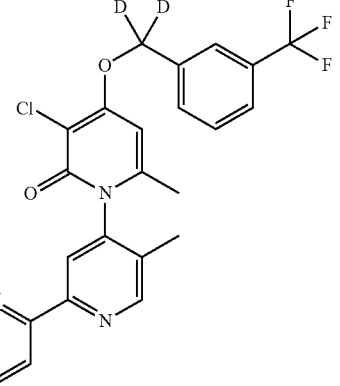 | 3-Chloro-2-(2-(2-hydroxypropan-2-yl)pyrimidin-4-yl)-5',6-dimethyl-4-((3-(trifluoromethyl)phenyl)methoxy-d$_2$)-2H-[1,4'-bipyridin]-2-one, (atropisomer 2) |
| 9 | 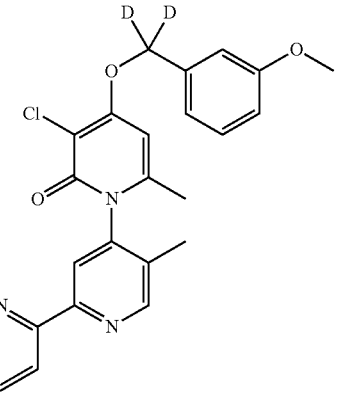 | 3-Chloro-2'-(2-(2-hydroxypropan-2-yl)pyrimidin-4-yl)-4-((3-methoxyphenyl)methoxy-d$_2$)-5',6-dimethyl-2H-[1,4'-bipyridin]-2-one, (atropisomer 1) |
| 10 | 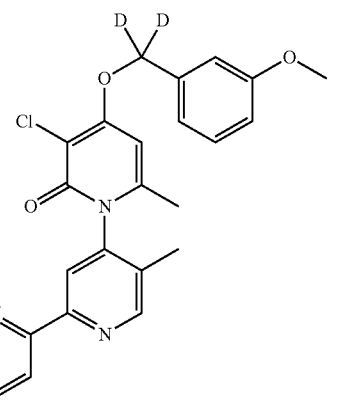 | 3-Chloro-2'-(2-(2-hydroxypropan-2-yl)pyrimidin-4-yl)-4-((3-methoxyphenyl) methoxy-d$_2$)-5',6-dimethyl-2H-[1,4'-bipyridin]-2-one, (atropisomer 2) |

-continued

| Example Number | Structure | Compound Name |
|---|---|---|
| 11 | 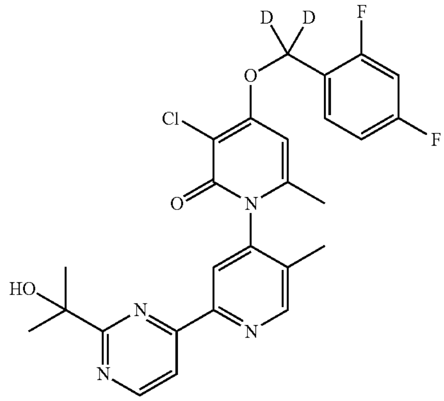 | 3-Chloro-4-((2,4-difluorophenyl)methoxy-d$_2$)-2'-(2-(2-hydroxypropan-2-yl)pyrimidin-4-yl)-5',6-dimethyl-2H-[1,4'-bipyridin]-2-one, (atropisomer 1) |
| 12 | 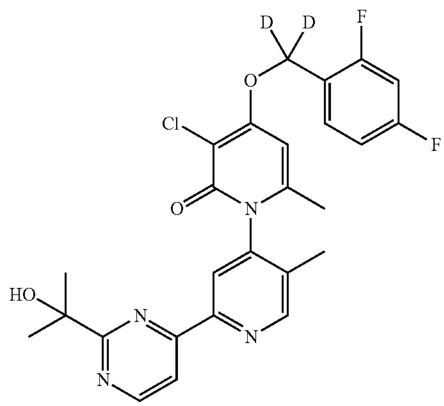 | 3-Chloro-4-((2,4-difluorophenyl)methoxy-d$_2$)-2'-(2-(2-hydroxypropan-2-yl)pyrimidin-4-yl)-5',6-dimethyl-2H-[1,4'-bipyridin]-2-one, (atropisomer 2) |
| 13 | 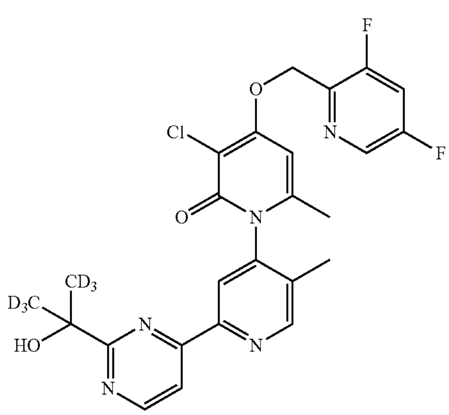 [SMILES: [2H]C([2H])([2H])C(O)(c1nccc(-c2cc(-n3c(C)cc(OCc4ncc(F)cc4F)c(Cl)c3=O)c(C)cn2)n1)C([2H])([2H])[2H]] | 3-Chloro-4-((3,5-difluoropyridin-2-yl)methoxy)-2'-(2-(2-hydroxypropan-2-yl-1,1,1,3,3,3-d$_6$)pyrimidin-4-yl)-5',6-dimethyl-2H-[1,4'-bipyridin]-2-one, (atropisomer 1) |

| Example Number | Structure | Compound Name |
|---|---|---|
| 14 | 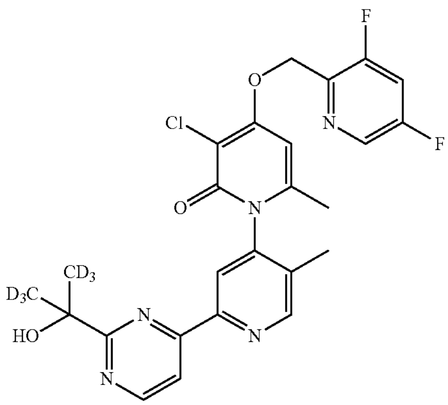 [SMILES: [2H]C([2H])([2H])C(O)(c1nccc(-c2cc(-n3c(C)cc(OCc4ncc(F)cc4F)c(Cl)c3=O)c(C)cn2)n1)C([2H])([2H])[2H]] | 3-Chloro-4-((3,5-difluoropyridin-2-yl)methoxy)-2'-(2-(2-hydroxypropan-2-yl-1,1,1,3,3,3-d₆)pyrimidin-4-yl)-5',6-dimethyl-2H-[1,4'-bipyridin]-2-one, (atropisomer 2) |
| 15 | 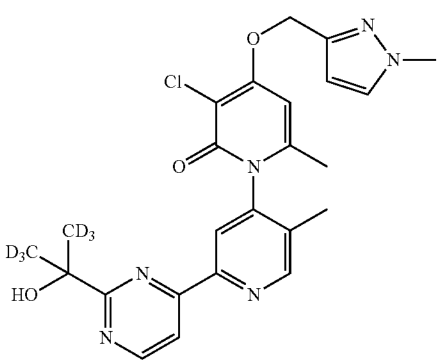 [SMILES: [2H]C([2H])([2H])C(O)(c1nccc(-c2cc(-n3c(C)cc(OCc4ccn(C)n4)c(Cl)c3=O)c(C)cn2)n1)C([2H])([2H])[2H]] | 3-Chloro-2'-(2-(2-hydroxypropan-2-yl-1,1,1,3,3,3-d₆)pyrimidin-4-yl)-5',6-dimethyl-4-((1-methyl-1H-pyrazol-3-yl)methoxy)-2H-[1,4'-bipyridin]-2-one, (atropisomer 1) |
| 16 | 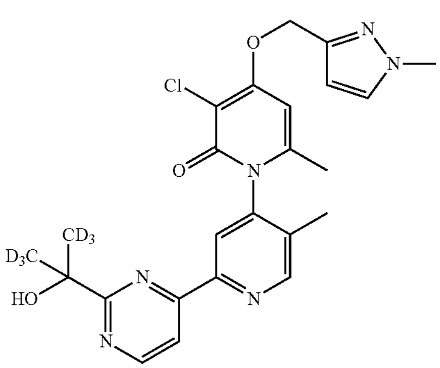 [SMILES: [2H]C([2H])([2H])C(O)(c1nccc(-c2cc(-n3c(C)cc(OCc4ccn(C)n4)c(Cl)c3=O)c(C)cn2)n1)C([2H])([2H])[2H]] | 3-Chloro-2'-(2-(2-hydroxypropan-2-yl-1,1,1,3,3,3-d₆)pyrimidin-4-yl)-5',6-dimethyl-4-((1-methyl-1H-pyrazol-3-yl)methoxy)-2H-[1,4'-bipyridin]-2-one, (atropisomer 2) |

Some embodiments provide a compound having the structure:

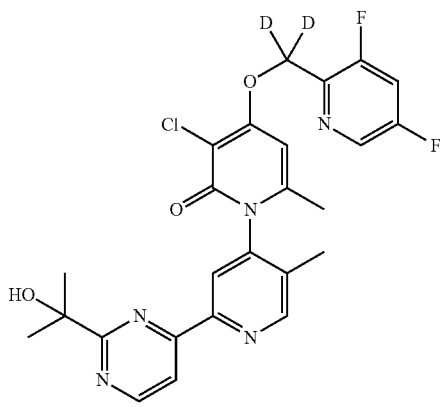 [SMILES: [2H]C([2H])(Oc1cc(C)n(-c2cc(-c3ccnc(C(C)(C)O)n3)ncc2C)c(=O)c1Cl)c1ncc(F)cc1F]

3-Chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof.

In some embodiments, 3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof, is a single atropisomer and wherein the single atropisomer is (P)-3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof. In some embodiments (P)-3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof, has an atropisomeric purity of about about 90% or greater over the corresponding M isomer, about 91% or greater over the corresponding M isomer, about 92% or greater over the corresponding M isomer, about 93% or greater over the corresponding M isomer, about 94% or greater over the corresponding M isomer, about 95% or greater over the corresponding M isomer, about 96% or greater over the corresponding M isomer, about 97% or greater over the corresponding M isomer, about 97.5% or greater over the corresponding M isomer, about 98% or greater over the corresponding M isomer, about 99% or greater over the corresponding M isomer, about 99.1% or greater over the corresponding M isomer, about 99.2% or greater over the corresponding M isomer, about 99.3% or greater over the corresponding M isomer, about 99.4% or greater over the corresponding M isomer, about 99.5% or greater over the corresponding M isomer, about 99.6% or greater over the corresponding M isomer, about 99.7% or greater over the corresponding M isomer, about 99.75% or greater over the corresponding M isomer, about 99.8% or greater over the corresponding M isomer, about 99.9% or greater over the corresponding M isomer, about 99.91% or greater over the corresponding M isomer, about 99.92% or greater over the corresponding M isomer, about 99.93% or greater over the corresponding M isomer, about 99.94% or greater over the corresponding M isomer, about 99.95% or greater over the corresponding M isomer, about 99.96% or greater over the corresponding M isomer, about 99.97% or greater over the corresponding M isomer, about 99.98% or greater over the corresponding M isomer, or about 99.99% or greater over the corresponding M isomer. In some embodiments (P)-3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof, is substantially free of its corresponding M isomer.

In some embodiments, 3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof, is a single atropisomer and wherein the single atropisomer is (M)-3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof. In some embodiments (M)-3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof, has an atropisomeric purity of about about 90% or greater over the corresponding P isomer, about 91% or greater over the corresponding P isomer, about 92% or greater over the corresponding P isomer, about 93% or greater over the corresponding P isomer, about 94% or greater over the corresponding P isomer, about 95% or greater over the corresponding P isomer, about 96% or greater over the corresponding P isomer, about 97% or greater over the corresponding P isomer, about 97.5% or greater over the corresponding P isomer, about 98% or greater over the corresponding P isomer, about 99% or greater over the corresponding P isomer, about 99.1% or greater over the corresponding P isomer, about 99.2% or greater over the corresponding P isomer, about 99.3% or greater over the corresponding P isomer, about 99.4% or greater over the corresponding P isomer, about 99.5% or greater over the corresponding P isomer, about 99.6% or greater over the corresponding P isomer, about 99.7% or greater over the corresponding P isomer, about 99.75% or greater over the corresponding P isomer, about 99.8% or greater over the corresponding P isomer, about 99.9% or greater over the corresponding P isomer, about 99.91% or greater over the corresponding P isomer, about 99.92% or greater over the corresponding P isomer, about 99.93% or greater over the corresponding P isomer, about 99.94% or greater over the corresponding P isomer, about 99.95% or greater over the corresponding P isomer, about 99.96% or greater over the corresponding P isomer, about 99.97% or greater over the corresponding P isomer, about 99.98% or greater over the corresponding P isomer, or about 99.99% or greater over the corresponding P isomer. In some embodiments (M)-3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof, is substantially free of its corresponding P isomer.

In some embodiments, the compounds of Formula (I), or a derivative thereof, exist as a mixture of P and M atropisomers wherein the mixture may exist in any proportion of P and M atropisomers.

In some embodiments, the compounds of Formula (I), or a derivative thereof, may be separated into individual atropisomers shown in Formula (P)-II, or a derivative thereof, and Formula (M)-II, or a derivative thereof:

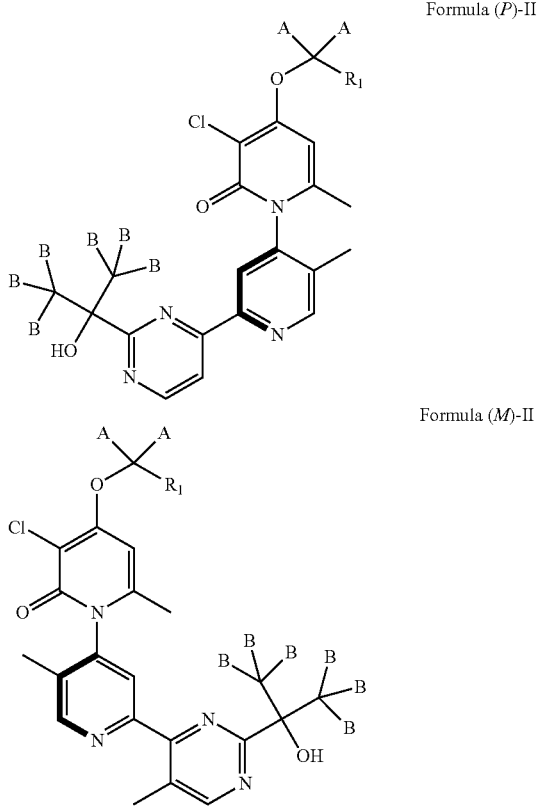

Formula (P)-II

Formula (M)-II

In certain embodiments the compound of Formula (P)-II, is substantially free of its corresponding M isomer. In certain embodiments the compound of Formula (P)-II, contains 0% of its corresponding M isomer. In certain embodiments the compound of Formula (P)-II, contains less than 0.01% of its corresponding M isomer. In certain embodiments the compound of Formula (P)-II, contains less than 0.05% of its corresponding M isomer. In certain embodiments the compound of Formula (P)-II, contains less than 0.1% of its corresponding M isomer. In certain embodiments the compound of Formula (P)-II, contains less than 0.5% of its corresponding M isomer. In certain embodiments the compound of Formula (P)-II, contains less than 1% of its corresponding M isomer. In certain embodiments the compound of Formula (P)-II, contains less than 1.5% of its corresponding M isomer. In certain embodiments the compound of Formula (P)-II, contains less than 2% of its corresponding M isomer. In certain embodiments the compound of Formula (P)-II, contains less than 2.5% of its corresponding M isomer. In certain embodiments the compound of Formula (P)-II, contains less than 2% of its corresponding M isomer. In certain embodiments the compound of Formula (P)-II, contains less than 3.5% of its corresponding M isomer. In certain embodiments the compound of Formula (P)-II, contains less than 4% of its corresponding M isomer. In certain embodiments the compound of Formula (P)-II, contains less than 4.5% of its corresponding M isomer. In certain embodiments the compound of Formula (P)-II, contains less than 5% of its corresponding M isomer.

In certain embodiments the compound of Formula (M)-II, is substantially free of its corresponding P isomer. In certain embodiments the compound of Formula (M)-II, contains 0% of its corresponding P isomer. In certain embodiments the compound of Formula (M)-II, contains less than 0.01% of its corresponding P isomer. In certain embodiments the compound of Formula (M)-II, contains less than 0.05% of its corresponding P isomer. In certain embodiments the compound of Formula (M)-II, contains less than 0.1% of its corresponding P isomer. In certain embodiments the compound of Formula (M)-II, contains less than 0.5% of its corresponding P isomer. In certain embodiments the compound of Formula (M)-II, contains less than 1% of its corresponding P isomer. In certain embodiments the compound of Formula (M)-II, contains less than 1.5% of its corresponding P isomer. In certain embodiments the compound of Formula (M)-II, contains less than 2% of its corresponding P isomer. In certain embodiments the compound of Formula (M)-II, contains less than 2.5% of its corresponding P isomer. In certain embodiments the compound of Formula (M)-II, contains less than 3% of its corresponding P isomer. In certain embodiments the compound of Formula (M)-II, contains less than 3.5% of its corresponding P isomer. In certain embodiments the compound of Formula (M)-II, contains less than 4% of its corresponding P isomer. In certain embodiments the compound of Formula (M)-II, contains less than 4.5% of its corresponding P isomer. In certain embodiments the compound of Formula (M)-II, contains less than 5% of its corresponding P isomer.

In certain embodiments of the compounds disclosed herein the isotopic enrichment at each position labeled in the structure is equal to or greater than 70%. In certain embodiments of the invention the isotopic enrichment at each position labeled in the structure is equal to or greater than 80%. In certain embodiments of the invention the isotopic enrichment at each position labeled in the structure is equal to or greater than 90%. In certain embodiments of the invention the isotopic enrichment at each position labeled in the structure is equal to or greater than 95%. In certain embodiments of the invention the isotopic enrichment at each position labeled in the structure is equal to or greater than 99%.

Pharmaceutical Compositions

Some embodiments herein are directed to a pharmaceutical composition comprising a compound of Formula (I) as described herein and a pharmaceutically acceptable excipient. In certain embodiments each of the pharmaceutical compositions comprising a compound of Formula (P)-II, or a derivative thereof, the pharmaceutical composition is substantially free of its corresponding M isomer. In certain embodiments each of the pharmaceutical compositions comprising a compound of Formula (M)-II, or a derivative thereof, the pharmaceutical composition is substantially free of its corresponding P isomer.

Also provided is a pharmaceutical composition comprising a compound as disclosed herein, together with a pharmaceutically acceptable excipient.

While it may be possible for the compounds described herein to be administered as the raw chemical, it is also possible to present them as a pharmaceutical composition. Accordingly, provided herein are pharmaceutical compositions which comprise one or more of certain compounds disclosed herein, or a derivative thereof, together with one or more pharmaceutically acceptable excipients thereof and optionally one or more other therapeutic ingredients. The excipient(s) must be "acceptable" in the sense of being compatible with the other ingredients of the formulation and not deleterious to the recipient thereof. Proper formulation of the pharmaceutical composition is dependent upon the route of administration chosen. Any of the well-known techniques and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

In some embodiments, the pharmaceutical compositions for use in accordance with embodiments herein can be formulated in conventional manner using one or more physiologically acceptable excipients.

The compositions include those suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration although the most suitable route may depend upon for example the condition and disorder of the recipient. The composition could include those suitable for administration by depot injections or by implants. The composition could include those suitable for administration by inhalation, such as, for example, a gas, vapor, or powder. The composition could include those suitable for administration, e.g., as an aerosol via a nebulizer, humidifier, inhaler and vaporizer or the like. The compositions may conveniently be presented in unit dosage form and may be prepared by any of the methods well known in the art of pharmacy. Typically, these methods include the step of bringing into association a compound disclosed herein or a derivative thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired composition.

Compositions of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All compositions for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Compositions for injection may be presented in unit dosage form, e.g., in ampoules or in multi-dose containers, with an added preservative. The pharmaceutical compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the composition isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the pharmaceutical compositions described previously, the compounds may also be formulated as a depot preparation. Such long acting compositions may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the pharmaceutical compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose. In contrast, systemic administration refers to oral, intravenous, intraperitoneal and intramuscular administration.

In some embodiments, the compounds disclosed herein may be administered ophthalmically. In some embodiments, the compounds disclosed herein may be administered as an ophthalmic composition. The compounds of embodiments herein may be administered as, for example, liquid preparations, including eye lotions, spray, or eye drops for topical administration. In some embodiments, the compounds disclosed herein may be administered as semi-solid preparations, for example, applied to the eyelid, such as cream, lotion, gel, ointment, or paste. In some embodiments, the compounds disclosed herein may be administered as solid dosage forms, for example, applied to the eye surface to produce modified release, such as a powder. In some embodiments, the compounds of embodiments herein are administered through devices for surgical implantation, parenteral products, (e.g., intracorneal or intravitreous products), liquids for irrigation, or the like. In some embodiments, the pharmaceutical composition comprising the compounds disclosed herein are sterile and free from particulate matters. In some embodiments, the compounds disclosed herein may be administered by intraocular injection, intraorbital injection, or an intravitreal injection. In some embodiments, the intraocular injection may be to the anterior chamber of the eye, posterior chamber of the eye, or a combination thereof. For example, the compounds disclosed herein may be administered to the posterior intraorbital region of the eye.

In some embodiments, pharmaceutical compositions suitable for topical administration include liquid or semi-liquid preparations suitable for penetration through the skin to the site of inflammation such as a solution, powder, fluid emulsion, fluid suspension, semi-solid, ointment, paste, cream, gel, jelly, foam, liniment, lotion, and drops suitable for administration to the eye, ear or nose. The active ingredient for topical administration may comprise, for example, from 0.001% to 10% w/w (by weight) of the composition. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the composition.

Gels for topical or transdermal administration may comprise, generally, a mixture of volatile solvents, nonvolatile solvents, and water. In certain embodiments, the volatile solvent component of the buffered solvent system may include lower ($C_1$-$C_6$)alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid pharmaceutical compositions of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The pharmaceutical composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Pharmaceutical compositions for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage pharmaceutical compositions are those containing an effective dose, as herein below recited, or an appropriate fraction thereof, of the active ingredient.

It should be understood that in addition to the ingredients particularly mentioned above, the pharmaceutical compositions described above may include other agents conventional in the art having regard to the type of pharmaceutical composition in question, for example those suitable for oral administration may include flavoring agents.

Compounds may be administered at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

When employed as pharmaceuticals, the compounds can be administered in the form of pharmaceutical compositions. These compositions can be prepared in a manner well known in the pharmaceutical arts, and can be administered by a variety of routes, depending upon whether local or systemic treatment is desired and upon the area to be treated. Administration of the disclosed compounds or compositions may be oral, parenteral (including subcutaneous, intradermal, intramuscular, intravenous, intraarticular, and intramedullary), pulmonary (e.g., by inhalation or insufflation of powders or aerosols, including by nebulizer; intratracheal or intranasal), intraperitoneal, transmucosal, transdermal, rectal, topical (including dermal, buccal, sublingual and intraocular), or intravaginal administration. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions for topical administration may include foams, transdermal patches, ointments, lotions, creams, gels, solutions, fluid emulsions, fluid suspensions, semi-solids, pastes, drops, suppositories, sprays, liquids and powders. Conventional pharmaceutical carriers, aqueous, powder or oily bases, thickeners and the like may be necessary or desirable. Coated condoms, gloves and the like may also be useful. In some embodiments, the compounds can be contained in such pharmaceutical compositions with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The artisan can refer to various pharmacologic references for guidance. For example, Modern Pharmaceutics, 5th Edition, Banker & Rhodes, CRC Press (2009); and Goodman & Gilman's The Pharmaceutical Basis of Therapeutics, 13th Edition, McGraw Hill, New York (2018) can be consulted.

In some embodiments, a method of treating a p38 MAP Kinase mediated disease comprises administering a pharmaceutical composition of embodiments disclosed herein. In some embodiments, the compound is in a therapeutically effective amount. In some embodiments, the therapeutically effective amount is an amount disclosed herein.

Some embodiments disclosed herein also include pharmaceutical compositions which contain, as the active ingredient, one or more of the compounds disclosed herein in combination with one or more pharmaceutically acceptable carriers (excipients).

In some embodiments, a method of making a pharmaceutical composition comprises mixing the active ingredient with an excipient, diluting the active ingredient using an excipient, or enclosing the active ingredient within a carrier in the form of, for example, a capsule, sachet, paper, or other container. When the excipient serves as a diluent, it can be a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose, including eutectic solvents, eutectic-based ionic liquids, or ionic liquids. The pharmaceutical compositions can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The pharmaceutical compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the pharmaceutical composition may comprise about 0.01% to about 50% of one or more compounds disclosed herein. In some embodiments, the one or more compounds is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the pharmaceutical composition. In some embodiments, the pharmaceutical composition is suitable for topical administration. In some embodiments, the pharmaceutical composition is suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration.

In some embodiments, the compound is in a therapeutically effective amount. In some embodiments, the therapeutically effective amount may be about 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, or any value between the ranges disclosed above.

In some embodiments, the therapeutically effective amount can vary according to, for example, the particular use for which the treatment is made, the manner of administration of the compound, the health and condition of the patient, and the judgment of the prescribing physician. The proportion or concentration of a compound in a pharmaceutical composition can vary depending upon a number of factors including dosage, chemical characteristics (e.g., hydrophobicity), and the route of administration. For example, the compounds can be provided in an aqueous physiological buffer solution containing about 0.1 to about 10% w/v of the compound for parenteral administration.

Some typical dose ranges for the compounds are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, composition of the excipient, and its route of administration. Effective doses can be extrapolated from dose-response curves derived from in vitro or animal model test systems.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the pharmaceutical composition so that the pharmaceutical composition can be readily subdivided into equally therapeutically effective unit dosage forms such as tablets, pills and capsules. This solid pre-formulation is then subdivided into unit dosage forms of the type described above containing from, for example, about 0.1 to about 1000 mg of the active ingredient.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the pharmaceutical compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the composition in an appropriate manner.

In some embodiments, the pharmaceutical compositions administered to a patient can be in the form of pharmaceutical compositions described above. In some embodiments, these compositions can be sterilized by conventional sterilization techniques, or may be sterile filtered. Aqueous solutions can be packaged for use as is, or lyophilized, the lyophilized preparation being combined with a sterile aqueous carrier prior to administration. In some embodiments, the pH of the compound preparations is about 3 to about 11, about 5 to about 9, about 5.5 to about 6.5, or about 5.5 to about 7.5. It will be understood that use of certain of the foregoing excipients, carriers, or stabilizers will result in the formation of pharmaceutical salts.

Methods of Use

The present invention relates to a method of modulating a p38 MAP Kinase mediated function in a subject comprising the administration of a therapeutically effective amount of a compound of Formula (I) or a pharmaceutical composition containing said compound as disclosed herein. In certain embodiments the compound administered is a compound of Formula (P)-II, or a derivative thereof, or a pharmaceutical composition comprising the same, that is substantially free of its corresponding M isomer. In certain embodiments the compound administered is a compound of Formula (M)-II, or a derivative thereof, or a pharmaceutical composition comprising the same, that is substantially free of its corresponding P isomer.

In some embodiments the compound administered is 3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof, or a pharmaceutical composition comprising the same. In some embodiments the compound administered is (P)-3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof, or a pharmaceutical composition comprising the same, that is substantially free of its corresponding M isomer. In some embodiments the compound administered is (M)-3-chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a derivative thereof, or a pharmaceutical composition comprising the same, that is substantially free of its corresponding P isomer.

The present invention also relates to a method of inhibiting at least one p38 MAP Kinase function comprising the step of contacting p38 MAP Kinase with a compound as described herein. The cell phenotype, cell proliferation, activity of p38 MAP Kinase, change in biochemical output produced by active p38 MAP Kinase, expression of p38 MAP Kinase, or binding of p38 MAP Kinase with a natural binding partner may be monitored to determine the level of p38 MAP kinase modulation achieved with the compounds described herein. Such methods may be modes of treatment of disease, biological assays, cellular assays, biochemical assays, or the like.

Also provided herein is a method of treating a p38 MAP Kinase mediated disease comprising administering to a patient in need thereof a therapeutically effective amount of a compound as disclosed herein, a derivative thereof, or a combination thereof. In certain embodiments, the therapeutically effective amount of a compound as disclosed herein, a derivative thereof, or a combination thereof, may be in the form of a pharmaceutical composition. In embodiments, the pharmaceutical composition may include a pharmaceutically acceptable excipient.

In embodiments, diseases or disorders associated with a p38 MAP Kinase that are treated by compounds of the present invention include autoimmune disorders, chronic inflammatory disorders, acute inflammatory disorders, autoinflammatory disorders, fibrotic disorders, metabolic disorders, neoplasias, or cardiovascular or cerebrovascular disorders. Thus, in some embodiments, the present invention provides a method for treating a p38 MAP Kinase mediated disease or disorder in a patient in need thereof, wherein said method comprises administering to said patient a therapeutically effective amount of a provided compound, or composition thereof. Such p38 MAP Kinase mediated diseases or disorders include, but are not limited to, those described herein.

In some embodiments, said p38 MAP Kinase mediated disease or disorder is chosen from a skin disorder, pruritus, a hair loss disorder, a cancer, a neoplasm, Alzheimer's disease, an inflammatory condition, connective tissue diseases and an autoimmune condition.

In certain embodiments, said p38 MAP Kinase mediated disease or disorder is a neoplasm, a malignancy, a myeloproliferative disorder, a hematopoietic neoplasm, a myeloid neoplasm, a lymphoid neoplasm, including myelofibrosis, primary myelofibrosis, polycythemia vera, essential thrombocythemia, acute and chronic leukemias, lymphomas, cutaneous lymphomas including mycosis fungoides, other myeloid malignancies, and myelodysplastic syndrome.

In one embodiment, the inflammatory condition to be treated in accordance with the methods and compositions described herein is selected from rheumatoid arthritis, psoriatic arthritis, psoriasis, plaque psoriasis, gout, inflammatory bowel disease, hidradenitis suppurativa, Cryopyrin associated periodic syndrome (CAPS), pericarditis, including acute, chronic, and recurring pericarditis, ankylosing spondylitis, systemic juvenile idiopathic arthritis, systemic lupus erythematosus, multiple sclerosis, an inflammatory bone disorder, osteoarthritis, septic shock, endotoxic shock, endotoxin-induced toxic shock, toxic shock syndrome, sepsis, septic shock, atherosclerosis, diabetes, asthma, reperfusion injury, neuronal ischemia, stroke, graft versus host disease, allograft rejection, glomerulonephritis, pulmonary inflammation, chronic obstructive pulmonary disease (COPD), acute coronary syndrome, heart failure, atopic dermatitis, cancer (e.g., breast, pancreatic, colorectal, and lung cancer), fibrotic disease, cytokine release syndrome, and acute respiratory distress syndrome.

In some embodiments, the inflammatory condition that is treated in accordance with the methods described here is arthritis, in particular rheumatoid arthritis. In some embodiments, the condition that is treated is hidradenitis suppurativa. In some embodiments, the inflammatory condition to be treated is gout. In some embodiments, the inflammatory condition to be treated is plaque psoriasis or psoriatic arthritis. In some embodiments, the inflammatory condition to be treated is ankylosing spondylitis. In some embodiments, the inflammatory condition to be treated is pericarditis, including acute pericarditis, recurrent pericarditis, and chronic pericarditis. In some embodiments, the inflammatory condition to be treated is Cryopyrin associated periodic syndrome (CAPS), including Muckle Wells Syndrome and Familial Cold Autoinflammatory Syndrome (FCAS). In some embodiments, the inflammatory condition to be treated is pyoderma gangrenosum. In some embodiments, the condition to be treated is inflammatory bowel disease, including Crohn's disease and ulcerative colitis. In some embodiments, the inflammatory condition to be treated is Stills disease, also referred to as juvenile idiopathic arthritis. In some embodiments, the inflammatory condition to be treated is atopic dermatitis. In some embodiments, the inflammatory condition to be treated is acute coronary syndrome. In some embodiments, the condition to be treated is heart failure. In some embodiments, the inflammatory condition to be treated is cancer, including, but not limited to, breast cancer, pancreatic cancer, colorectal cancer and lung cancer. In some embodiments, the inflammatory condition is cytokine release syndrome. In some embodiments, the inflammatory condition is acute respiratory distress syndrome.

In some embodiments the methods described herein are used to treat patients with disorders arising from dysregulated cytokine, enzymes and/or inflammatory mediator production, stability, secretion, posttranslational processing. In some embodiments, the methods described herein are used to treat patients having cytokine release syndrome, which is a systemic inflammatory response triggered by a variety of factors including infections (e.g., viral infection) and certain drugs (CAR T-cell therapy). Examples of cytokines that may be dysregulated include interleukins 1, 2, 6, 8, 10, 12, 17, 22 and 23 along with tumor necrosis factor alpha and interferons alpha, beta and gamma. Examples of inflammatory mediators that may be dysregulated include nitric oxide, prostaglandins and leukotrienes. Examples of enzymes include cyclo-oxygenase, nitric oxide synthase and matrix metalloprotease.

In certain embodiments, said p38 MAP Kinase mediated disease is selected from the group consisting of an autoimmune disorders or responses, broad activation of the immune responses, bacterial infection, viral infection, inflammation, a chronic and/or acute inflammatory disorder or condition, and/or auto-inflammatory disorder, fibrotic disorders, metabolic disorders, a neoplasm, or cardiovascular or cerebrovascular disorders, a skin disorder, pruritus, a hair loss disorder, a cancer or malignancy, autoimmune connective tissue diseases and an autoimmune condition; Still's disease, adult-onset Still's disease, Th17-associated inflammation, polychondritis (e.g. relapsing polychondritis); myositis, polymyositis, autoimmune myositis, dermatomyositis, juvenile dermatomyositis; myasthenia gravis; Arthritis (e.g. rheumatoid arthritis, juvenile rheumatoid arthritis, systemic-onset juvenile rheumatoid arthritis, osteoarthritis, infectious arthritis, inflammatory arthritis, inflammatory bowel disease-associated arthritis, idiopathic arthritis, juvenile idiopathic arthritis, systemic juvenile idiopathic arthritis, psoriatic arthritis), spondylitis/spondyloarthritis/spondyloarthropathy (ankylosing spondylitis), gout, scleroderma (systemic scleroderma, juvenile scleroderma), Reiter's syndrome/reactive arthritis, Lyme disease, lupus/systemic lupus erythematosus (SLE) (lupus erythematosus, pediatric systemic lupus erythematosus, cutaneous lupus (subacute cutaneous lupus, chronic cutaneous lupus/discoid lupus, chilblain lupus erythematosus), polymyalgia rheumatica, enthesitis, mixed connective tissue disease, enthesopathy; carditis, myocarditis, angiogenesis disorders, myelodysplastic syndrome, atherosclerosis, restenosis (restenosis of an atherosclerotic coronary artery), acute coronary syndrome, myocardial infarction, cardiac-allograft vasculopathy, transplant arteriopathy; vasculitis (large vessel vasculitis, small vessel vasculitis, giant-cell arteritis, polyarteritis nodosa, vasculitis syndromes including: Takayasu's arteritis, Wegener's granulomatosis, Behcet's Disease), stimulator of interferon genes (STING) associated vasculopathy with onset in infancy (SAVI); gastrointestinal disorders, enterocolitis, colitis, inflammatory bowel disease (ulcerative colitis, Crohn's disease), irritable bowel syndrome, enteritis syndrome/spastic colon, celiac disease; acute and chronic pancreatitis; primary biliary cirrhosis, primary sclerosing cholangitis, jaundice, cirrhosis (for example, primary biliary cirrhosis or cirrhosis due to fatty liver disease (for example, alcoholic and nonalcoholic steatosis); esophagitis, gastritis, gastric and duodenal ulcers, peritonitis; Nephropathies: immunologically mediated glomerulonephropathy, autoimmune nephropathy, membranous glomerulopathy, chronic progressive nephropathies, diabetic kidney disease/diabetic nephropathy, renal fibrosis, renal ischemic/reperfusion injury, HIV associated nephropathy, ureteral obstructive nephropathy, glomerulosclerosis, proteinuria, nephrotic syndrome, polycystic kidney disease, autosomal dominant polycystic kidney disease, a nephropathy is an immunologically mediated nephropathy, autoimmune nephropathy, chronic progressive nephropathies, diabetic nephropathy, renal fibrosis, ischemic/reperfusion injury associated, HIV associated nephropathy, ureteral obstructive nephropathy, glomerulonephritis, chronic kidney disease (for example, diabetic nephropathy), hypertension induced nephropathy, glomerulosclerosis, proteinuria, nephrotic syndrome, polycystic kidney disease, autosomal dominant polycystic kidney disease, diabetic kidney disease, lupus nephritis; interstitial cystitis; periodontitis, gingivitis; pulmonary inflammation, sinusitis, pneumonia, bronchitis, asthma, bronchial asthma, allergic asthma, non-allergic asthma, allergic bronchopulmonary mycosis, aspirin-induced asthma, adult-onset asthma, asthma with fixed airflow obstruction, exercise-induced asthma, cough-variant asthma, work-related asthma, nighttime (nocturnal) asthma, asthma with obesity, eosinophilic asthma, steroid-resistant asthma/severe asthma, extrinsic asthma, intrinsic/cryptogenic asthma, Churg-Strauss syndrome, bronchiolitis, bronchiolitis obliterans, chronic obstructive pulmonary disease (COPD), interstitial lung disease (pulmonary fibrosis, idiopathic pulmonary fibrosis), acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury; Meniere's disease; ocular disorders including, (e.g.), ocular inflammation, uveitis, dry eye/keratoconjunctivitis sicca, scleritis, episcleritis, keratitis/keratopathy, choroiditis, retinal vasculitis, optic neuritis, retinopathy (diabetic retinopathy, immune mediated retinopathy, macular degeneration, wet macular degeneration, dry (age related) macular degeneration); Mastocytosis, iron deficiency anemia, uremia, hypereosinophilic syndrome (HES), systemic mast cell disease (SMCD), myelodysplastic syndrome, idiopathic thrombocytic purpura; bone resorption diseases; Neurodegenerative disorders, neurological/neuromuscular disorders (e.g.), multiple sclerosis, Parkinson's disease, Huntington's disease, amyotrophic lateral sclerosis (ALS) (familial ALS, sporadic ALS), Alzheimer's disease, myasthenia gravis, Lambert-Eaton myasthenic syndrome (LEMS), Guillain-Barret syndrome, meningitis, encephalitis, traumatic brain injury; nervous system damage, delusional parasitosis, dysregulation of neuronal processes and sensory perception, stroke/neuronal ischemia, spinal cord injury, peripheral neuropathy, tactile hallucinations, spinal cord injury, psychiatric disease; pain (acute pain, chronic pain, neuropathic pain, or fibromyalgia) paresthetica, nerve irritation, peripheral neuropathy; pruritus/itch (atopic pruritus, xerotic pruritus, pruritus associated with psoriasis/psoriatic itch/psoriasis-associated itch), acute pruritus, chronic pruritus, idiopathic pruritus, chronic idiopathic itch, biliary itch, hepatobiliary-associated itch, renal associated itch/renal itch, uremic itch, cholestasis, intrahepatic cholestasis of pregnancy, lichen simplex chronicus associated pruritus, lymphoma-associated itch, leukemia-associated itch, prurigo nodularis, atopic dermatitis-associated itch, atopic itch/atopic pruritus, bullous itch, brachioradial pruritus) neurogenic itch, neuropathic itch, notalgia paresthetica, pruritic popular eruption of HIV, psychogenic itch, swimmer's itch, pruritus or uremic itch, urticarial itch; dermatologic disorders (e.g.), dermatologic drug reactions/drug eruptions, xerosis/dry skin, skin rash, skin sensitization, skin irritation, sunburn, shaving, body louse, head lice/pediculosis, pubic lice, cutaneous larva migrans, scabies, parasitic infection, insect infestation, urticaria/hives, papular uritcaria, insect bites, insect stings, dandruff, foreign objects or devices on skin, fungal infection, herpes, varicella/chicken pox, eosinophilic folliculitis, dermatosis of pregnancy/pruritic urticarial papules and plaques of pregnancy (PUPP), inflammatory dermatoses, neutrophilic dermatoses, histiocytoid neutrophilic dermatosis, bowel-bypass syndrome dermatosis, psoriasis/psoriasis vulgaris, lichen planus, lichen sclerosus, acne (acne vulgaris, comedonal acne, inflammatory acne, nodulo-cystic acne, scarring acne, acne keloidalis nuchae), atopies (allergic contact sensitization, allergic dermatitis) dermatitis (atopic dermatitis/eczema, contact dermatitis, photodermatitis, seborrheic dermatitis, stasis dermatitis, acute febrile neutrophilic dermatosis (Sweet's syndrome), chronic atypical neutrophilic dermatitis with lipodystrophy and elevated temperature syndrome (CANDLE Syndrome), hidradenitis suppurativa, hives, pyoderma gangrenosum, alopecia (eyebrow alopecia, intranasal hair alopecia, scarring alopecia (e.g., cicatricial alopecia, central centrifugal cicatricial alopecia, lichen planopilaris, frontal fibrosing alopecia, folliculitis decalvans), nonscarring alopecia (alopecia areata (AA) (patchy AA, alopecia totalis (AT), alopecia universalis (AU), ophiasis pattern alopecia areata, sisaihpo pattern alopecia areata)), androgenetic/androgenic alopecia (AGA)/male and female pattern AGA), telogen effluvium, tinea capitis, hypotrichosis (hereditary hypotrichosis simplex), lichen planopilaris (frontal fibrosing alopecia), punctate palmoplantar keratoderma, erythema elevatinum diutinum (EED), neutrophilic eccrine hidradenitis, palisading neutrophilic granulomatous dermatitis, neutrophilic urticarial dermatosis, vitiligo including segmental vitiligo (unisegmental vitiligo, bisegmental vitiligo, multisegmental vitiligo) nonsegmental vitiligo (acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo), mixed vitiligo/nonsegmental associated with segmental vitiligo, focal vitiligo, solitary mucosal vitiligo or vitiligo with or without leukotricia (involvement of body hair); bullous diseases, immunobullous diseases (bullous pemphigoid, cicatricial pemphigoid, pemphigus vulgaris, linear IgA disease), gestational pemphigoid, xeroderma pigmentosum; disorders of fibrosis and scarring: fibroids, hepatic fibrosis, pulmonary fibrosis, idiopathic pulmonary fibrosis, low grade scarring such as, scleroderma, increased fibrosis, keloids, post-surgical scars; wound healing, surgical scarring, radiation induced fibrosis (for example, head and neck, gastrointestinal or pulmonary), CNS scarring, alimentary track or gastrointestinal fibrosis, renal fibrosis, hepatic or biliary fibrosis, liver fibrosis (for example, nonalcoholic steatohepatitis, hepatitis C, or hepatocellular carcinoma), cardiac fibrosis (for example, endomyocardial fibrosis or atrial fibrosis), ophthalmic scarring, fibrosclerosis, scar growth, wound or scab healing, keloid, mediastinal fibrosis, myelofibrosis, retroperitoneal fibrosis/Ormond's disease, progressive massive fibrosis, nephrogenic systemic fibrosis; Sjogren's syndrome, sarcoidosis, familial Mediterranean fever, Cryopyrin associated periodic syndrome (Muckle-Wells syndrome, familial cold auto-inflammatory syndrome/familial cold urticaria/TNF receptor associated periodic syndrome, neonatal-onset multisystem inflammatory disease), hyperoxia induced inflammations, reperfusion injury, post-surgical trauma, tissue injury, elevated temperature syndrome; diabetes (Type I diabetes, Type II diabetes)/diabetes mellitus, Hashimoto's thyroiditis, Graves' disease, Addison's disease, Castleman's disease, hyperparathyroidism, menopause, obesity, steroid-resistance, glucose intolerance, metabolic syndrome, thyroid illness, hypophysitis; systemic immune senescence; autoimmune atrophic gastritis, autoimmune atrophic gastritis of pernicious anemia, autoimmune encephalomyelitis, autoimmune orchitis, Goodpasture's disease, Sjogren's syndrome, autoimmune thrombocytopenia, sympathetic ophthalmia; secondary hematologic manifestations of autoimmune diseases (for example, anemias), autoimmune hemolytic syndromes (autoimmune hemolytic anemia), autoimmune and inflammatory hepatitis, autoimmune ovarian failure, autoimmune thrombocytopenia, silicone implant associated autoimmune disease, drug-induced autoimmunity, HIV-related autoimmune syndromes, metal-induced autoimmunity, autoimmune deafness, autoimmune thyroid disorders; allergy and allergic reactions including hypersensitivity reactions such as Type I hypersensitivity reactions, (e.g. including anaphylaxis), Type II hypersensitivity reactions (e.g. Goodpasture's Disease, autoimmune hemolytic anemia), Type III hypersensitivity reaction diseases (e.g. the Arthus reaction, serum sickness), and Type IV hypersensitivity reactions (e.g. contact dermatitis, allograft rejection); acute and chronic infection, sepsis syndromes (sepsis, septic shock, endotoxic shock, exotoxin-induced toxic shock, gram negative sepsis, gram positive sepsis, fungal sepsis, toxic shock syndrome); acute and chronic infection, sepsis syndromes (sepsis, septic shock, endotoxic shock, exotoxin-induced toxic shock, gram negative sepsis, gram positive sepsis, fungal sepsis, toxic shock syndrome); a rejection: graft vs. host reaction/graft vs. host disease, allograft rejections (for example, acute allograft rejection or chronic allograft rejection), early transplantation rejection; Malignancy, cancer, lymphoma, leukemia, multiple myeloma, a solid tumor, teratoma, metastatic and bone disorders, internal cancers, cancer of the: bone, mouth/pharynx, esophagus, larynx, stomach, intestine, colon, rectum, lung (for example, non-small cell lung cancer or small cell lung cancer), liver (hepatic), pancreas, nerve, brain (for example, glioma, glioblastoma multiforme, astrocytoma, neuroblastoma, and schwannomas), head and neck, throat, ovary, uterus, prostate, testis, bladder, kidney (renal), breast, gall bladder, cervix, thyroid, prostate, eye (ocular malignancies), and skin (melanoma, keratoacanthoma); as well as fibrotic cancers, fibroma, fibroadenomas, fibrosarcomas, a myeloproliferative disorder, neoplasm (hematopoietic neoplasm, a myeloid neoplasm, a lymphoid neoplasm (myelofibrosis, primary myelofibrosis, polycythemia vera, essential thrombocythemia)), leukemias (acute lymphocytic leukemia, acute and chronic myelogenous leukemia, chronic lymphocytic leukemia, acute lymphoblastic leukemia, chronic myelomonocytic leukemia (CMML), or promyelocytic leukemia), multiple myeloma and other myeloid malignancies (myeloid metaplasia with myelofibrosis (MMM), primary myelofibrosis (PMF), idiopathic myelofibrosis (IMF)), lymphomas (Hodgkin's disease, cutaneous lymphomas (cutaneous T-cell lymphoma, mycosis fungoides), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease); Kaposi's sarcoma, rhabdomyosarcoma, seminoma, teratocarcinoma, osteosarcoma, thyroid follicular cancer; increased accumulation of exogenous opioids or synthetic opioids, notalgia paraesthetica, obsessive-compulsive disorders, nostalgia associated with obsessive-compulsive disorders, and a combination thereof.

In some embodiments, the disorders also include, but are not limited to, sexual dysfunctions such as erectile dysfunctions of organic and psychogenic origin, hypoactive sexual desire disorders, sexual arousal disorders, anorgasmia and sexual pain disorders.

In some embodiments, additional exemplary disorders include, but are not limited to: complications from organ transplants (including xenotransplantation) such as graft vs. host reaction (for example, graft vs. host disease), allograft rejections (for example, acute allograft rejection or chronic allograft rejection), early transplantation, diabetes, a myeloproliferative disorder, a rejection (for example, acute allograft rejection); bone resorption diseases, asthma (e.g., bronchial asthma), atopy, autoimmune thyroid disorders, chronic atypical neutrophilic dermatosis with lipodystrophy and elevated temperature syndrome (CANDLE Syndrome), SAVI (stimulator of interferon genes (STING) associated vasculopathy with onset in infancy), ulcerative colitis, inflammatory bowel disease, Crohn's disease, celiac disease, ulcerative colitis, Behcet's disease, myasthenia gravis, nephropathies, and myocarditis, secondary hematologic manifestations of autoimmune diseases (for example, anemias), autoimmune hemolytic syndromes, autoimmune and inflammatory hepatitis, autoimmune ovarian failure, autoimmune orchitis, autoimmune thrombocytopenia, silicone implant associated autoimmune disease, drug-induced autoimmunity, HIV-related autoimmune syndromes; acute and chronic infection, sepsis syndromes (e.g.) sepsis, septic shock, endotoxic shock, exotoxin-induced toxic shock, gram negative sepsis, gram positive sepsis, fungal sepsis, toxic shock syndrome; hyperoxia induced inflammations, reperfusion injury, post-surgical trauma, tissue injury, pain (e.g.) acute pain, chronic pain, neuropathic pain, or fibromyalgia.

In an embodiment, said asthma is allergic asthma, non-allergic asthma, allergic bronchopulmonary mycosis, aspirin-induced asthma, adult-onset asthma, asthma with fixed airflow obstruction, exercise-induced asthma, cough-variant asthma, work-related asthma, nighttime (nocturnal) asthma, asthma with obesity, eosinophilic asthma, steroid-resistant asthma/severe asthma, extrinsic asthma, or intrinsic/cryptogenic asthma.

In an embodiment, said vitiligo is segmental vitiligo including unisegmental, bisegmental or multisegmental vitiligo, non-segmental vitiligo including acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo, mixed vitiligo (nonsegmental associated with segmental vitiligo), focal vitiligo, solitary mucosal vitiligo or vitiligo with or without leukotricia (involvement of body hair) or any type of vitiligo set forth in Table 1 below:

TABLE 1

Classification of vitiligo.

| NOMEN-CLATURE | SUBSET | NOTES |
|---|---|---|
| Non-segmental vitiligo | Acrofacial | Usually limited to face, head, hands, and feet |
| | Generalized | Symmetrical macules, mainly hands, fingers, face, and trauma-exposed areas |
| | Mucosal (at least two sites involved) | Involvement of the oral and/or genital mucosae with other sites of skin involvement |
| | Universal | Depigmentation affects 80%-90% of body surface. |
| Segmental vitiligo | Unisegmental | One or more depigmented macules distributed on one side of the body |
| | Bisegmental | Two segmental lesions distributed either unilaterally or bilaterally |
| | Plurisegmental | Multiple segmental lesions distributed either unilaterally or bi-laterally |
| Mixed vitiligo | Occurrence of SV and NSV | SV followed by NSV with a delay of at least 6 months. At least 20% of a dermatomal segment affected by SV. |
| Unclassified vitiligo | Focal vitiligo | Isolated macules that do not have a segmental distribution. No evolution into NSV after at least 2 years |
| | Mucosal vitiligo (only one site involved) | Exclusive involvement of the oral or genital mucosae |

In an embodiment, said skin disorder is atopic dermatitis, psoriasis, psoriasis vulgaris, skin sensitization, skin irritation, skin rash, contact dermatitis, allergic contact sensitization, allergic dermatitis, inflammatory dermatoses, or neutrophilic dermatoses.

"Pruritus", as used herein, is interchangeable with "itch." In some embodiments, pruritus includes chronic idiopathic pruritus, as well as pruritic components of other pruritic disorders. In some embodiments, pruritus may be a symptom of a disease or condition selected from the group consisting of: allergic reaction, arthropod bites, athlete's foot, atopic dermatitis (AD), atopic itch, atopic dermatitis-associated itch, autoimmune responses, autoimmune connective tissue disease, bacterial infection, biliary itch, broad activation of the immune responses, body louse, bullous diseases, brachioradial pruritus, brain tumors, chronic idiopathic pruritus, contact dermatitis, cholestasis, cutaneous larva migrans, cutaneous T-cell lymphoma, nervous system damage, dandruff, delusional parasitosis, dermatomyositis, dermatosis of pregnancy, diabetes mellitus, drug eruptions, dysregulation of neuronal processes and sensory perception, eczema, eosinophilic folliculitis, foreign objects or devices on skin, fungal infection, gestational pemphigoid, head lice, herpes, hidradenitis suppurativa, hives, Hodgkin's disease, hyperparathyroidism, idiopathic chronic itch, inflammation, insect infestation, insect bites, insect stings, intrahepatic cholestasis of pregnancy, iron deficiency anemia, increased accumulation of exogenous opioids or synthetic opioids, internal cancer, jaundice, lichen planus, lichen sclerosus, lupus erythematosus, lymphoma, lymphoma-associated itch, leukemia-associated itch, malignancy, mastocytosis, menopause, multiple sclerosis, neoplasm, nerve irritation, neurogenic itch, neuropathic itch, notalgia parestheica, notalgia obsessive-compulsive disorders, paresthetica, parasitic infection, popular urticaria, pediculosis, peripheral neuropathy, photodermatitis, polycythemia vera, psychiatric disease, psychogenic itch, pruritic popular eruption of HIV, pruritic urticarial papules and plaques of pregnancy (PUPPP), psoriasis, psoriasis-associated itch, psoriatic itch, pubic lice, punctate palmoplantar keratoderma, renal itch, rheumatoid arthritis, scabies, scar growth, shaving, seborrheic dermatitis, stasis dermatitis, sunburn, swimmer's itch, systemic immune senescence, tactile hallucinations, Th17-associated inflammation, thyroid illness, uremia, pruritus or uremic itch, urticaria, urticarial itch, varicella, viral infection, wound or scab healing, and xerosis.

In an embodiment, the hair loss disorder is selected from alopecia, alopecia areata, patchy alopecia areata, alopecia totalis, alopecia universalis, ophiasis pattern alopecia areata, sisaihpo pattern alopecia areata, androgenetic alopecia (male and female pattern hair loss), telogen effluvium, tinea capitis, hypotrichosis, hereditary hypotrichosis simplex, scarring alopecia, lichen planopilaris, central centrifugal cicatricial alopecia, folliculitis decalvans, or frontal fibrosing alopecia.

In an embodiment, the connective tissue disease is selected from SLE (systemic lupus erythematosus), cutaneous lupus (e.g. SCLE, discoid lupus), chilblain lupus erythematosus, myositis, polymyositis, dermatomyositis, scleroderma, Sjogren's syndrome, polychondritis (relapsing polychondritis), vasculitis, or large vessel vasculitis.

In an embodiment, the nephropathy is selected from an immunologically mediated nephropathy, autoimmune nephropathy, chronic progressive nephropathies, diabetic nephropathy, renal fibrosis, ischemic/reperfusion injury associated, HIV associated nephropathy, ureteral obstructive nephropathy, glomerulosclerosis, proteinuria, nephrotic syndrome, polycystic kidney disease, autosomal dominant polycystic kidney disease or diabetic kidney disease.

In an embodiment, said cancer is a solid tumor.

In an embodiment, said cancer is prostate cancer, renal cancer, hepatic cancer, breast cancer, lung cancer, thyroid cancer, Kaposi's sarcoma, Castleman's disease or pancreatic cancer.

In an embodiment, said cancer is lymphoma, leukemia, or multiple myeloma.

In an embodiment, said myeloproliferative disorder (MPD) is polycythemia vera (PV), essential thrombocythemia (ET), myeloid metaplasia with myelofibrosis (MMM), primary myelofibrosis (PMF), chronic myelogenous leukemia (CML), chronic myelomonocytic leukemia (CMML), hypereosinophilic syndrome (HES), idiopathic myelofibrosis (IMF), or systemic mast cell disease (SMCD).

In an embodiment, said myeloproliferative disorder is myelofibrosis.

In an embodiment, said myeloproliferative disorder is primary myelofibrosis (PMF).

In some embodiments, the p38 MAP Kinase-mediated disease or disorder is a cancer, prostate cancer, renal cancer, hepatic cancer, breast cancer, lung cancer, thyroid cancer, Kaposi's sarcoma, Castleman's disease, pancreatic cancer, lymphoma, leukemia, multiple myeloma, neoplasia, primary malignancies, secondary or recurrent malignancies, metastatic malignancies, angiogenesis disorders, acute lymphocytic leukemia, acute and chronic myelogenous leukemia, chronic lymphocytic leukemia, acute lymphoblastic leukemia, promyelocytic leukemia, B-cell lymphoma, T-cell lymphoma, mantle cell lymphoma, hairy cell lymphoma, Burkitt's lymphoma, mast cell tumors, Hodgkin's disease or non-Hodgkin's disease, myelodysplastic syndrome, sarcoma, fibrosarcoma, rhabdomyosarcoma; astrocytoma, neuroblastoma, glioma, schwannoma, non-melanoma skin cancers, squamous cell carcinoma, basal cell carcinoma, Merkel cell carcinoma, seminoma, teratocarcinoma, osteosarcoma, xeroderma pigmentosum, keratoacanthoma, thyroid follicular cancer, melanoma, teratoma, rhabdomyosarcoma, metastatic and bone disorders, glioblastoma multiforme, a malignancy, a myeloproliferative disorder, a hematopoietic neoplasm, a myeloid neoplasm, a lymphoid neoplasm, myelofibrosis, primary myelofibrosis, polycythemia vera, essential thrombocythemia, acute and chronic leukemias, lymphomas, cutaneous lymphomas, mycosis fungoides, other myeloid malignancies, myelodysplastic syndrome, myeloproliferative disorder, polycythemia vera, essential thrombocythemia, myeloid metaplasia with myelofibrosis, primary myelofibrosis, chronic myelogenous leukemia (CML), chronic myelomonocytic leukemia, hypereosinophilic syndrome, idiopathic myelofibrosis (IMF), systemic mast cell disease, and a combination thereof.

In an embodiment, said bone resorption disease is osteoporosis, osteoarthritis, bone resorption associated with hormonal imbalance, bone resorption associated with hormonal therapy, bone resorption associated with autoimmune disease, or bone resorption associated with cancer.

In some embodiments, the p38 MAP Kinase mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis), radiation induced fibrosis (for example, head and neck, gastrointestinal or pulmonary), primary sclerosing cholangitis, restenosis, cardiac fibrosis (for example, endomyocardial fibrosis or atrial fibrosis), ophthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the p38 MAP Kinase mediated disease or disorder is a metabolic disorder. Exemplary metabolic disorders include obesity, steroid-resistance, glucose intolerance, and metabolic syndrome. In some embodiments, the p38 MAP Kinase mediated disease or disorder is a neoplasia. Exemplary neoplasias include cancers. In some embodiments the neoplasms include primary malignancies, secondary or recurrent malignancies, or metastatic malignancies. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, sarcoma, fibrosarcoma, rhabdomyosarcoma; astrocytoma, neuroblastoma, glioma and schwannomas; melanoma, non-melanoma skin cancers, (e.g. squamous cell carcinoma, basal cell carcinoma, Merkel cell carcinoma), seminoma, teratocarcinoma, osteosarcoma, xeroderma pigmentosum, keratoacanthoma, thyroid follicular cancer, Kaposi's sarcoma, melanoma, teratoma, rhabdomyosarcoma, metastatic and bone disorders, as well as cancer of the bone, mouth/ pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the p38 MAP Kinase mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

Also provided herein is a compound as disclosed herein for use as a medicament.

Also provided herein is a compound as disclosed herein for use as a medicament for the treatment of a p38 MAP Kinase mediated disease.

Also provided is the use of a compound as disclosed herein as a medicament.

Also provided is the use of a compound as disclosed herein as a medicament for the treatment of a p38 MAP Kinase mediated disease.

Also provided is a compound as disclosed herein for use in the manufacture of a medicament for the treatment of a p38 MAP Kinase mediated disease.

Also provided is the use of a compound as disclosed herein for the treatment of a p38 MAP Kinase mediated disease.

Also provided herein is a method of inhibition of p38 MAP Kinase comprising contacting p38 MAP Kinase with a compound as disclosed herein, or a derivative thereof.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the p38 MAP Kinase mediated disease is chosen from pruritus, alopecia, alopecia areata, vitiligo, male pattern androgenetic alopecia, female pattern androgenetic alopecia, atopic dermatitis, rheumatoid arthritis, psoriatic arthritis, and psoriasis.

The compounds can be administered in various modes, e.g. oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration. The specific dose level for any particular patient will depend upon a variety of factors including the activity of the specific compound employed, the age, body weight, general health, sex, diet, time of administration, route of administration, rate of excretion, drug combination, the precise disorder being treated, and the severity of the indication or condition being treated. Also, the route of administration may vary depending on the condition and its severity.

In certain embodiments, a topically or orally administered p38 MAP Kinase inhibitor/antagonist described herein can be used for the treatment of alopecia areata (e.g., patchy alopecia areata, alopecia totalis, alopecia universalis) alone or in combination with topical or intralesional corticosteroids, topical minoxidil, oral minoxidil, topical or systemic antiandrogens, oral finasteride, oral dutasteride, topical or oral cortexolone 17α-propionate, ketoconazole, spionolactone, prostaglandin F2 analogues (e.g. bimatoprost or latanoprost), contact sensitization therapy such as with squaric acid dibutyl ester, dinitrochlorobenzene, diphencyprone, topical or oral methoxalen and ultraviolet a (PUVA), topical anthralin, hair transplantation procedures, microneedling, low level laser light therapy, low level non-laser light therapy, platelet-rich plasma (PRP) therapy or other therapies known to have beneficial effects in the condition.

In certain embodiments, a topically or orally administered p38 MAP Kinase inhibitor/antagonist disclosed herein can be used for the treatment of male or female-pattern baldness (androgenetic alopecia) alone or in combination with topical minoxidil, oral minoxidil, topical or systemic antiandrogens, oral finasteride, oral dutasteride, topical or oral cortexolone 17α-propionate, ketoconazole, spionolactone, prostaglandin F2 analogues (e.g. bimatoprost or latanoprost), contact sensitization therapy such as with squaric acid dibutyl ester, dinitrochlorobenzene, diphencyprone, topical or oral methoxalen and ultraviolet a (PUVA), topical anthralin, hair transplantation procedures, microneedling, low level laser light therapy, low level non-laser light therapy, platelet-rich plasma (PRP) therapy or other therapies known to have beneficial effects in the condition.

In certain embodiments, a topically or orally administered p38 MAP Kinase inhibitor/antagonist disclosed herein can be used for the treatment of scarring alopecia (e.g., cicatricial alopecia, central centrifugal cicatricial alopecia, lichen planopilaris, frontal fibrosing alopecia, folliculitis decalvans) alone or in combination with topical minoxidil, oral minoxidil, topical or systemic antiandrogens, oral finasteride, oral dutasteride, topical or oral cortexolone 17α-propionate, ketoconazole, spionolactone, prostaglandin F2 analogues (e.g. bimatoprost or latanoprost), contact sensitization therapy such as with squaric acid dibutyl ester, dinitrochlorobenzene, diphencyprone, topical or oral methoxalen and ultraviolet a (PUVA), topical anthralin, hair transplantation procedures, microneedling, low level laser light therapy, low level non-laser light therapy, platelet-rich plasma (PRP) therapy or other therapies known to have beneficial effects in the condition.

In certain embodiments, the compounds may be used for the treatment of vitiligo (e.g., localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, or universal vitiligo) alone or in combination with topical corticosteroids, topical tacrolimus, topical pimecrolimus, phototherapy such as ultraviolet light therapy with UVB, narrow-band UVB, oral or topical psoralen plus ultraviolet A (PUVA), calcipotriene or other topical vitamin D analogs, excimer laser phototherapy, systemic immunosuppressive agents, surgical treatments such as skin minigrafting, transplantation of autologous epidermal suspension, camouflage such as with make-up or dihydroxyacetone and such, or other therapies known to have beneficial effects in the condition.

Specific p38 MAP Kinase mediated diseases to be treated by the compounds, compositions, and methods disclosed herein include a skin disorder, pruritus, cancer, Alzheimer's disease, an inflammatory condition, and an autoimmune condition.

In an embodiment, said skin disorder is pruritus, atopic dermatitis, psoriasis, acne vulgaris, comedonal acne, inflammatory acne, nodulo-cystic acne, scarring acne, hidradenitis suppurativa, pyoderma gangrenosum, skin sensitization, skin irritation, skin rash, contact dermatitis or allergic contact sensitization.

Besides being useful for human treatment, certain compounds and compositions disclosed herein may also be useful for veterinary treatment of companion animals, exotic animals and farm animals, including mammals, rodents, and the like. More preferred animals include horses, dogs, and cats.

Combination Therapy

The compounds and pharmaceutical compositions of the present disclosure may be used to prevent or treat an p38 MAP Kinase mediated disorder by the sequential or co-administration of another pharmaceutical agent.

The compounds of the present invention can be used, alone or in combination with other pharmaceutically active compounds, to treat conditions such as those previously described above. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In certain instances, it may be appropriate to administer at least one of the compounds described herein, or a derivative thereof, in combination with another pharmaceutical agent. By way of example only, if one of the side effects experienced by a patient upon receiving one of the compounds herein is hypertension, then it may be appropriate to administer an anti-hypertensive agent in combination with the initial pharmaceutical agent. Or, by way of example only, the therapeutic effectiveness of one of the compounds described herein may be enhanced by administration of an adjuvant (i.e., by itself the adjuvant may only have minimal therapeutic benefit, but in combination with another pharmaceutical agent, the overall therapeutic benefit to the patient is enhanced). Or, by way of example only, the benefit of experienced by a patient may be increased by administering one of the compounds described herein with another pharmaceutical agent (which also includes a therapeutic regimen) that also has therapeutic benefit. By way of example only, in a treatment for diabetes involving administration of one of the compounds described herein, increased therapeutic benefit may result by also providing the patient with another pharmaceutical agent for diabetes. In any case, regardless of the disease, disorder or condition being treated, the overall benefit experienced by the patient may simply be additive of the two pharmaceutical agents or the patient may experience a synergistic benefit.

Specific, non-limiting examples of possible combination therapies include use of compounds of embodiments herein with: chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

Specific, non-limiting examples of possible combination therapies for inflammation include use of certain compounds of the disclosure with: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON™), flurbiprofen (AN-SAID™) ketoprofen, oxaprozin (DAYPRO™), diclofenac sodium (VOLTAREN™), diclofenac potassium (CATAFLAM™), etodolac (LODINE™), indomethacin (INDOCIN™), ketorolac (TORADOL™), sulindac (CLINORIL™), tolmetin (TOLECTIN™), meclofenamate (MECLOMEN™), mefenamic acid (PONSTEL™), nabumetone (RELAFEN™) and piroxicam (FELDENE™); (3) immunosuppressants, including but not limited to methotrexate (RHEUMATREX™), leflunomide (ARAVA™), azathioprine (IMURAN™) cyclosporine (NEORAL™, SANDIMMUNE™), tacrolimus and cyclophosphamide (CYTOXAN™); (4) CD20 blockers, including but not limited to rituximab (RITUXAN™); (5) Tumor Necrosis Factor (TNF) blockers, including but not limited to etanercept (ENBREL™), infliximab (REMICADE™) and adalimumab (HUMIRA™); (6) interleukin-1 receptor antagonists, including but not limited to anakinra (KINERET™); (7) interleukin-6 inhibitors, including but not limited to tocilizumab (ACTEMRA™); (8) interleukin-17 inhibitors, including but not limited to AIN457; (9) Janus kinase inhibitors, including but not limited to tasocitinib; and (10) syk inhibitors, including but not limited to fostamatinib.

Specific, non-limiting examples of possible combination therapies for the treatment of cancer include use of certain compounds of the disclosure with: (1) alkylating agents, including but not limited to cisplatin (PLATIN™), carboplatin (PARAPLATIN™) oxaliplatin (ELOXATIN™), streptozocin (ZANOSAR™), busulfan (MYLERAN™) and cyclophosphamide (ENDOXAN™); (2) anti-metabolites, including but not limited to mercaptopurine (PURINETHOL™), thioguanine, pentostatin (NIPENT™), cytosine arabinoside (ARA-C™), gemcitabine (GEMZAR™), fluorouracil (CARAC™), leucovorin (FUSILEV™) and methotrexate (RHEUMATREX™); (3) plant alkaloids and terpenoids, including but not limited to vincristine (ONCOVIN™), vinblastine and paclitaxel (TAXOL™); (4) topoisomerase inhibitors, including but not limited to irinotecan (CAMPTOSAR™), topotecan (HYCAMTIN™) and etoposide (EPOSIN™); (5) cytotoxic antibiotics, including but not limited to actinomycin D (COSMEGEN™), doxorubicin (ADRIAMYCIN™), bleomycin (BLENOXANE™) and mitomycin (MITOSOL™); (6) angiogenesis inhibitors, including but not limited to sunitinib (SUTENT™) and bevacizumab (AVASTIN™); (7) tyrosine kinase inhibitors, including but not limited to imatinib (GLEEVEC™), erlotinib (TARCEVA™), lapatininb (TYKERB™) and axitinib (INLYTA™); and (8) immune checkpoint inhibitors, including but not limited to atezolizumab (TECENTRIQ™), avelumab (BAVENCIO™), durvalumab (IMFINZI™), ipilimumab (YERVOY™), pembrolizumab (KEYTRUDA™), nivolumab (OPDIVO™), and tremelimumab.

In an embodiment, said composition further comprises an additional pharmaceutical agent selected from a chemotherapeutic or anti-proliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, an agent for treating immunodeficiency disorders, and immune checkpoint inhibitors. Compounds and pharmaceutically acceptable compositions of the present disclosure can be employed in combination therapies, that is, the compounds and pharmaceutically acceptable compositions may have potential utility in combination with other therapies for the treatment of immune, inflammatory, proliferative, and allergic disorders. Examples include, but not limited, to co-administration with steroids, leukotriene antagonists, anti-histamines, anti-cancer agents, protein kinase inhibitors, cyclosporine, rapamycin, or immune checkpoint inhibitors.

Cancer cells often use immune checkpoint molecules to evade or suppress attack by the immune system. Thus, expression of immune checkpoint molecules on the surface of cancers cells prevents immune cells such as T cells from recognizing them as "foreign" or "abnormal." Consequently, immune checkpoint inhibitors are compounds which block inhibitory immune checkpoint molecules leading to the activation of the immune system via T cell recognition.

Inhibitory checkpoint molecules have been increasingly considered as new targets for cancer immunotherapies due to the effectiveness of two checkpoint inhibitor drugs that were initially indicated for advanced melanoma-ipilimumab (e.g. YERVOY™; a monoclonal antibody that works to activate the immune system by targeting CTLA-4), and pembrolizumab (e.g. KEYTRUDA™; a humanized antibody that targets the programmed cell death 1 (PD-1) receptor). Another checkpoint inhibitor known as nivolumab (e.g. OPDIVO™) blocks the interaction between PD-1 and programmed cell death ligand 1 (PD-L1) which prevents inhibition of an immune.

Any molecule capable of inhibiting one or more immune checkpoint molecules can be used in the methods disclosed herein as an additional pharmaceutical agent. Such immune checkpoint inhibitors include, without limitation, antibodies or functional fragments thereof, inhibitory polypeptides, small molecule chemical compounds, and/or inhibitory nucleic acids (such as, but not limited to, antisense oligonucleotides, small inhibitory RNAs (siRNAs), small hairpin RNAs (shRNAs), and/or catalytic nucleic acids such as ribozymes). Immune checkpoint molecules suitable for targeting by checkpoint inhibitors for use in any of the methods disclosed herein include, without limitation, one or more of the adenosine $A_{2A}$ receptor (A2AR), B7-H3 (a.k.a. CD276; e.g., MGA271), cytotoxic T-lymphocyte-associated protein 4 (CTLA4; a.k.a. CD152; e.g., ipilimumab; AGEN-1884 (Agenus), programmed cell death ligand 1 (PD-L1; a.k.a. CD274; e.g., MDX-1105 (Bristol Myers Squibb), WBP-3155 (C-stone), LY3300054 (Eli Lilly)), programmed cell death protein 1 (PD-1; a.k.a. CD279; e.g., pembrolizumab, SHR-1210 (Incyte), STI-A1110 (Sorrento), REGN2810 (Regeneron), CT-011 (pidilizumab; Curetech), PDR-001 (Novartis), BGB-A317 (BeiGene), TSR-042 (Tesaro), ENUMC-8 (Enumeral), MGD-013 (Macrogenics; bispecific antibody for PD1 and Lag3), B7-H4 (a.k.a. VTCN1), T-cell immunoglobulin and mucin-domain containing-3 (TIM3; a.k.a. HAVCR2), B and T Lymphocyte Attenuator (BTLA; a.k.a. CD272), indoleamine-pyrrole 2,3-dioxygenase (IDO), killer-cell immunoglobulin-like receptors (KIRs; e.g., lirilumab), lymphocyte-activation gene 3 (LAG-3; e.g., BMS-986016), T cell immunoreceptor with Ig and ITIM domains (TIGIT; a.k.a. WUCAM and Vstm3), ILT-3, ILT-4, and/or V-domain Ig suppressor of T cell activation (VISTA).

In some embodiments, the immune checkpoint inhibitor is an antagonistic antibody, such as, but not limited to, one or more of ipilimumab (Bristol-Myers Squibb), nivolumab (Bristol-Myers Squibb), Pembrolizumab (Merck) durvalumab (Medimmune), atezolizumab (Genentech/Roche), tremelimumab (Medimmune), and/or avelumab (Pfizer).

The compounds and pharmaceutical compositions of the present disclosure may be used to prevent or treat a JAK1 and/or JAK3-mediated disease by the sequential or co-administration of another pharmaceutical agent.

In some embodiments, the compounds disclosed in embodiments herein can also be co-administered (concurrently or sequentially) with a variety of other pharmaceutical agents or treatments, for example, pharmaceutical agents or treatments that are administered systemically, such as orally or parenterally. Examples of such systemic treatments include topical or systemic corticosteroids (such as prednisone), antibiotics (such as erythromycin, tetracycline, and dicloxacillin), antifungal agents (such as ketoconazole and fluconazole sold under the tradename Diflucan™), antiviral agents (such as valacyclovir sold under the tradename Valtrex™, acyclovir, and famciclovir sold under the tradename Famvir™) corticosteroids, immunosuppressants (such as cyclophosphamide sold under the tradename Cytoxan™, azathioprine, methotrexate, mycophenolate), biologics (such as rituximab sold under the tradename Rituxan™, etanercept sold under the tradename Enbrel™, adalimumab sold under the tradename Humira™, infliximab sold under the tradename Remicade™ ustekinumab sold under the tradename Stelara™, and alefacept sold under the tradename Amevive™), and/or thyroid hormone replacement.

In some embodiments, other therapies that can be used in combination with the compounds disclosed herein include, for example, mercaptopurine, topical or systemic corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil, azathioprine, various antibodies, for example, anti-lymphocyte globulin (ALG), antithymocyte globulin (ATG), monoclonal anti-T-cell antibodies (OKT3), and irradiation. These various agents can be used in accordance with their standard or common dosages, as specified in the prescribing information accompanying commercially available forms of the drugs (see also, the prescribing information in the 2006 Edition of The Physician's Desk Reference). In some embodiments, standard dosages of these agents may be reduced when used in combination with the compounds of embodiments herein. Without limiting the scope of this disclosure, it is believed the such combination may result in synergistic results with better efficacy, less toxicity, longer duration of action, or quicker response to therapy. In some embodiments, the combination therapies in embodiments herein may be administered in sub-therapeutic amounts of either the compounds of embodiments herein or the additional pharmaceutical agents, or both. Azathioprine is currently available from Salix Pharmaceuticals, Inc. under the brand name Azasan™; mercaptopurine is currently available from Gate Pharmaceuticals, Inc. under the brand name Purinethol™; prednisone and prednisolone are currently available from Roxane Laboratories, Inc.; methyl prednisolone is currently available from Pfizer; sirolimus (rapamycin) is currently available from Wyeth-Ayerst under the brand name Rapamune™; tacrolimus is currently available from Fujisawa under the brand name Prograf™; cyclosporine is current available from Novartis under the brand name Sandimmune™ and Abbott under the brand name Gengraf™; IMPDH inhibitors such as mycophenolate mofetil and mycophenolic acid are currently available from Roche under the brand name Cellcept™ and Novartis under the brand name Myfortic™; azathioprine is currently available from Glaxo Smith Kline under the brand name Imuran™; and antibodies are currently available from Ortho Biotech under the brand name Orthoclone™, Novartis under the brand name Simulect™ (basiliximab) and Roche under the brand name Zenapax™ (daclizumab).

In some embodiments, the compounds of embodiments herein are administered in conjunction, concomitantly or adjunctively, with the pharmaceutical agents or therapies above and/or with a pharmaceutical agent or therapy for another disease. For example, the compounds of embodiments herein may be combined with thyroid hormone replacement therapy or with anti-inflammatory or immunomodulatory therapies.

In some embodiments, the combination therapies in embodiments herein may be administered in sub-therapeutic amounts of either the compounds of embodiments herein or the additional pharmaceutical agents, or both.

For use in cancer and neoplastic diseases a p38 MAP Kinase inhibitor is optimally used together with one or more of the following classes of drugs: wherein the anti-cancer agent is an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-IR antibody, NFkB inhibitor, proteosome inhibitor, chemotherapy agent, or glucose reduction agent.

In any case, the multiple pharmaceutical agents (at least one of which is a compound disclosed herein) may be administered in any order or even simultaneously. If simultaneously, the multiple pharmaceutical agents may be provided in a single, unified form, or in multiple forms (by way of example only, either as a single pill or as two separate pills). One of the pharmaceutical agents may be given in multiple doses, or both may be given as multiple doses. If not simultaneous, the timing between the multiple doses may be any duration of time ranging from a few minutes to eight weeks or at any interval appropriate to maintain the desired therapeutic efficacy. In some embodiments, the timing between the multiple doses may be a minute, an hour, six hours, a day, two days, three days, four days, five days, six days, a week, two weeks, three weeks, four weeks, five weeks, six weeks, seven weeks or eight weeks.

Thus, in another aspect, certain embodiments provide methods for treating p38 MAP Kinase mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of p38 MAP Kinase-mediated disorders.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-inflammatory drugs, anti-atherosclerotic drugs, immunosuppressive drugs, immunomodulatory drugs, cytostatic drugs, anti-proliferative agents, angiogenesis inhibitors, kinase inhibitors, cytokine blockers and inhibitors of cell adhesion molecules.

In another embodiment, the pharmaceutical compositions can further include one or more additional pharmaceutical agents such as a chemotherapeutic, steroid, anti-inflammatory compound, or immunosuppressant.

p38 MAP Kinase inhibitor compositions described herein are also optionally used in combination with other therapeutic reagents that are selected for their therapeutic value for the condition to be treated In general, the pharmaceutical compositions described herein and, in embodiments where combinational therapy is employed, other agents do not have to be administered in the same pharmaceutical composition, and, because of different physical and chemical characteristics, are optionally administered by different routes. The initial administration is generally made according to established protocols, and then, based upon the observed effects, the dosage, modes of administration and times of administration subsequently modified. In certain instances, it is appropriate to administer a p38 MAP Kinase inhibitor composition as described herein in combination with another therapeutic agent. By way of example only, if one of the side effects experienced by a patient upon receiving a p38 MAP Kinase inhibitor composition as described herein is rash, then it is appropriate to administer an anti-histamine agent in combination with the initial therapeutic agent. Or, by way of example only, the therapeutic effectiveness of a p38 MAP Kinase inhibitor is enhanced by administration of another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a synergistic benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a p38 MAP Kinase inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods and compositions are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

In another embodiment, a p38 MAP Kinase inhibitor is optionally used in combination with procedures that provide additional or synergistic benefit to the patient. A p38 MAP Kinase inhibitor and the additional therapy(ies) are optionally administered before, during or after the occurrence of a disease or condition, and the timing of administering the pharmaceutical composition containing a p38 MAP Kinase inhibitor varies in some embodiments. Thus, for example, a p38 MAP Kinase inhibitor is used as a prophylactic and is administered continuously to subjects with a propensity to develop conditions or diseases in order to prevent the occurrence of the disease or condition. A p38 MAP Kinase inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A p38 MAP Kinase inhibitor may be used in combination with drugs from the following classes: NSAIDs, immunosuppressive drugs, immunomodulatory drugs, cytostatic drugs, anti-proliferative agents, angiogenesis inhibitors, biological agents, steroids, vitamin D3 analogs, retinoids, other kinase inhibitors, cytokine blockers, corticosteroids and inhibitors of cell adhesion molecules. Where a subject is suffering from or at risk of suffering from atherosclerosis or a condition that is associated with atherosclerosis, a p38 MAP Kinase inhibitor composition described herein is optionally used together with one or more agents or methods for treating atherosclerosis or a condition that is associated with atherosclerosis in any combination. Examples of therapeutic agents/treatments for treating atherosclerosis or a condition that is associated with atherosclerosis include, but are not limited to any of the following: torcetrapib, aspirin, niacin, HMG CoA reductase inhibitors (e.g., atorvastatin, fluvastatin, lovastatin, pravastatin, rosuvastatin and simvastatin), colesevelam, cholestyramine, colestipol, gemfibrozil, probucol and clofibrate.)

Where a subject is suffering from or at risk of suffering from an inflammatory condition, a p38 MAP Kinase inhibitor composition described herein is optionally used together with one or more agents or methods for treating an inflammatory condition in any combination.

In certain embodiments, the additional pharmaceutical agent is selected from taxanes, inhibitors of bcr-abl, inhibitors of EGFR, DNA damaging agents, antimetabolites, paclitaxel, imatinib, dasatinib, nilotinib, erlotinib, gefitinib, cisplatin, oxaliplatin, carboplatin, anthracyclines, AraC, 5-FU, camptothecin, doxorubicin, idarubicin, paclitaxel, docetaxel, vincristine, a MEK inhibitor, U0126, a KSP inhibitor, vorinostat, pembrolizumab, nivolumab, atezolizumab, avelumab, tremelimumab, and durvalumab.

In some embodiments, said composition further comprises an additional pharmaceutical agent selected from a chemotherapeutic or anti-proliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, and an agent for treating immunodeficiency disorders.

In some embodiments, one or more compounds of the embodiments herein can be used in combination with one or more other therapeutics used in the treatment of p38 MAP Kinase mediated disorders, and may improve the treatment response as compared to the response to the other therapeutics alone, without exacerbation of its toxic effects. In some embodiments, compounds of embodiments herein can be used in combination with one or more JAK1 and/or JAK3 inhibitors and/or JAK2 inhibitors and/or TYK2 inhibitors for the treatment of p38 MAP Kinase mediated disorders. Additive or synergistic effects are desirable outcomes of such combinations. The additional agents can be combined with the present compounds in a single or continuous dosage form, or the agents can be administered simultaneously or sequentially as separate dosage forms. In some embodiments, one or more additional agents can be administered to a patient in combination with at least one p38 MAP Kinase inhibitor/antagonist described herein where the additional agents are administered intermittently as opposed to continuously.

For example, in certain embodiments, a topically or orally administered JAK1 and/or JAK3 inhibitor/antagonist can be administered with a p38 MAP Kinase inhibitory compound as described herein for the treatment of alopecia areata (e.g. patchy alopecia areata, alopecia totalis, alopecia universalis) alone or in combination with topical or intralesional corticosteroids, topical minoxidil, oral finasteride, oral dutasteride, contact sensitization therapy such as with squaric acid dibutyl ester, dinitrochlorobenzene, diphencyprone, topical or oral methoxalen and ultraviolet a (PUVA), topical anthralin, hair transplantation procedures, or other therapies known to have beneficial effects in the condition.

For example, in certain embodiments, a topically or orally administered JAK1 and/or JAK3 inhibitor/antagonist can be administered in combination with a p38 MAP kinase inhibitory compound as disclosed herein for the treatment of male or female-pattern baldness (androgenetic alopecia) alone or in combination with topical minoxidil, oral finasteride (in male), oral dutasteride (in male), topical antiandrogens, hair transplantation procedures, or other therapies known to have beneficial effects in the condition.

For example, in certain embodiments, the compounds can be used for the treatment of vitiligo (e.g. localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, or universal vitiligo) alone or in combination with topical corticosteroids, topical tacrolimus, topical pimecrolimus, phototherapy such as ultraviolet light therapy with UVB, narrow-band UVB, oral or topical psoralen plus ultraviolet A (PUVA), calcipotriene or other topical vitamin D analogs, excimer laser phototherapy, systemic immunosuppressive agents, surgical treatments such as skin minigrafting, transplantation of autologous epidermal suspension, camouflage such as with make-up or dihydroxyacetone and such, or other therapies known to have beneficial effects in the condition.

In certain embodiments the compounds of the disclosure may be used in combination with one or more agents which act by the same mechanism or by different mechanisms to effect treatment of gastrointestinal disorders. The different agents may be administered sequentially or simultaneously (in separate compositions or in the same composition). Useful classes of agents for combination therapy include, but are not limited to, aminosalicylates, steroids, systemic immunosuppressants, anti-TNFα antibodies, TNF alpha ligand inhibitor, TNF binding agent, anti-VLA-4 antibodies, anti-integrin Cv37 antibodies, anti-bacterial agents, Glucocorticoid agonists, Nuclear factor kappa B inhibitors, 5-Lipoxygenase inhibitors, integrin alpha-4/beta-7 antagonist, Cyclooxygenase inhibitors, IL-23 antagonists, Leukotriene BLT receptor antagonist, IL-6 antagonists, IL-8 antagonists, integrin antagonists, nicotinic acetylcholine receptor agonists, PPAR gamma agonists, sphingosine-1-phosphate receptor-1 modulators, B-lymphocyte antigen CD20 inhibitors, calcineurin inhibitors, CD3 antagonist, cell adhesion molecule inhibitors, eosinophil peroxidase inhibitors, heparin agonists, ICAM1 gene inhibitors, IL-13 antagonists, IL-2 receptor alpha subunit inhibitors, insulin sensitizers, interferon beta ligands, interferon gamma receptor antagonists, interleukin-1 beta ligand modulators, MAdCAM inhibitors, PDE 4 inhibitors, sphingosine-1-phosphate receptor-1 agonists, TLR-9 agonists, acetylcholinesterase inhibitors, ACTH receptor agonists, activin receptor antagonists, CCR5 chemokine antagonists, CCR9 chemokine antagonists, and anti-diarrheal medicines.

Aminosalicylates that may be used in combination with the presently disclosed compounds include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin $\alpha_4\beta_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, Gut, 2012, 61, 918-932; Lam et al., *Immunotherapy,* 2014, 6, 963-971.)

Other compounds that may be used in combination with the presently disclosed compounds include, but are not limited to opaganib, abatacept, mongersen, filgotinib, LYC-30937, BI-655130, mirikizumab, adalimumab, tacrolimus, rituximab, GSK-2982772, andecaliximab, naltrexone, risankizumab, QBECO, alicaforsen, etrolizumab, foralumab, ocrelizumab, vedolizumab, amiselimod, ozanimod, dolcanatide, catridecacog, budesonide, STNM-01, cannabidiol, telotristat etiprate, SHP-647, carotegrast methyl, peg-ilodecakin, TOP-1288, iberogast N, PF-06480605, peficitinib, beclomethasone, recombinant interferon beta-1a, infliximab, golimumab, tralokinumab, ustekinumab, certolizumab pegol, thalidomide, upadacitinib, apremilast, natalizumab, interferon beta-1a, rifaximin, RBX-2660, etrasimod, zileuton, fingolimod, cobitolimod, ropivacaine, ABX-464, PF-06700841, prednisolone, GLPG-0974, valganciclovir, ciclosporin, VB-201, tulinercept, MDGN-002, PTG-100, dexamethasone, GED-0507-34-Levo, bertilimumab, brazikumab, KHK-4083, rosiglitazone, mocravimod, sotrastaurin, KAG-308, PUR-0110, E-6007, balsalazide, basiliximab, LP-02, ASP-3291, *Trichuris suis* ova, K(D)PT, midismase, DNVX-078, vatelizumab, alequel, low molecular weight heparin, metenkefalin, tridecactide, HMPL-004, SB-012, olsalazine, balsalazide, propionyl-L-camitine, *Clostridium butyricum*, beclomethasone and acemannan.

General Synthetic Methods for Preparing Compounds

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art. Representative procedures for the preparation of compounds of the invention are outlined in Scheme 1 and 2 below. Solvents and reagents, whose synthetic preparations are not described below, can be purchased at Sigma-Aldrich or Fisher Scientific.

Compounds that are unsubstituted with deuterium were prepared by the following general methods as depicted in Scheme 1.

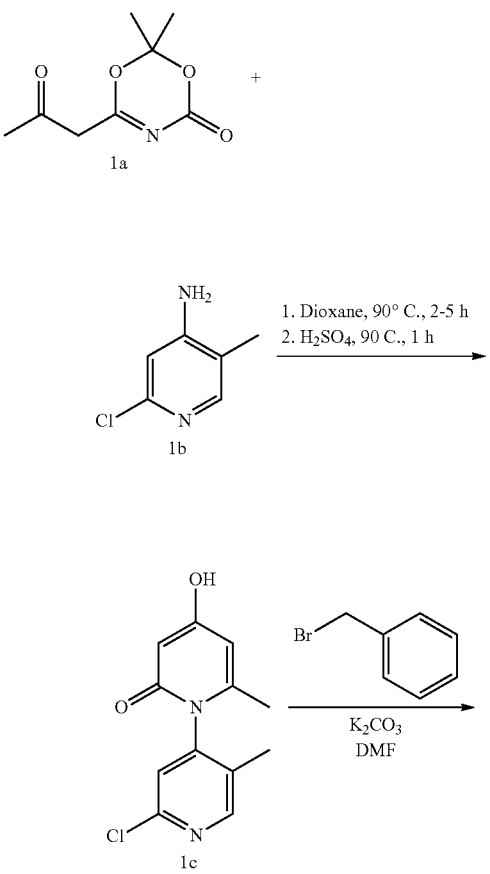

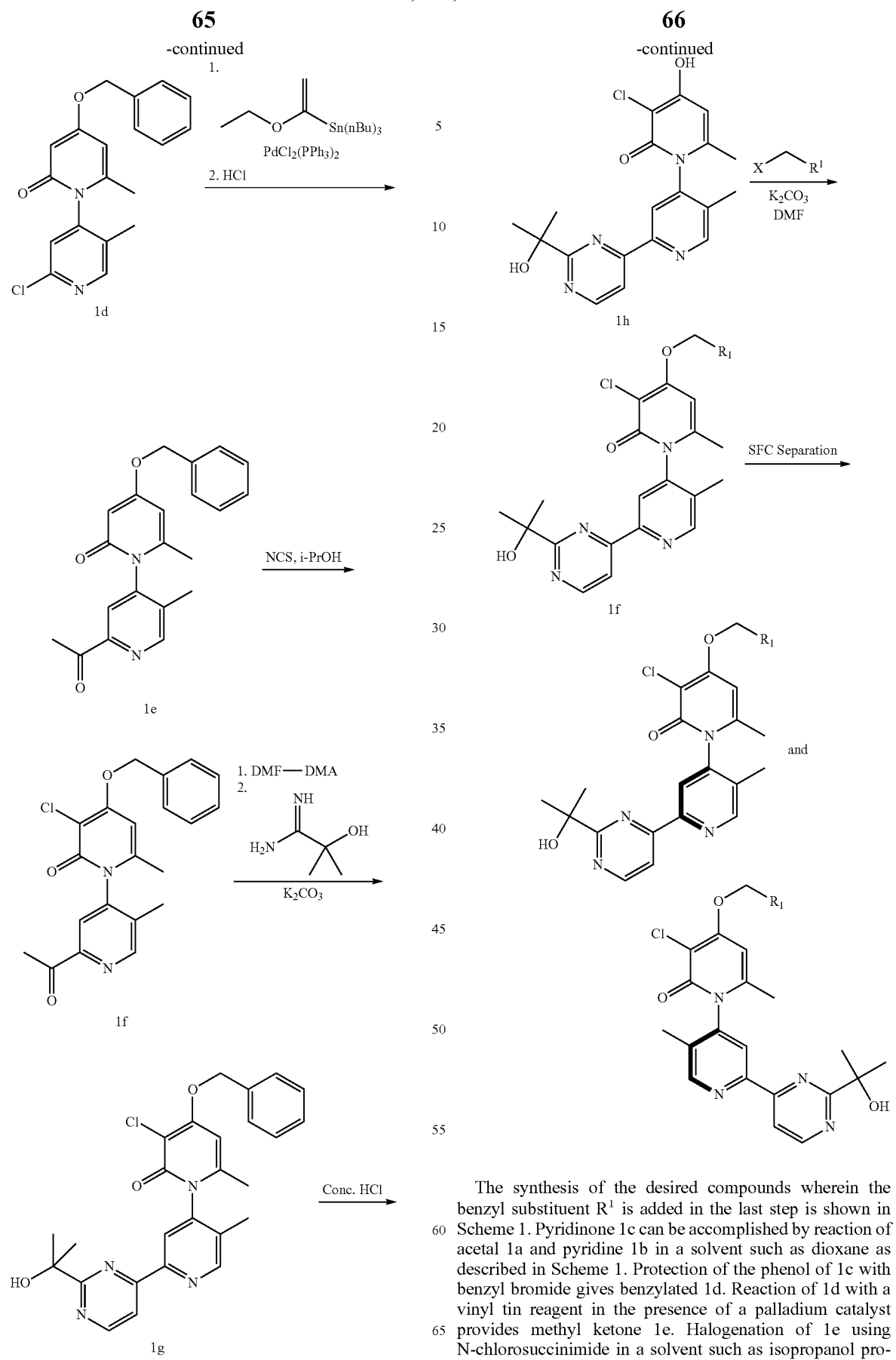

The synthesis of the desired compounds wherein the benzyl substituent $R^1$ is added in the last step is shown in Scheme 1. Pyridinone 1c can be accomplished by reaction of acetal 1a and pyridine 1b in a solvent such as dioxane as described in Scheme 1. Protection of the phenol of 1c with benzyl bromide gives benzylated 1d. Reaction of 1d with a vinyl tin reagent in the presence of a palladium catalyst provides methyl ketone 1e. Halogenation of 1e using N-chlorosuccinimide in a solvent such as isopropanol provides 1f. In situ enamine formation by reaction of if with N,N-dimethylformamide dimethyl acetal provides an intermediate, which is then reacted with 2-hydroxy-2-methyl-propionamidine in a solvent such as DMF to give pyrimidinone 1g. Deprotection of the benzyl group by treating 1g with an acid such as HCl provides 1h. Alkylation of phenol 1h with the desired $R^1CH_2Br$ or $R^1CH_2Cl$ substituent provides the desired pyridinones 1i. Resulting mixtures of atropisomers can be resolved by supercritical fluid chromatography with a mobile phase of carbon dioxide and ethanol.

Isotopic enrichment was determined by mass spectrometry using a Waters Acquity UPLC and SQD mass spectrometer in single ions record mode and the data were analyzed using Empower 3 software (Waters).

Scheme 2 depicts the general synthesis and isolation of compounds of Formula (I) and Formula (II) where A is deuterium.

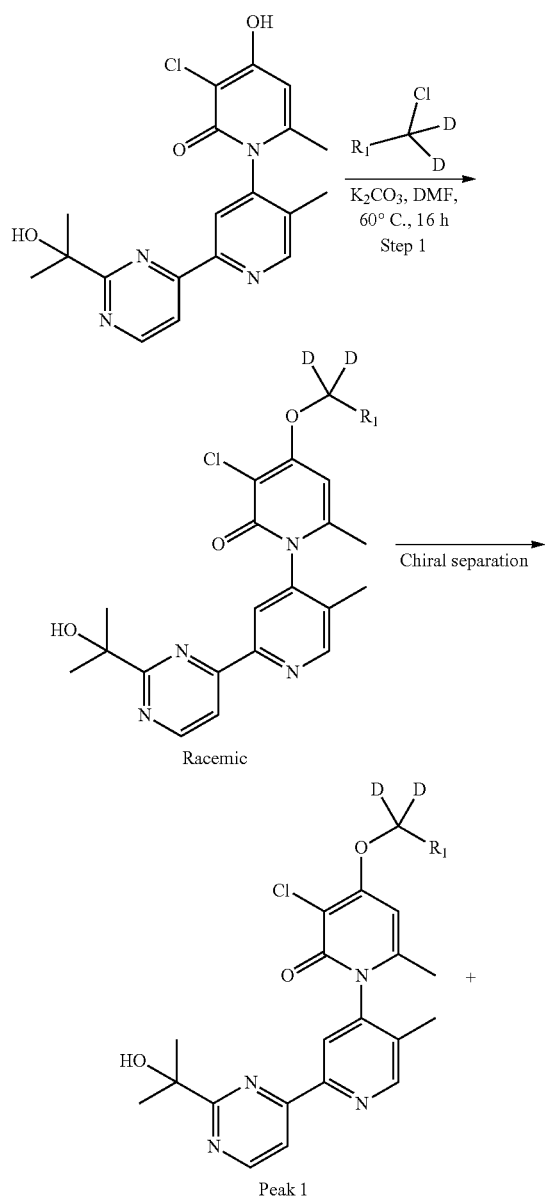

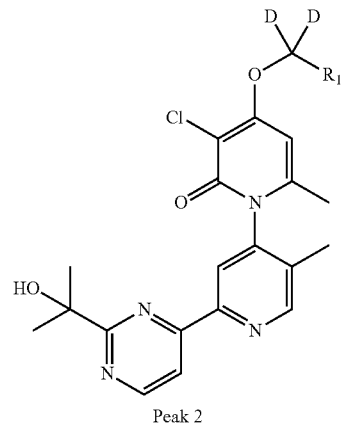

Peak 2

General procedure—A suspension of 3-chloro-4-hydroxy-2'-(2-(2-hydroxypropan-2-yl)pyrimidin-4-yl)-5',6-dimethyl-2H-[1,4'-bipyridin]-2-one (1.0 mmol) and potassium carbonate (3.0 mmol) in N,N-dimethylformamide (20 mmol) was treated with an $d_2$ chlooromethyl arene intermediate (1.2 mmol) was added at ambient temperature and then the mixture was heated to 60° C. for 16 hours. The reaction was cooled to ambient temperature, diluted with ethyl acetate and washed with cold water. The organic layer was washed with brine, dried over anhydrous sodium sulfate, filtered and concentrated in vacuo to provide title compound.

$D_2$ chloromethyl arenes were prepared by similar methods.

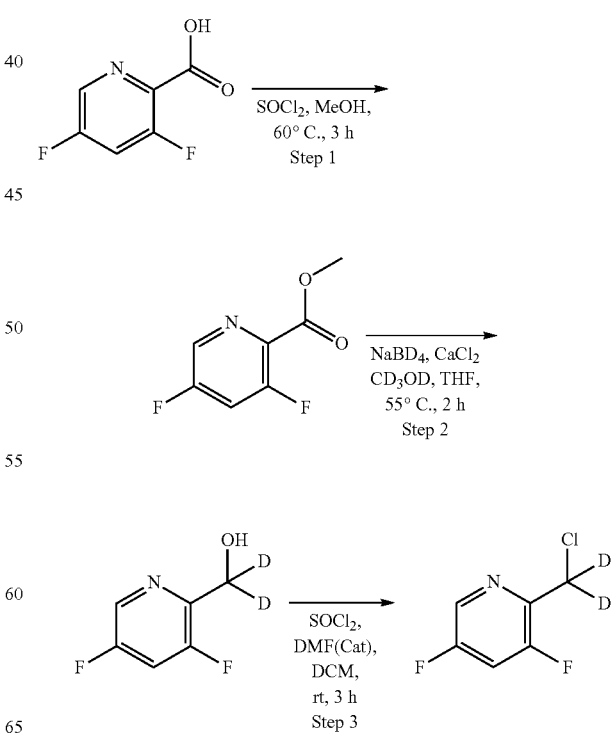

Step 1: Preparation of methyl 3,5-difluoropicolinate

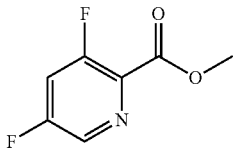

To a solution of 3,5-difluoropicolinic acid (2 g, 12.5 mmol) in methanol (20 mL) was added thionyl chloride (2 mL) at 0° C. and the solution was heated to 60° C. for 3 hours. The reaction mixture was cooled to ambient temperature, concentrated in vacuo to remove volatiles and the residue was quenched with saturated sodium carbonate solution and extracted with ethyl acetate. The organic layer was washed with water, brine, dried over anhydrous sodium sulfate and concentrated in vacuo to provide methyl 3,5-difluoropicolinate as a colorless liquid (1.9 g, crude): MS (ES) m/z 174.1 (M+H).

Step 2: Preparation of (3,5-difluoropyridin-2-yl)methan-$d_2$-ol

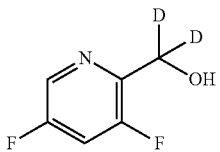

Methyl 3,5-difluoropicolinate (0.5 g, 2.89 mmol) was dissolved into a methan-$d_3$-ol-d: tetrahydrofuran (10 mL: 10 mL) mixture. Sodium borodeuteride (0.36 g, 8.67 mmol, 99 atom % D) and calcium chloride (1.28 g, 11.5 mmol) were added at ambient temperature and the resulting mixture was heated to 55° C. for 2 hours. The reaction mixture was cooled to ambient temperature and diluted with ethyl acetate and filtered through celite. The filtrate was evaporated in vacuo and the residue was quenched with deuterium oxide and extracted with ethyl acetate. The organic layer was washed with water, brine, dried over anhydrous sodium sulfate and concentrated in vacuo to provide (3,5-difluoropyridin-2-yl)methan-$d_2$-ol as a colorless liquid (0.3 g, crude): MS (ES) m/z 148.1 (M+H).

Step 3: Preparation of 2-(chloromethyl-$d_2$)-3,5-difluoropyridine

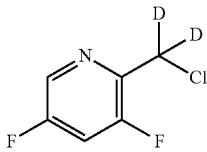

To a stirred solution of (3,5-difluoropyridin-2-yl)methan-$d_2$-ol (0.3 g, 2.04 mmol) in dichloromethane (5 mL), was added thionyl chloride (0.3 mL) and N,N-dimethylformamide (cat.) at 0° C. and the resulting solution was stirred at ambient temperature for 3 hours. The reaction mixture was concentrated in vacuo to provide 2-(chloromethyl-$d_2$)-3,5-difluoropyridine as a liquid (0.3 g, crude): $^1$H NMR (400 MHz, CDCl$_3$) δ 8.34 (s, 1H), 7.22-7.25 (m, 1H).

Scheme 4 Preparation of 3-(chloromethyl-$d_2$)-1-methyl-1H-pyrazole

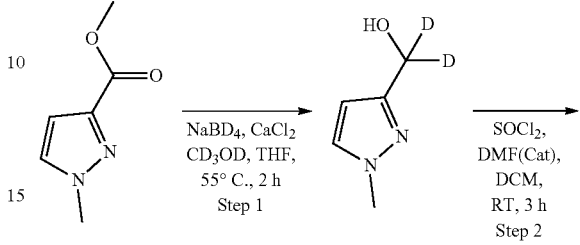

Step 1: Preparation of (1-methyl-1H-pyrazol-3-yl)methan-$d_2$-ol

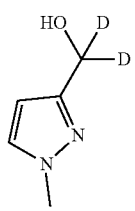

Methyl 1-methyl-1H-pyrazole-3-carboxylate (0.5 g, 3.57 mmol) was added to a mixture of methan-$d_3$-ol-d: tetrahydrofuran (10 mL: 10 mL). Sodium borodeuteride (0.74 g, 17.8 mmol, 99% D) and calcium chloride (1.58 g, 14.2 mmol) were added at ambient temperature and the resulting mixture was heated to 55° C. for 2 hours. The reaction mixture was cooled to ambient temperature, diluted with ethyl acetate and filtered through celite. The filtrate was concentrated in vacuo and the residue was quenched with deuterium oxide and extracted with ethyl acetate. The organic layer was washed with water, brine, dried over anhydrous sodium sulfate and concentrated in vacuo. The crude material obtained was purified by flash chromatography (5% methanol/dichloromethane) provide (1-methyl-1H-pyrazol-3-yl)methan-$d_2$-ol as a colorless liquid (0.4 g, crude): $^1$H NMR (400 MHz, CDCl$_3$) δ 7.31 (s, 1H), 6.21 (s, 1H), 3.89 (s, 3H).

Step 2: Preparation of 3-(chloromethyl-d₂)-1-methyl-1H-pyrazole

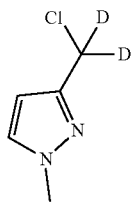

To a solution of (1-methyl-1H-pyrazol-3-yl)methan-d₂-ol (0.4 g, 3.5 mmol) in dichloromethane (8 mL) was added thionyl chloride (0.38 mL) at 0° C. The solution was stirred at ambient temperature for 2 hours and the mixture was concentrated in vacuo to provide 3-(chloromethyl-d₂)-1-methyl-1H-pyrazole as a liquid (0.4 g, crude): ¹H NMR (400 MHz, CDCl₃) δ 7.59 (s, 1H), 6.58 (s, 1H), 4.19 (s, 3H).

Scheme 5 Preparation of (chloromethyl-d₂)benzene

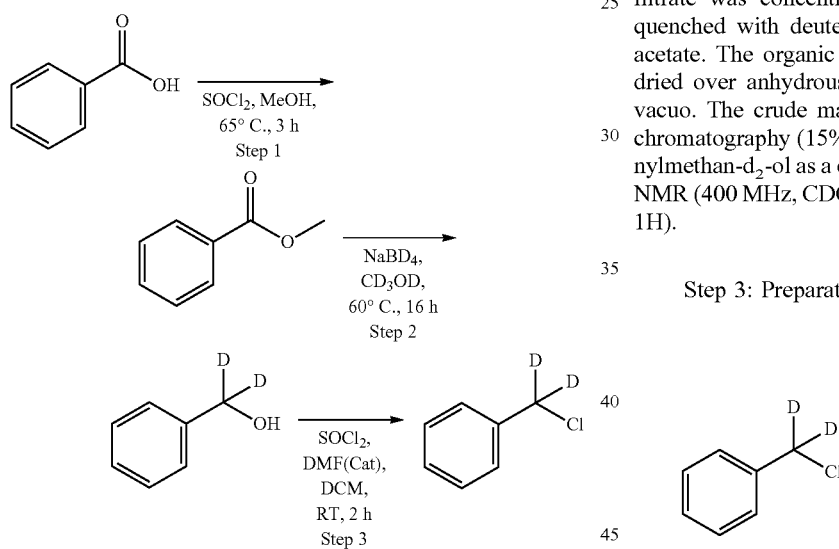

Step 1: Preparation of Methyl Benzoate

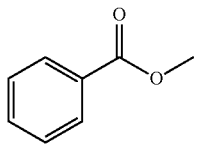

To a stirred solution of benzoic acid (2 g, 16.3 mmol) in methanol (20 mL) was added thionyl chloride (2 mL) at 0° C. and the solution was heated to 60° C. for 3 hours. The reaction mixture was cooled to ambient temperature, concentrated in vacuo to remove volatiles and the residue was quenched with saturated sodium carbonate solution and extracted with ethyl acetate. The organic layer was washed with water, brine, dried over anhydrous sodium sulfate and concentrated in vacuo to provide methyl benzoate as a colorless liquid (1.7 g, 75% yield): ¹H NMR (400 MHz, CDCl₃) δ 8.44 (d, J=7.6 Hz, 2H), 7.54-7.64 (m, 1H), 7.42-7.45 (m, 2H), 3.92 (s, 3H).

Step 2: Preparation of phenylmethan-d₂-ol

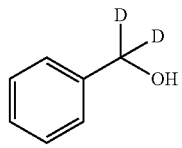

To a solution of methyl benzoate (0.5 g, 3.67 mmol) in methan-d₃-ol-d (4 mL) and was added sodium borodeuteride (0.46 g, 11.02 mmol, 99% D) at ambient temperature. The resulting mixture was heated to 60° C. for 16 hours. The reaction mixture was cooled to ambient temperature and diluted with ethyl acetate and filtered through celite. The filtrate was concentrated in vacuo and the residue was quenched with deuterium oxide and extracted with ethyl acetate. The organic layer was washed with water, brine, dried over anhydrous sodium sulfate and concentrated in vacuo. The crude material obtained was purified by flash chromatography (15% ethyl acetate/hexane) to provide phenylmethan-d₂-ol as a colorless liquid (0.15 g, 37% yield): ¹H NMR (400 MHz, CDCl₃) δ 7.36-7.37 (m, 4H), 7.30-7.32 (m, 1H).

Step 3: Preparation of (chloromethyl-d₂)benzene

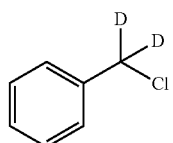

To a solution of phenylmethan-d₂-ol (0.15 g, 1.36 mmol) in dichloromethane (4 mL) was added thionyl chloride (0.2 mL) and N,N-dimethylformamide (catalytic) at 0° C. The resulting solution was stirred at ambient temperature for 2 hours. The reaction mixture was diluted with diethyl ether and washed with water, brine, dried over sodium sulfate, filtered and concentrated in vacuo (<30° C.) to provide (chloromethyl-d₂)benzene as a liquid (0.1 g, crude).

Scheme 6 Preparation of 1-(chloromethyl-d₂)-3-(trifluoromethyl)benzene

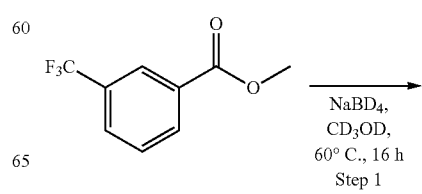

-continued

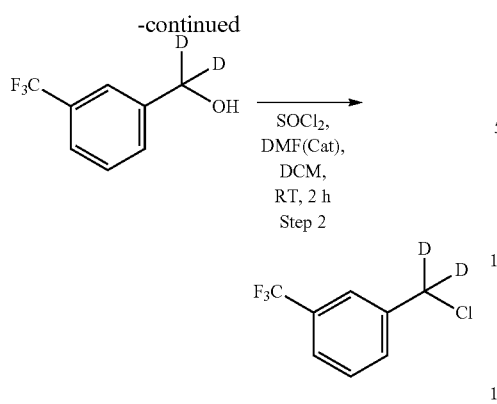

Step 1: Preparation of (3-(trifluoromethyl)phenyl)methan-d₂-ol

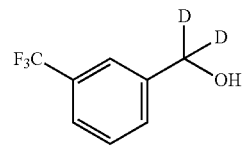 [SMILES: [2H]C([2H])(O)c1cccc(C(F)(F)F)c1]

To a solution of methyl 3-(trifluoromethyl)benzoate (0.25 g, 1.22 mmol) in methan-d₃-ol-d (4 mL) was added sodium borodeuteride (0.15 g, 3.67 mmol, 99% D) at ambient temperature and the solution was heated to 60° C. for 16 hours. The reaction mixture was cooled to ambient temperature, concentrated in vacuo and the residue was quenched with water and extracted with ethyl acetate. The organic layer was washed with water, brine, dried over anhydrous sodium sulfate and concentrated in vacuo. The crude material was purified by flash chromatography (15% ethyl acetate/hexane) to provide (3-(trifluoromethyl) phenyl)methan-d₂-ol as a colorless liquid (0.2 g, crude): $^1$H NMR (400 MHz, CDCl₃) δ 7.64 (s, 1H), 7.55 (d, J=7.6 Hz, 2H), 7.46-7.50 (m, 1H).

Step 2: Preparation of 1-(chloromethyl-d₂)-3-(trifluoromethyl)benzene

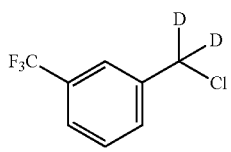

To a solution of (3-(trifluoromethyl)phenyl)methan-d₂-ol (0.2 g, 1.11 mmol) in dichloromethane (2 mL) was added thionyl chloride (0.25 mL) and N,N-dimethylformamide (cat.) at 0° C. The resulting solution was stirred at ambient temperature for 2 hours. The reaction mixture was diluted with diethyl ether and washed with water, brine, dried over sodium sulfate, filtered and concentrated in vacuo (<30° C.) to provide 1-(chloromethyl-d₂)-3-(trifluoromethyl)benzene as a liquid (0.2 g, crude): $^1$H NMR (400 MHz, CDCl₃) δ 7.65 (s, 1H), 7.58 (d, J=8 Hz, 2H), 7.47-7.51 (m, 1H).

Scheme 7 Preparation of 1-(chloromethyl-d₂)-3-methoxybenzene

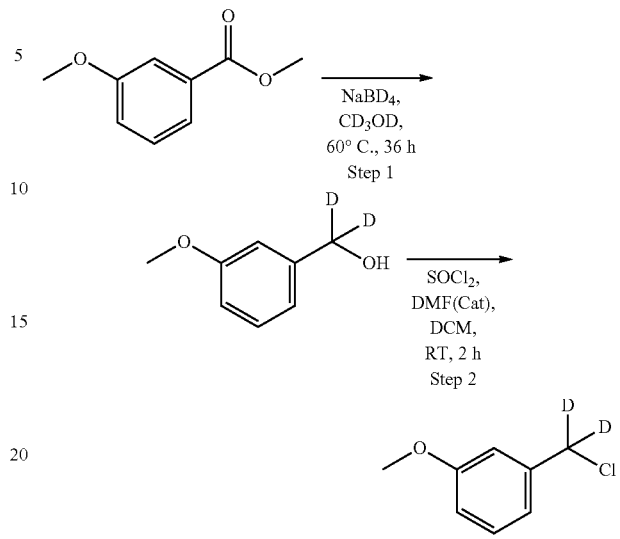

Step 1: Preparation of (3-methoxyphenyl)methan-d₂-ol

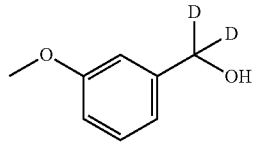

To a solution of methyl 3-methoxybenzoate (0.4 g, 2.4 mmol) in methan-d₃-ol-d (4 mL) was added sodium borodeuteride (0.5 g, 12 mmol, 99% D) at ambient temperature and the solution was heated to 60° C. for 36 hours. The reaction mixture was cooled to ambient temperature and concentrated in vacuo to give a crude residue. The crude residue was quenched with water and extracted with ethyl acetate. The organic layer was washed with water, brine, dried over anhydrous sodium sulfate and concentrated in vacuo. The crude material was purified by flash chromatography (15% ethyl acetate/hexane) to provide (3-methoxyphenyl)methan-d₂-ol as a colorless liquid (0.15 g, 45% yield): $^1$H NMR (400 MHz, CDCl₃) δ 7.29 (s, 1H), 6.44 (d, J=6.4 Hz, 2H), 6.83-6.85 (m, 1H).

Step 2: Preparation of 1-(chloromethyl-d₂)-3-methoxybenzene

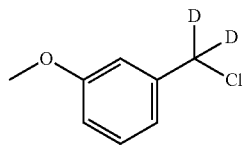

To a solution of (3-methoxyphenyl)methan-d₂-ol (0.23 g, 1.64 mmol) in dichloromethane (4 mL) was added thionyl chloride (0.4 mL) and N,N-dimethyl formamide (cat.) at 0°

C. and the solution was stirred at ambient temperature for 2 hours. The reaction mixture was diluted with diethyl ether and washed with water, brine, dried over sodium sulfate, filtered and concentrated in vacuo (<30° C.) to provide 1-(chloromethyl-d$_2$)-3-methoxybenzene as a liquid (0.25 g, crude): $^1$H NMR (400 MHz, CDCl$_3$) δ 7.29 (s, 1H), 6.93-6.97 (m, 2H), 6.85-6.87 (m, 1H).

Scheme 8 Preparation of 1-(chloromethyl-d$_2$)-2,4-difluorobenzene

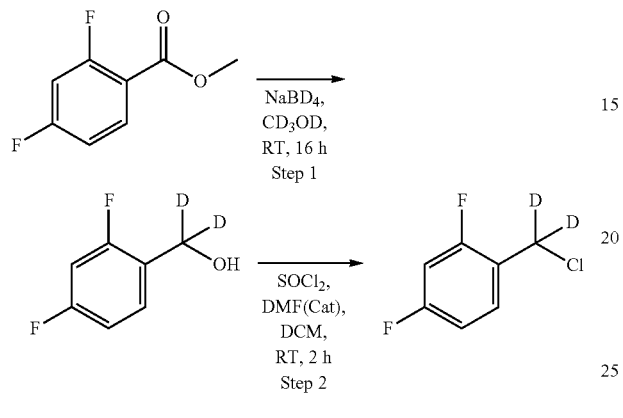

Step 1: Preparation of (2,4-difluorophenyl)methan-d$_2$-ol

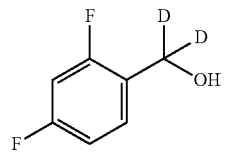

To a solution of methyl 2,4-difluorobenzoate (0.25 g, 1.45 mmol) in methan-d$_3$-ol-d (4 mL) was added sodium borodeuteride (0.12 g, 2.9 mmol, 99% D) at 0° C. and the solution was stirred at room temperature for 16 hours. The reaction mixture was concentrated in vacuo and the residue was quenched with water and extracted with ethyl acetate. The organic layer was washed with water, brine, dried over anhydrous sodium sulfate and concentrated in vacuo. The crude material was purified by flash chromatography (15% ethyl acetate/hexane) to provide (2,4-difluorophenyl)methan-d$_2$-ol as a colorless liquid (0.2 g, crude): $^1$H NMR (400 MHz, CDCl$_3$) δ 7.36-7.42 (m, 1H), 6.79-6.9 (m, 2H), 4.65 (br s, 0.09H).

Step 2: Preparation of 1-(chloromethyl-d$_2$)-2,4-difluorobenzene

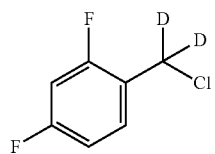

To a solution of (2,4-difluorophenyl)methan-d$_2$-ol(0.2 g, 1.36 mmol) in dichloromethane (2 mL), was added thionyl chloride (0.2 mL) and N,N-dimethylformamide (cat.) at 0° C. and the solution was stirred at ambient temperature for 2 hours. The reaction solvent was evaporated in vacuo to provide 1-(chloromethyl-d$_2$)-2,4-difluorobenzene as a liquid (0.1 g, crude): $^1$H NMR (400 MHz, CDCl$_3$) δ 8.03 (s, 1H), 7.38-7.40 (m, 1H), 6.84-6.88 (m, 1H).

Examples 1 and 2: Preparation of atropisomers of 3-chloro-4-((3,5-difluoropyridin-2-yl)methoxy-d$_2$)-2'-(2-(2-hydroxypropan-2-yl)pyrimidin-4-yl)-5',6-dimethyl-2H-[1,4'-bipyridin]-2-one

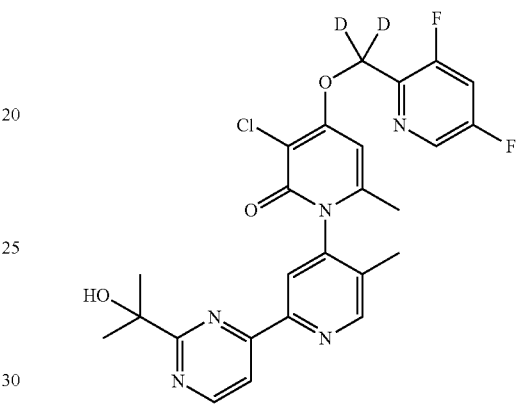

Scheme 9: Preparation of atropisomers of 3-chloro-4-((3,5-difluoropyridin-2-yl)methoxy-d$_2$)-2'-(2-(2-hydroxypropan-2-yl)pyrimidin-4-yl)-5',6-dimethyl-2H-[1,4'-bypyridin]-2-one

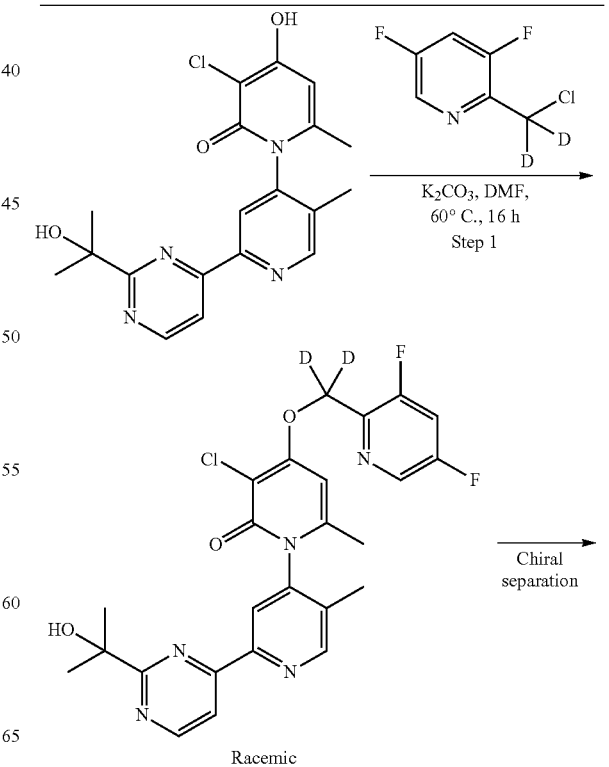

-continued

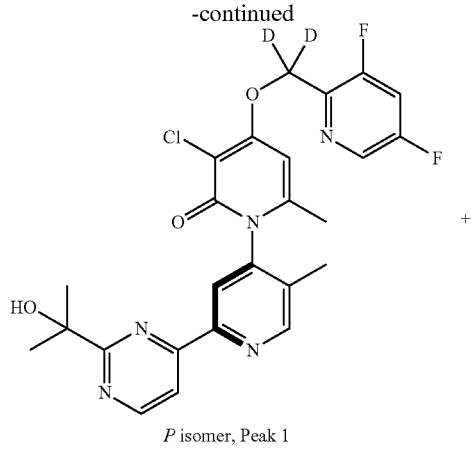

P isomer, Peak 1

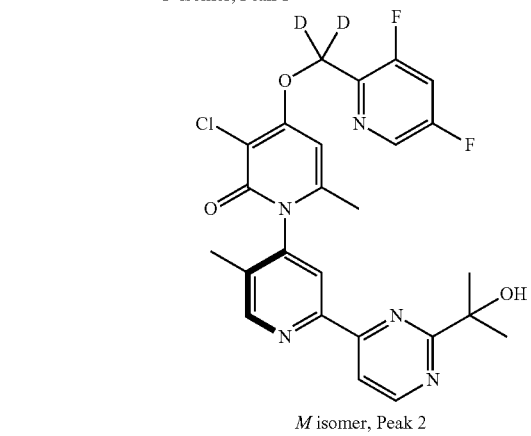

M isomer, Peak 2

Step 1: Preparation of 3-chloro-4-((3,5-difluoropyridin-2-yl)methoxy-d₂)-2'-(2-(2-hydroxypropan-2-yl)pyrimidin-4-yl)-5',6-dimethyl-2H-[1,4'-bipyridin]-2-one

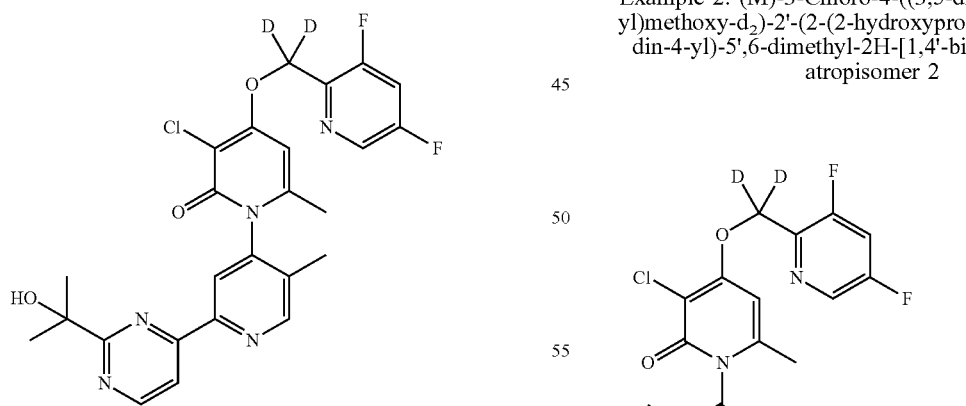

To a suspension of 3-chloro-4-hydroxy-2'-(2-(2-hydroxypropan-2-yl)pyrimidin-4-yl)-5',6-dimethyl-2H-[1,4'-bipyridin]-2-one (0.4 g, 1.03 mmol) and potassium carbonate (0.42 g, 3.1 mmol) in N,N-dimethylformamide (5 mL) was added 2-(chloromethyl-d₂)-3,5-difluoropyridine (0.2 g, 1.24 mmol) at ambient temperature. The mixture was heated to 60° C. for 16 hours. The reaction was cooled to ambient temperature, diluted with ethyl acetate and washed with cold water. The organic layer was washed with brine, dried over anhydrous sodium sulfate, filtered and concentrated in vacuo. The crude material was purified by flash chromatography (4.5% methanol/dichloromethane) to provide 3-chloro-4-((3,5-difluoropyridin-2-yl)methoxy-d₂)-2'-(2-(2-hydroxypropan-2-yl)pyrimidin-4-yl)-5',6-dimethyl-2H-[1,4'-bipyridin]-2-one as an off-white solid (0.34 g, 64% yield). The atropisomers were separated by following chiral prep HPLC method.

Analytical Conditions:
  Column: CHIRALPAK IC (100 mm×4.6 mm×3mic)
  Mobile phase: Ethanol with 0.1% DEA
  Flow rate: 1 mL/min Example 1: (P)-3-Chloro-4-((3,5-difluoropyridin-2-yl)methoxy-d₂)-2'-(2-(2-hydroxypropan-2-yl)pyrimidin-4-yl)-5',6-dimethyl-2H-[1,4'-bipyridin]-2-one, atropisomer 1

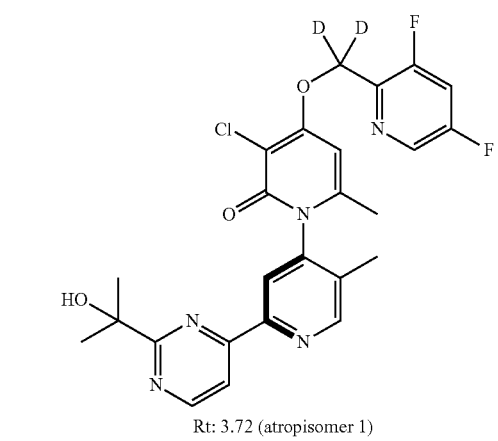

Rt: 3.72 (atropisomer 1)

Off-white solid (0.14 g, 19% yield): ¹H NMR (400 MHz, DMSO-d₆) δ 8.94 (d, J=4.8 Hz, 1H), 8.83 (s, 1H), 8.67 (s, 1H), 8.59 (s, 1H), 8.21 (d, J=5.2 Hz, 1H), 8.06-8.1 (m, 1H), 6.82 (s, 1H), 5.24 (s, 1H), 2.08 (s, 3H), 1.95 (s, 3H), 1.51 (d, J=4 Hz, 6H); MS (ES) m/z 516.2 (M+H). 94.4% d₂, 5.4% d₁.

Example 2: (M)-3-Chloro-4-((3,5-difluoropyridin-2-yl)methoxy-d₂)-2'-(2-(2-hydroxypropan-2-yl)pyrimidin-4-yl)-5',6-dimethyl-2H-[1,4'-bipyridin]-2-one, atropisomer 2

Rt: 10.14 (atropisomer 2)

Off-white solid (0.12 g, 16% yield): ¹H NMR (400 MHz, DMSO-d₆) δ 8.95 (d, J=5.2 Hz, 1H), 8.83 (s, 1H), 8.67 (s, 1H), 8.59 (s, 1H), 8.21 (d, J=4.8 Hz, 1H), 8.06-8.1 (in, 1H), 6.82 (s, 1H), 5.24 (s, 1H), 2.08 (s, 3H), 1.95 (s, 3H), 1.51 (d, J=4 Hz, 6H); MS (ES) m/z 516.2 (M+H).

The examples in Table 2 were prepared by the general methods described above.

TABLE 2

Examples 3-12

| Example Number | Structure | Compound Name | Spectroscopic Data |
|---|---|---|---|
| Example 3 | 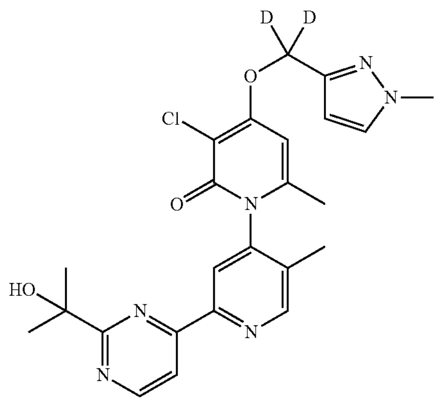 [SMILES: [2H]C([2H])(Oc1cc(C)n(-c2cc(-c3ccnc(C(C)(C)O)n3)ncc2C)c(=O)c1Cl)c1ccn(C)n1] | 3-Chloro-2'-(2-(2-hydroxypropan-2-yl)pyrimidin-4-yl)-5',6-dimethyl-4-((1-methyl-1H-pyrazol-3-yl)methoxy-d$_2$)-2H-[1,4'-bipyridin]-2-one (atropisomer 1) | (0.15 g, 34% yield, off-white solid): $^1$H NMR (400 MHz, DMSO-d$_6$) δ 8.95 (d, J = 5.2 Hz, 1H), 8.84 (s, 1H), 8.66 (s, 1H), 8.22 (d, J = 4.8 Hz, 1H), 7.71 (s, 1H), 6.83 (s, 1H), 6.39 (s, 1H), 5.24 (s, 1H), 3.85 (s, 3H), 2.08 (s, 3H), 1.96 (s, 3H), 1.51 (d, J = 4 Hz, 6H); MS (ES) m/z 483.3 (M + H). HPLC purity @ 254 nM is 99.61%. 92.3% d$_2$, 7.7% d$_1$ |
| Example 4 | 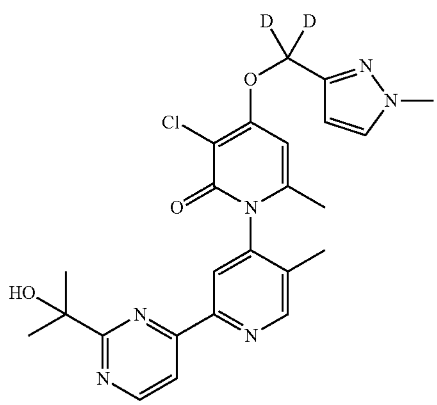 [SMILES: [2H]C([2H])(Oc1cc(C)n(-c2cc(-c3ccnc(C(C)(C)O)n3)ncc2C)c(=O)c1Cl)c1ccn(C)n1] | 3-Chloro-2'-(2-(2-hydroxypropan-2-yl)pyrimidin-4-yl)-5',6-dimethyl-4-((1-methyl-1H-pyrazol-3-yl)methoxy-d$_2$)-2H-[1,4'-bipyridin]-2-one (atropisomer 2) | (0.12 g, 27% yield, off-white solid): $^1$H NMR (400 MHz, DMSO-d$_6$) δ 8.95 d, J = 5.2 Hz, 1H), 8.84 (s, 1H), 8.67 (s, 1H), 8.22 (d, J = 4.8 Hz, 1H), 7.71 (s, 1H), 6.83 (s, 1H), 6.39 (s, 1H), 5.24 (s, 1H), 3.85 (s, 3H), 2.08 (s, 3H), 1.96 (s, 3H), 1.51 (d, J = 4 Hz, 6H); MS (ES) m/z 483.3 (M + H). HPLC purity @ 254 nM is 100%. |
| Example 5 | 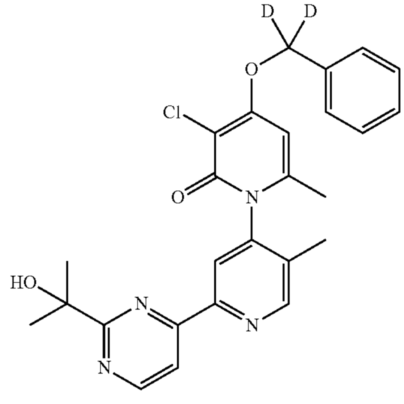 [SMILES: [2H]C([2H])(Oc1cc(C)n(-c2cc(-c3ccnc(C(C)(C)O)n3)ncc2C)c(=O)c1Cl)c1ccccc1] | 3-Chloro-2'-(2-(2-hydroxypropan-2-yl)pyrimidin-4-yl)-5',6-dimethyl-4-(phenylmethoxy-d$_2$)-2H-[1,4'-bipyridin]-2-one (atropisomer 1) | (0.04 g, 7% yield, off-white solid): $^1$H NMR (400 MHz, DMSO-d$_6$) δ 8.95 (d, J = 5.6 Hz, 1H), 8.83 (s, 1H), 8.65 (s, 1H), 8.21 (d, J = 4.8 Hz, 1H), 7.36-7.50 (m, 5H), 6.77 (s, 1H), 5.21 (s, 1H), 2.08 (s, 3H), 1.96 (s, 3H), 1.50 (d, J = 4.8 Hz, 6H); MS (ES) m/z 479.1 (M + H). HPLC purity @ 254 nM is 99.70%. 96.3% d$_2$, 3.3% d$_1$. |

TABLE 2-continued

Examples 3-12

| Example Number | Structure | Compound Name | Spectroscopic Data |
|---|---|---|---|
| Example 6 | 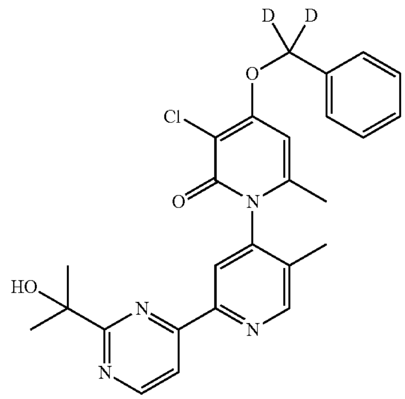 [SMILES: [2H]C([2H])(Oc1cc(C)n(-c2cc(-c3ccnc(C(C)(C)O)n3)ncc2C)c(=O)c1Cl)c1ccccc1] | 3-Chloro-2'-(2-(2-hydroxypropan-2-yl)pyrimidin-4-yl)-5',6-dimethyl-4-(phenylmethoxy-d$_2$)-2H-[1,4'-bipyridin]-2-one (atropisomer 2) | (0.035 g, 6% yield, off-white solid): $^1$H NMR (400 MHz, DMSO-d$_6$) δ 8.94 (d, J = 5.2 Hz, 1H), 8.83 (s, 1H), 8.65 (s, 1H), 8.21 (d, J = 5.2 Hz, 1H), 7.36-7.50 (m, 5H), 6.77 (s, 1H), 5.21 (s, 1H), 2.08 (s, 3H), 1.96 (s, 3H), 1.50 (d, J = 3.6 Hz, 6H); MS (ES) m/z 479.1 (M + H). HPLC purity @ 254 nM is 99.84%. |
| Example 7 | 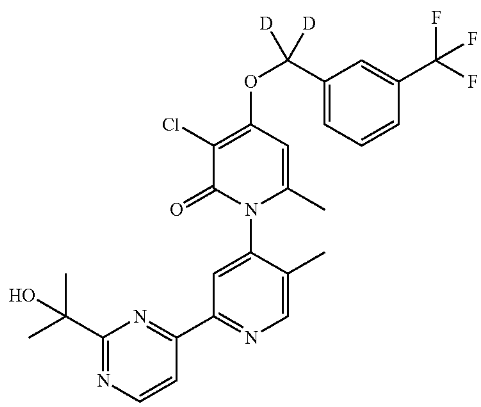 [SMILES: [2H]C([2H])(Oc1cc(C)n(-c2cc(-c3ccnc(C(C)(C)O)n3)ncc2C)c(=O)c1Cl)c1cccc(C(F)(F)F)c1] | 3-Chloro-2'-(2-(2-hydroxypropan-2-yl)pyrimidin-4-yl)-5',6-dimethyl-4-((3-(trifluoromethyl)phenyl)methoxy-d$_2$)-2H-[1,4'-bipyridin]-2-one (atropisomer 1) | (0.082 g, 20% yield, off-white solid): $^1$H NMR (400 MHz, DMSO-d$_6$) δ 8.95 (d, J = 4.8 Hz, 1H), 8.84 (s, 1H), 8.66 (s, 1H), 8.22 (d, J = 4.8 Hz, 1H), 7.87 (s, 1H), 7.60-7.81 (m, 3H), 6.77 (s, 1H), 5.22 (s, 1H), 2.08 (s, 3H), 1.96 (s, 3H), 1.50 (d, J = 4.4 Hz, 6H); MS (ES) m/z 547.2 (M + H). HPLC purity @ 254 nM is 99.80%. 97.2% d$_2$, 2.8% d$_1$. |
| Example 8 | 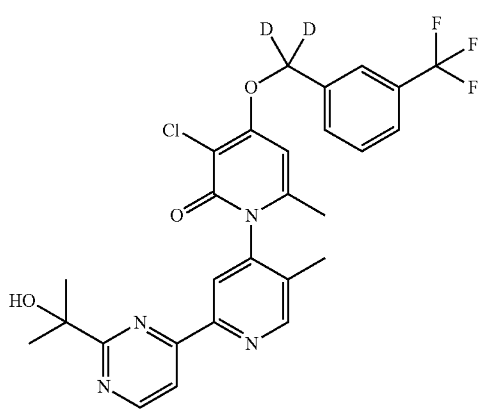 [SMILES: [2H]C([2H])(Oc1cc(C)n(-c2cc(-c3ccnc(C(C)(C)O)n3)ncc2C)c(=O)c1Cl)c1cccc(C(F)(F)F)c1] | 3-Chloro-2'(2-(2-hydroxypropan-2-yl)pyrimidin-4-yl)-5',6-dimethyl-4-((3-(trifluoromethyl)phenyl)methoxy-d$_2$)-2H-[1,4'-bipyridin]-2-one (atropisomer 2) | (0.07 g, 17% yield, off-white solid): $^1$H NMR (400 MHz, DMSO-d$_6$) δ 8.95 (d, J = 5.2 Hz, 1H), 8.84 (s, 1H), 8.66 (s, 1H), 8.22 (d, J = 5.2 Hz, 1H), 7.87 (s, 1H), 7.68-7.81 (m, 3H), 6.77 (s, 1H), 5.22 (s, 1H), 2.08 (s, 3H), 1.96 (s, 3H), 1.50 (d, J = 4.4 Hz, 6H); MS (ES) m/z 547.2 (M + H). HPLC purity @ 254 nM is 99.78%. |

TABLE 2-continued

Examples 3-12

| Example Number | Structure | Compound Name | Spectroscopic Data |
|---|---|---|---|
| Example 9 | 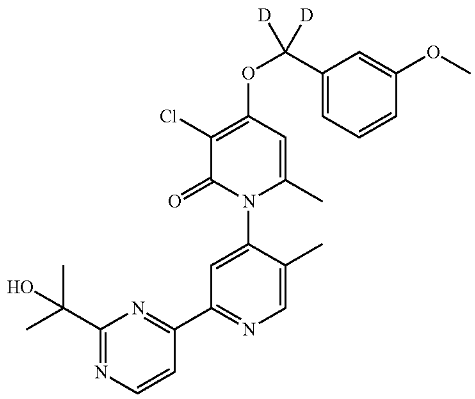 [SMILES: [2H]C([2H])(Oc1cc(C)n(-c2cc(-c3ccnc(C(C)(C)O)n3)ncc2C)c(=O)c1Cl)c1cccc(OC)c1] | 3-Chloro-2'-(2-(2-hydroxypropan-2-yl)pyrimidin-4-yl)-4-((3-methoxyphenyl)methoxy-d$_2$)-5',6-dimethyl-2H-[1,4'-bipyridin]-2-one (atropisomer 1) | (0.11 g, 17% yield, off-white solid): $^1$H NMR (400 MHz, DMSO-d$_6$) δ 8.94 (d, J = 4.8 Hz, 1H), 8.83 (s, 1H), 8.66 (s, 1H), 8.21 (d, J = 4.8 Hz, 1H), 7.33-7.37 (m, 1H), 7.04 (m, 2H), 6.94 (d, J = 8 Hz, 1H), 6.76 (s, 1H), 5.23 (s, 1H), 3.77 (s, 3H), 2.08 (s, 3H), 1.95 (s, 3H), 1.50 (d, J = 4 Hz, 6H); MS (ES) m/z 509.1 (M + H). HPLC purity @ 254 nM is 99.40%. 96.9% d$_2$, 3.1% d$_1$. |
| Example 10 | 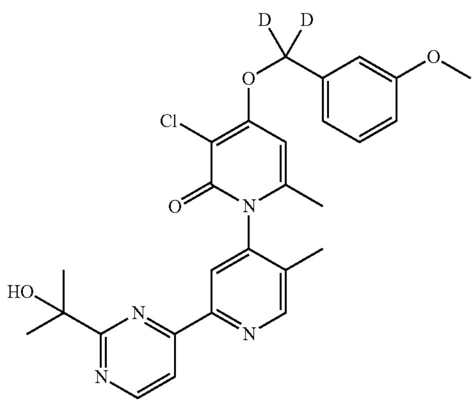 [SMILES: [2H]C([2H])(Oc1cc(C)n(-c2cc(-c3ccnc(C(C)(C)O)n3)ncc2C)c(=O)c1Cl)c1cccc(OC)c1] | 3-Chloro-2'-(2-(2-hydroxypropan-2-yl)pyrimidin-4-yl)-4-((3-methoxyphenyl) methoxy-d$_2$)-5',6-dimethyl-2H-[1,4'-bipyridin]-2-one (atropisomer 2) | (0.1 g, 16% yield, off white solid): $^1$H NMR (400 MHz, DMSO-d$_6$) δ 8.95 (d, J = 5.6 Hz, 1H), 8.83 (s, 1H), 8.66 (s, 1H), 8.21 (d, J = 4.8 Hz, 1H), 7.33-7.37 (m, 1H), 7.06 (m, 2H), 6.94 (d, J = 8 Hz, 1H), 6.76 (s, 1H), 5.23 (s, 1H), 3.77 (s, 3H), 2.08 (s, 3H), 1.95 (s, 3H), 1.50 (d, J = 3.6 Hz, 6H); MS (ES) m/z 509.2 (M + H). HPLC purity @ 254 nM is 99.89%. |
| Example 11 | 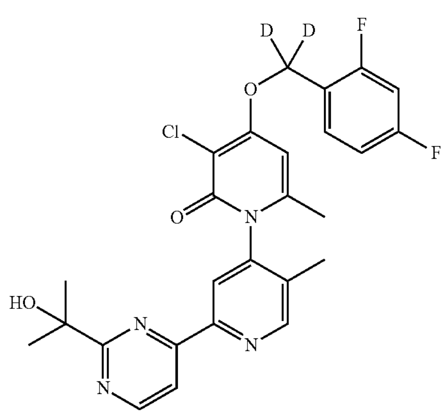 | 3-Chloro-4-((2,4-difluorophenyl)methoxy-d$_2$)-2'-(2-(2-hydroxypropan-2-yl)pyrimidin-4-yl)-5',6-dimethyl-2H-[1,4'-bipyridin]-2-one (atropisomer 1) | (0.021 g, 5% yield, off-white solid): $^1$H NMR (400 MHz, DMSO-d$_6$) δ 8.95 (d, J = 4.8 Hz, 1H), 8.84 (s, 1H), 8.66 (s, 1H), 8.22 (d, J = 4.8 Hz, 1H), 7.66-7.72 (m, 1H), 7.34-7.38 (m, 1H), 7.17-7.21 (m, 1H), 6.84 (s, 1H), 5.23 (s, 1H), 2.09 (s, 3H), 1.98 (s, 3H), 1.51 (d, J = 4 Hz, 6H); MS (ES) m/z 515.3 (M + H). HPLC purity @ 254 nM is 98.59%. 96.8% d$_2$, 3.1% d$_1$. |

TABLE 2-continued

Examples 3-12

| Example Number | Structure | Compound Name | Spectroscopic Data |
|---|---|---|---|
| Example 12 | 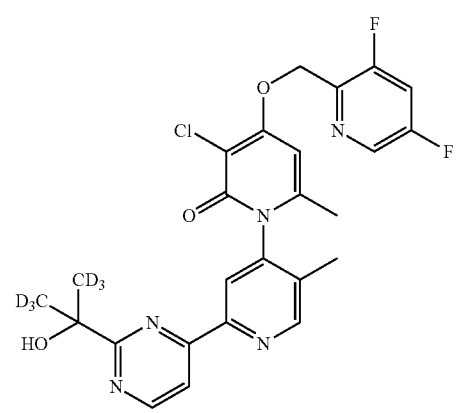 | 3-Chloro-4-((2,4-difluorophenyl)methoxy-$d_2$)-2'-(2-(2-hydroxypropan-2-yl)pyrimidin-4-yl)-5',6-dimethyl-2H-[1,4'-bipyridin]-2-one (atropisomer 2) | (0.028 g, 7% yield, off-white solid): $^1$H NMR (400 MHz, DMSO-$d_6$) δ 8.95 (d, J = 5.2 Hz, 1H), 8.84 (s, 1H), 8.66 (s, 1H), 8.22 (d, J = 5.2 Hz, 1H), 7.66-7.72 (m, 1H), 7.33-7.39 (m, 1H), 7.17-7.22 (m, 1H), 6.84 (s, 1H), 5.22 (s, 1H), 2.09 (s, 3H), 1.97 (s, 3H), 1.51 (d, J = 5.2 Hz, 6H); MS (ES) m/z 515.3 (M + H). HPLC purity @ 254 nM is 99.68%. |

Examples 13 and 14: Preparation of atropisomers of 3-chloro-4-((3,5-difluoropyridin-2-yl)methoxy)-2'-(2-(2-hydroxypropan-2-yl-1,1,1,3,3,3-$d_6$)pyrimidin-4-yl)-5',6-dimethyl-2H-[1,4'-bipyridin]-2-one Scheme 10 Preparation of 2-hydroxy-2-(methyl-$d_3$)propanimidamide-3,3,3-$d_3$

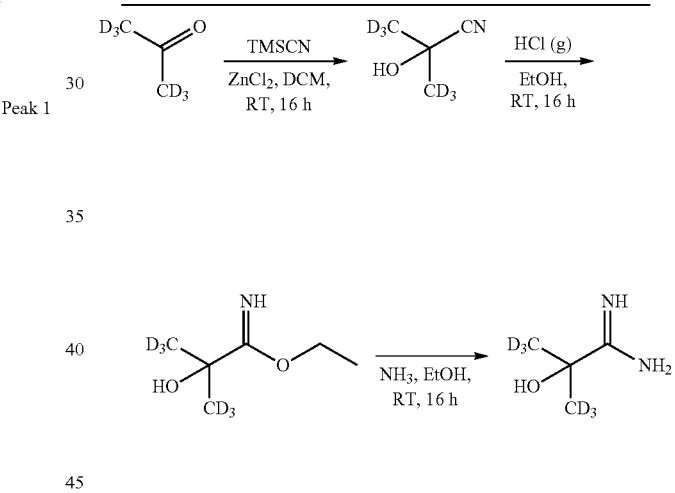

Peak 1

Step 1: Preparation of 2-hydroxy-2-(methyl-$d_3$)propanenitrile-3,3,3-$d_3$

Peak 2

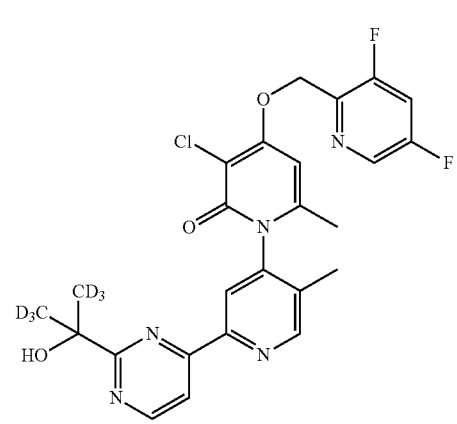

To a solution of propan-2-one-$d_6$ (99% atom D) (1 g, 15.6 mmol) in dichloromethane (10 mL) was added zinc chloride (0.21 g, 1.5 mmol) and trimethylsilanecarbonitrile (1.85 g, 18 mmol) at 0° C. and the solution was warmed to room temperature and stirred for 16 hours. The reaction mixture was quenched with water and extracted with ethyl acetate. The organic layer was washed with water, brine, dried over anhydrous sodium sulfate and concentrated in vacuo to provide 2-hydroxy-2-(methyl-$d_3$)propanenitrile-3,3,3-$d_3$ as a colorless liquid (0.9 g, crude): $^1$H NMR (400 MHz, DMSO-$d_6$) δ 6.35 (s, 1H).

Step 2: Preparation of ethyl 2-hydroxy-2-(methyl-d₃)propanimidate-3,3,3-d₃

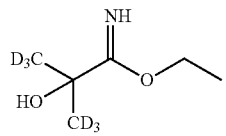

HCl gas was purged in to a solution of 2-hydroxy-2-(methyl-d₃)propanenitrile-3,3,3-d₃ (0.9 g, 9.8 mmol) in ethanol (15 mL) at 0° C. for 30 minutes and the solution was stirred at ambient temperature for 16 hours. The reaction mixture was concentrated in vacuo to remove volatiles to provide ethyl 2-hydroxy-2-(methyl-d₃)propanimidate-3,3,3-d₃ as a viscous liquid (1 g, crude): MS (ES) m/z 138.2 (M+H).

Step 3. Preparation of 2-hydroxy-2-(methyl-d₃)propanimidamide-3,3,3-d₃

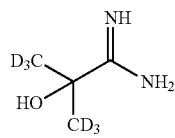

Ammonia gas was purged in to a solution of ethyl 2-hydroxy-2-(methyl-d₃)propanimidate-3,3,3-d₃ (1 g, 7.2 mmol) in ethanol (10 mL) at 0° C. for 30 minutes and stirred at ambient temperature for 16 hours. The reaction mixture was concentrated in vacuo to remove volatiles and the residue was triturated with diethyl ether to provide 2-hydroxy-2-(methyl-d₃)propanimidamide-3,3,3-d₃ as an off-white solid (0.8 g, crude): MS (ES) m/z 109.2 (M+H).

Scheme 11 Preparation of atropisomers of 3-chloro-4-((3,5-difluoropyridin-2-yl)methoxy)-2'-(2-(2-hydroxypropan-2-yl-1,1,1,3,3,3-d₆)pyrimidin-4-yl)-5',6-dimethyl-2H-[1,4'-bypyridin]-2-one

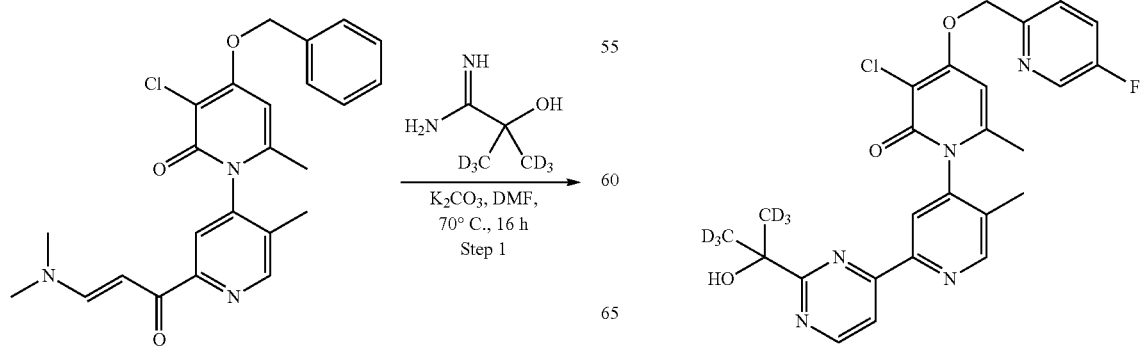

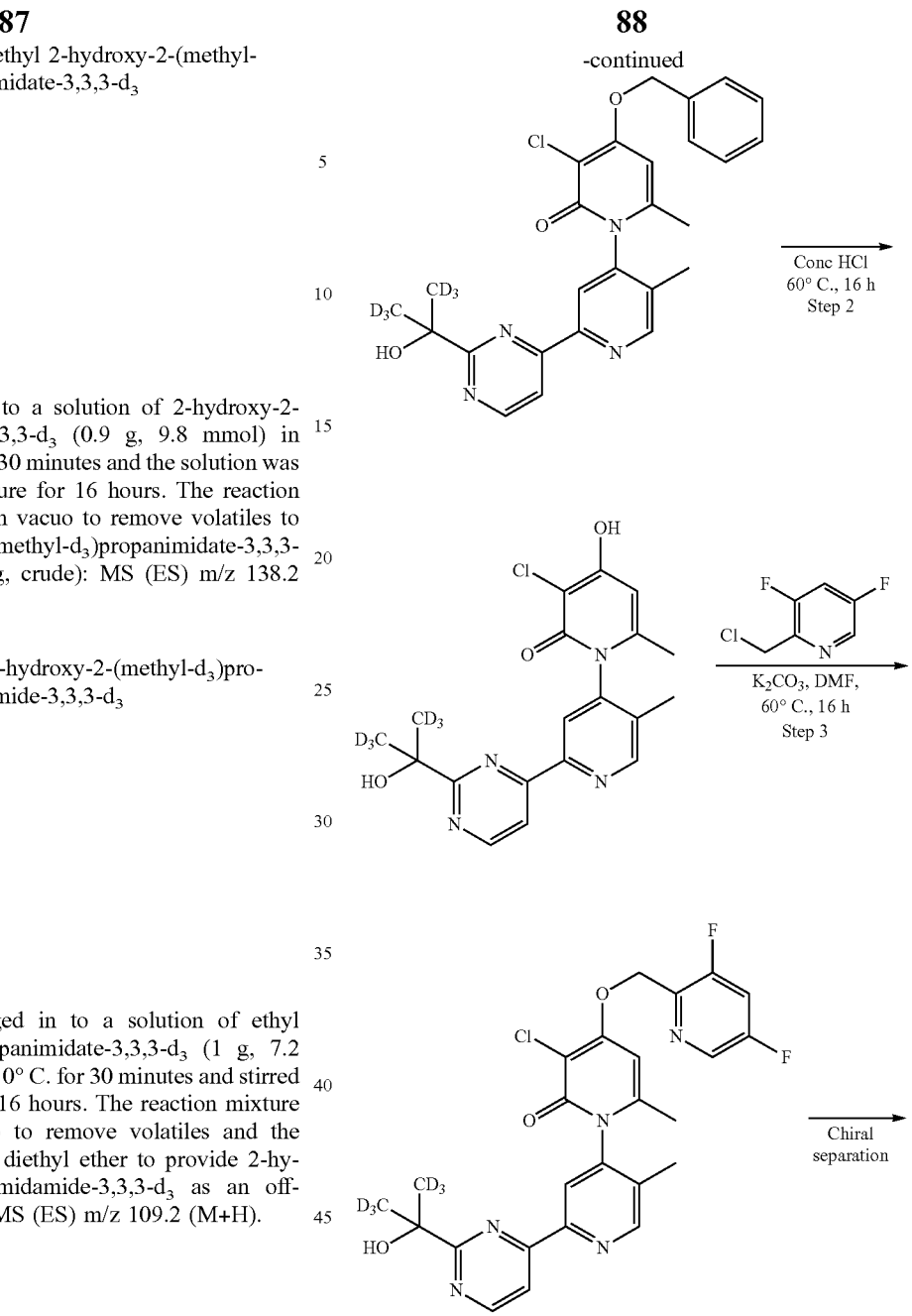

-continued

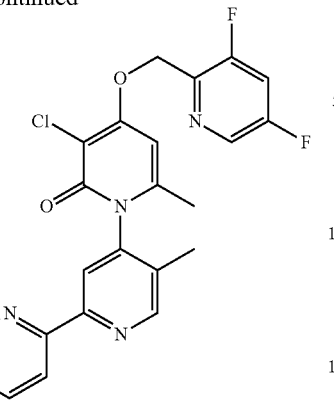

Step 1: Preparation of 4-(benzyloxy)-3-chloro-2'-(2-(2-hydroxypropan-2-yl-1,1,1,3,3,3-d₆)pyrimidin-4-yl)-5',6-dimethyl-2H-[1,4'-bipyridin]-2-one

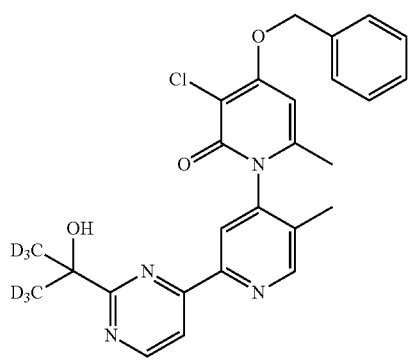 [SMILES: [2H]C([2H])([2H])C(O)(c1nccc(-c2cc(-n3c(C)cc(OCc4ccccc4)c(Cl)c3=O)c(C)cn2)n1)C([2H])([2H])[2H]]

A suspension of (E)-4-(benzyloxy)-3-chloro-2'-(3-(dimethylamino)acryloyl)-5',6-dimethyl-2H-[1,4'-bipyridin]-2-one (0.85 g, 1.94 mmol) and potassium carbonate (0.8 g, 5.8 mmol) in N,N-dimethylformamide (10 mL) was treated with 2-hydroxy-2-(methyl-d₃)propanimidamide-3,3,3-d₃ hydrochloride (0.7 g, 4.86 mmol) and the resulting mixture was heated at 75° C. for 16 hours. The reaction was cooled to ambient temperature, diluted with ethyl acetate and washed with cold water. The organic layer was washed with brine, dried over anhydrous sodium sulfate, filtered and concentrated in vacuo. The crude material was purified by flash chromatography (4.5% methanol/dichloromethane) to provide 4-(benzyloxy)-3-chloro-2'-(2-(2-hydroxypropan-2-yl-1,1,1,3,3,3-d₆)pyrimidin-4-yl)-5',6-dimethyl-2H-[1,4'-bipyridin]-2-one as an off-white solid (0.65 g, 65% yield): MS (ES) m/z 483.3 (M+H).

Step 2: Preparation of 3-chloro-4-hydroxy-2'-(2-(2-hydroxypropan-2-yl-1,1,1,3,3,3-d₆)pyrimidin-4-yl)-5',6-dimethyl-2H-[1,4'-bipyridin]-2-one

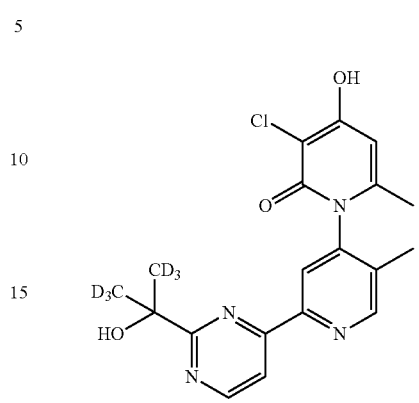

The solution of 4-(benzyloxy)-3-chloro-2'-(2-(2-hydroxypropan-2-yl-1,1,1,3,3,3-d₆)pyrimidin-4-yl)-5',6-dimethyl-2H-[1,4'-bipyridin]-2-one (0.3 g, 0.62 mmol) in conc. HCl (6 mL) was heated at 60° C. for 16 hours. The reaction was cooled to ambient temperature and concentrated in vacuo to give crude product. The crude residue was triturated with diethyl ether to provide 3-chloro-4-hydroxy-2'-(2-(2-hydroxypropan-2-yl-1,1,1,3,3,3-d₆)pyrimidin-4-yl)-5',6-dimethyl-2H-[1,4'-bipyridin]-2-one as yellow solid (0.25 g, crude): MS (ES) m/z 392.9 (M+H).

Step 3: Preparation of 3-chloro-4-((3,5-difluoropyridin-2-yl)methoxy)-2'-(2-(2-hydroxypropan-2-yl-1,1,1,3,3,3-d₆)pyrimidin-4-yl)-5',6-dimethyl-2H-[1,4'-bipyridin]-2-one

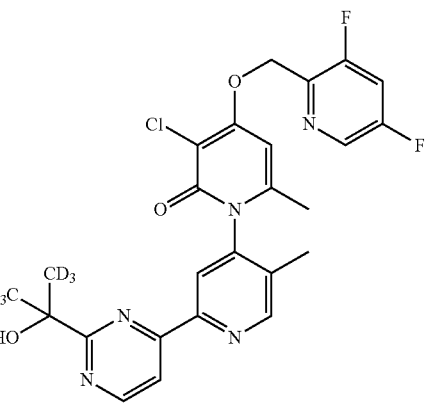

A suspension of 3-chloro-4-hydroxy-2'-(2-(2-hydroxypropan-2-yl-1,1,1,3,3,3-d₆)pyrimidin-4-yl)-5',6-dimethyl-2H-[1,4'-bipyridin]-2-one (0.25 g, 0.63 mmol) and potassium carbonate (0.26 g, 1.9 mmol) in N,N-dimethylformamide (4 mL) was treated with 2-(chloromethyl)-3,5-difluoropyridine (0.15 g, 0.95 mmol) and the resulting mixture was heated at 60° C. for 16 hours. The reaction was cooled to ambient temperature, diluted with ethyl acetate and washed with cold water. The organic layer was washed with brine, dried over anhydrous sodium sulfate, filtered and concentrated in vacuo. The crude material was purified by flash chromatography (3.8% methanol/ dichloromethane) to provide 3-chloro-4-((3,5-difluoropyridin-2-yl)methoxy)-2'-(2-(2-hydroxypropan-2-yl-1,1,1,3,3,3-d₆)pyrimidin-4-yl)-5',6-dimethyl-2H-[1,4'-bipyridin]-2-one as an off-white solid (0.25 g, 75% yield). The atropisomers were separated by following chiral prep HPLC method.

Analytical Conditions:
  Column: CHIRALPAK IC (100 mm×4.6 mm×3 mic)
  Mobile phase: Ethanol with 0.1% DEA
  Flow rate: 0.5 mL/min Example 13: 3-Chloro-4-((3,5-difluoropyridin-2-yl)methoxy)-2'-(2-(2-hydroxypropan-2-yl-1,1,1,3,3,3-d₆)pyrimidin-4-yl)-5',6-dimethyl-2H-[1,4'-bipyridin]-2-one, atropisomer 1

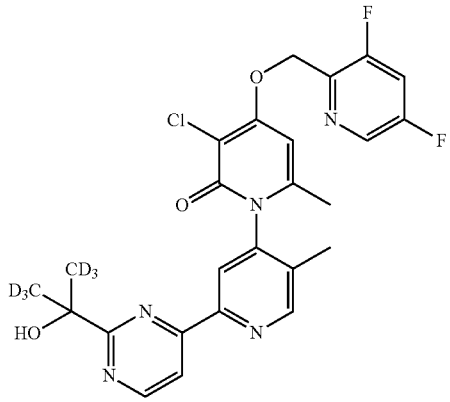

Rt: 2.63 (atropisomer 1)

Off-white solid (0.08 g, 24% yield): ¹H NMR (400 MHz, DMSO-d₆) δ 8.95 (d, J=4.4 Hz, 1H), 8.84 (s, 1H), 8.66 (s, 1H), 8.59 (s, 1H), 8.22 (d, J=5.2 Hz, 1H), 8.05-8.1 (m, 1H), 6.82 (s, 1H), 5.48 (s, 2H), 5.19 (s, 1H), 2.09 (s, 3H), 1.96 (s, 3H); MS (ES) m/z 520.1 (M+H). 93.44% d₆, 2.98% d₅, 3.05% d₄, 0.11% d₃, 0.23% d₂, 0.20% d₁, 0.40% d₀.

Example 14: 3-Chloro-4-((3,5-difluoropyridin-2-yl)methoxy)-2'-(2-(2-hydroxypropan-2-yl-1,1,1,3,3,3-d₆)pyrimidin-4-yl)-5',6-dimethyl-2H-[1,4'-bipyridin]-2-one, atropisomer 2

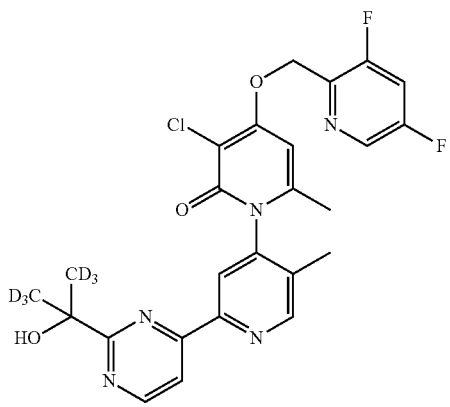 [SMILES: [2H]C([2H])([2H])C(O)(c1nccc(-c2cc(-n3c(C)cc(OCc4ncc(F)cc4F)c(Cl)c3=O)c(C)cn2)n1)C([2H])([2H])[2H]]

Rt: 7.21 (atropisomer 2)

Off-white solid (0.08 g, 23% yield): ¹H NMR (400 MHz, DMSO-d₆) δ 8.95 (d, J=4 Hz, 1H), 8.84 (s, 1H), 8.66 (s, 1H), 8.59 (s, 1H), 8.21 (d, J=4 Hz, 1H), 8.05-8.10 (m, 1H), 6.82 (s, 1H), 5.48 (s, 2H), 5.19 (s, 1H), 2.09 (s, 3H), 1.96 (s, 3H); MS (ES) m/z 520.1 (M+H).

Examples 15 and 16: Preparation of atropisomers of 3-chloro-2'-(2-(2-hydroxypropan-2-yl-1,1,1,3,3,3-d₆)pyrimidin-4-yl)-5',6-dimethyl-4-((1-methyl-1H-pyrazol-3-yl)methoxy)-2H-[1,4'-bipyridin]-2-one

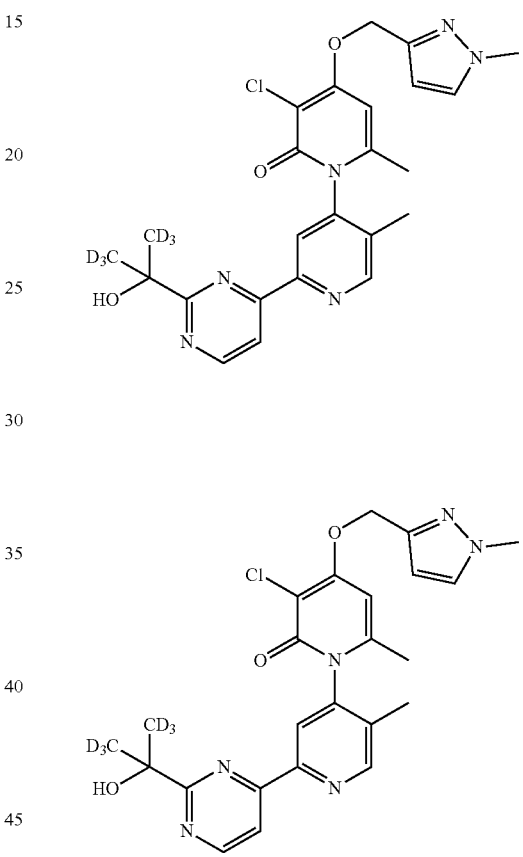

Scheme 12 Preparation of atropisomers of 3-chloro-2'-(2-(2-hydroxypropan-2-yl-1,1,1,3,3,3-d₆)pyrimidin-4-yl)-5',6-dimethyl-4-((1-methyl-1H-pyrazol-3-yl)methoxy)-2H-[1,4'-bypyridin]-2-one

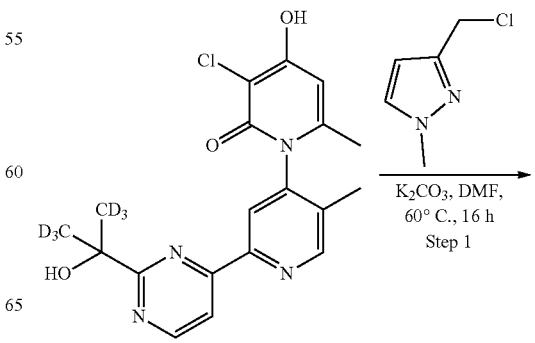

K₂CO₃, DMF, 60° C., 16 h
Step 1

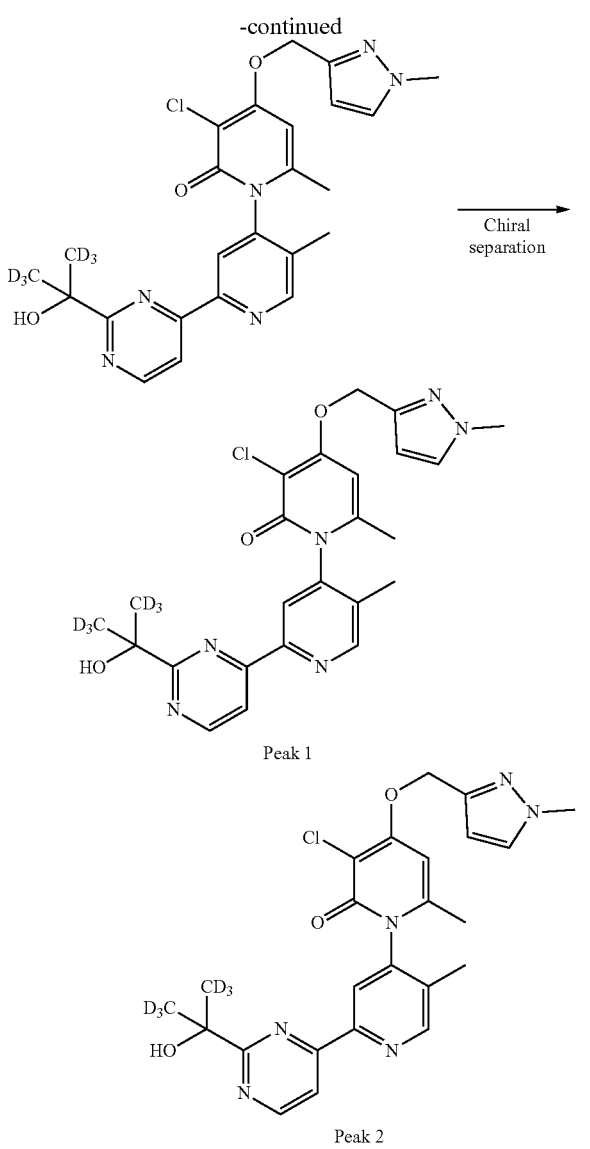

Peak 1

Peak 2

Step 1: Preparation of 3-chloro-2'-(2-(2-hydroxy-propan-2-yl-1,1,1,3,3,3-d₆)pyrimidin-4-yl)-5',6-dimethyl-4-((1-methyl-1H-pyrazol-3-yl)methoxy)-2H-[1,4'-bipyridin]-2-one

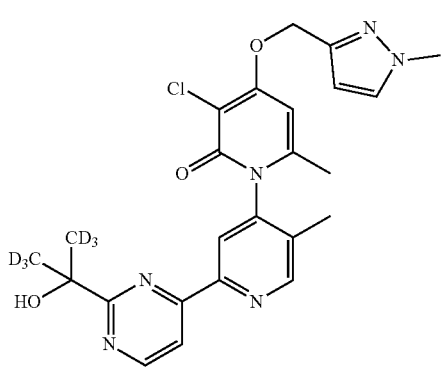 [SMILES: [2H]C([2H])([2H])C(O)(c1nccc(-c2cc(-n3c(C)cc(OCc4ccn(C)n4)c(Cl)c3=O)c(C)cn2)n1)C([2H])([2H])[2H]]

To a stirred solution of 3-chloro-4-hydroxy-2'-(2-(2-hydroxypropan-2-yl-1,1,1,3,3,3-d₆)pyrimidin-4-yl)-5',6-dimethyl-2H-[1,4'-bipyridin]-2-one (0.3 g, 0.76 mmol) and potassium carbonate (0.52 g, 3.82 mmol) in N,N-dimethylformamide (4 mL) was added 3-(chloromethyl)-1-methyl-1H-pyrazole (0.24 g, 1.91 mmol) and the mixture was heated to 60° C. for 16 hours. The reaction was cooled to ambient temperature, diluted with ethyl acetate and washed with cold water. The organic layer was washed with brine, dried over anhydrous sodium sulfate, filtered and concentrated in vacuo. The crude material was purified by flash chromatography (4% methanol/dichloromethane) to provide 3-chloro-2'-(2-(2-hydroxypropan-2-yl-1,1,1,3,3,3-d₆)pyrimidin-4-yl)-5',6-dimethyl-4-((1-methyl-1H-pyrazol-3-yl)methoxy)-2H-[1,4'-bipyridin]-2-one as an off-white solid (0.15 g, 40% yield). The atropisomers were separated by following chiral prep HPLC method.

Analytical Conditions:

Column: CHIRALPAK IC (100 mm×4.6 mm×3mic)

Mobile phase: 100% Ethanol in 0.1% DEA

Flow rate: 0.5 mL/min

Example 15: 3-Chloro-2'-(2-(2-hydroxypropan-2-yl-1,1,1,3,3,3-d₆)pyrimidin-4-yl)-5',6-dimethyl-4-((1-methyl-1H-pyrazol-3-yl)methoxy)-2H-[1,4'-bipyridin]-2-one, atropisomer 1

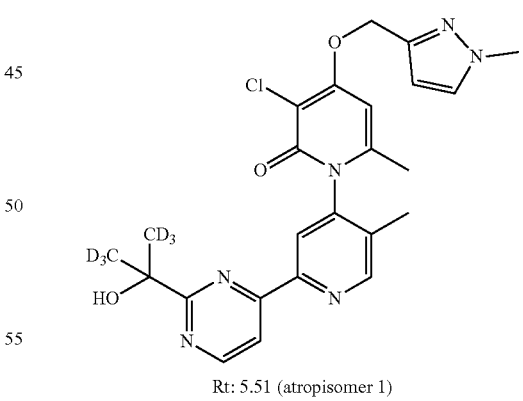

Rt: 5.51 (atropisomer 1)

Off-white solid (0.04 g, 12% yield): $^1$H NMR (400 MHz, DMSO-$d_6$) δ 8.94 (d, J=5.2 Hz, 1H), 8.83 (s, 1H), 8.64 (s, 1H), 8.21 (d, J=5.2 Hz, 1H), 7.70 (s, 1H), 6.82 (s, 1H), 6.39 (s, 1H), 5.25 (s, 2H), 5.18 (s, 1H), 3.85 (s, 3H), 2.08 (s, 3H), 1.96 (s, 3H); MS (ES) m/z 487.2 (M+H). 96.33% $d_6$, 2.92% $d_5$, 0.27% $d_4$, 0.13% $d_3$, 0.20% $d_2$, 0.15% $d_1$, 0.45% $d_0$ Example 16: 3-Chloro-2'-(2-(2-hydroxypropan-2-yl-1,1,1,3,3,3-d6)pyrimidin-4-yl)-5',6-dimethyl-4-((1-methyl-1H-pyrazol-3-yl)methoxy)-2H-[1,4'-bipyridin]-2-one, atropisomer 2

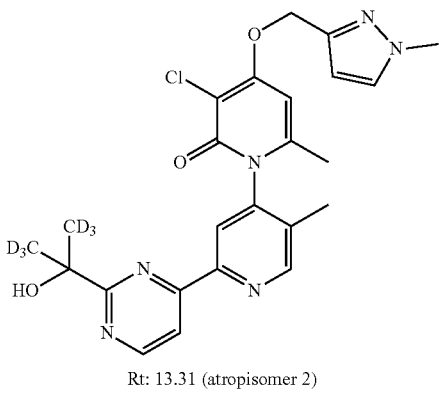 [SMILES: [2H]C([2H])([2H])C(O)(c1nccc(-c2cc(-n3c(C)cc(OCc4ccn(C)n4)c(Cl)c3=O)c(C)cn2)n1)C([2H])([2H])[2H]]

Rt: 13.31 (atropisomer 2)

Off-white solid (0.05 g, 12% yield): $^1$H NMR (400 MHz, DMSO-$d_6$) δ 8.94 (d, J=4.8 Hz, 1H), 8.83 (s, 1H), 8.64 (s, 1H), 8.21 (d, J=5.6 Hz, 1H), 7.70 (s, 1H), 6.82 (s, 1H), 6.39 (s, 1H), 5.25 (s, 2H), 5.18 (s, 1H), 3.84 (s, 3H), 2.08 (s, 3H), 1.96 (s, 3H); MS (ES) m/z 487.2 (M+H).

BIOLOGICAL ACTIVITY ASSAY

List of Biological Evaluation Abbreviations
  p38 Class of mitogen-activated protein kinases that are responsive to stress stimuli
  MAP Mitogen activated protein kinase
  MK2 Also known as MAPKAPK2. Refers to MAP kinase-activated protein kinase 2
  PRAK p38 regulated/activated kinase
  GST Glutathione S-transferase
  Hsp27 Heat-shock protein 27
  BSA Bovine serum albumin
  DTT Dithiothreitol
  ATP Adenosine triphosphate
  $IC_{50}$ Amount of a drug that's needed to inhibit a process by half
  $EC_{50}$ concentration of a drug which induces a response halfway between the baseline and maximum after a specified exposure time
  TNF Tumor necrosis factor
  IL Interleukin
  JNK c-Jun N-terminal kinase
  RPMI Roswell Park Memorial Institute medium. A medium for cell and tissue culture
  HWB Human whole blood
  DMEM Dulbecco's modified Eagle's medium. A vitamin and nutrient-enriched cell culture.
  FBS Fetal bovine serum
  RASF Rheumatoid arthritis synovial fibroblasts
General Procedure for Determining Pharmacokinetic Parameters Pharmacokinetic parameters of some examples were evaluated in male Sprague Dawley (SD) rats after intravenous (IV) and oral (PO) dosing. Male SD rats (5-6 weeks of age) were fasted for 12 hours before administration of the compound of interest. Animals were allowed access to food 2 h after dosing and water was given ad libitum. Except for the compound of Example 13, pharmacokinetic experiments comparing deuterium containing and non-deuterium containing compounds were performed at the same time using the same cohort of animals. The pharmacokinetic properties of the compound of Example 13 were evaluated separately and compared to previously generated data.

For IV dosing, a 0.5 mg/mL solution of the test compound was prepared in a vehicle consisting of 5% DMSO, 5% Cremophore, 90% normal saline. For a 1 mpk dose, 2 mL/kg of this dosing vehicle was administered to each rat by bolus injection into the tail vein. For lower doses, the dosing solution was diluted with the appropriate amount of vehicle. Example 3 was evaluated at 3 mpk by preparing a 1.5 mg/mL solution in the same vehicle and dosing 2 mL/kg. Blood samples from each animal was collected in di-sodium EDTA coated containers at 0.12, 0.25, 0.5, 1.0, 2.0, 4.0, 8.0 and 24.0 hours after dosing. Plasma was separated from the blood samples within 15 minutes following collection and stored at −20±5° C. before analysis.

For oral (PO) dosing, a 0.2 mg/mL suspension of the test compound was prepared in a vehicle comprising 0.5% Tween-20 in 0.5% methyl cellulose in phosphate buffered saline (PBS). For a 2 mpk dose, 10 mL/kg of this dosing vehicle was administered by oral gavage. Blood samples from each animal was collected di-sodium EDTA coated containers at 0.25, 0.5, 1.0, 2.0, 4.0, 8.0 10.0 and 24.0 hours after dosing. Plasma was separated from the blood samples within 15 minutes following collection and stored at −20±5° C. before analysis.

A standard curve was generated from a stock solution of the test compound with known concentration in methanol. Working solutions having known concentrations ranging from 5-20,000 ng/mL were prepared from the stock solution by dilution with methanol:water (80:20 v/v). 5 uL of the working solutions were added to 45 uL of blank rat plasma to provide standard samples for analysis.

Plasma samples collected from rats after dosing were allowed to reach room temperature. A 50 uL aliquot of each plasma sample and the standard curve plasma samples were treated with 200 uL of acetonitrile containing an internal standard (100 ng/mL; warfarin/diclofenac) and mixed well. The samples were vortexed for 5 minutes followed by centrifugation for 5 minutes at 14000 rpm at 4° C. The supernatant (10 uL) was analyzed by LC-MS/MS (LC: Shimadzu SIL HTc, MS: MDS Sciex API-5500 & 4000 using 75%/25% acetonitrile/0.2% formic acid in Milli-Q water, flow rate: 1.0 mL/min, run time 3 minutes, Atlantis dC18(50×4.6 mm, 3 um; Waters®)) and the concentrations of the test compound in the plasma samples collected from rats at each time point were determined by comparison to the standard curve samples.

Pharmacokinetic parameters were calculated from the plasma concentrations at each time point using Phoenix WinNonlin (Version 7.0) by the non-compartmental analysis (NCA) method. Clearance values are reported as mL/min/kg. AUC values are reported as ng·h/mL.

Graphs and statistical analyses were generated using GraphPad Prism (Version 8.1.0).

Example 17: IV Pharmacokinetics of Example 1 and Example 13 in Male SD Rats

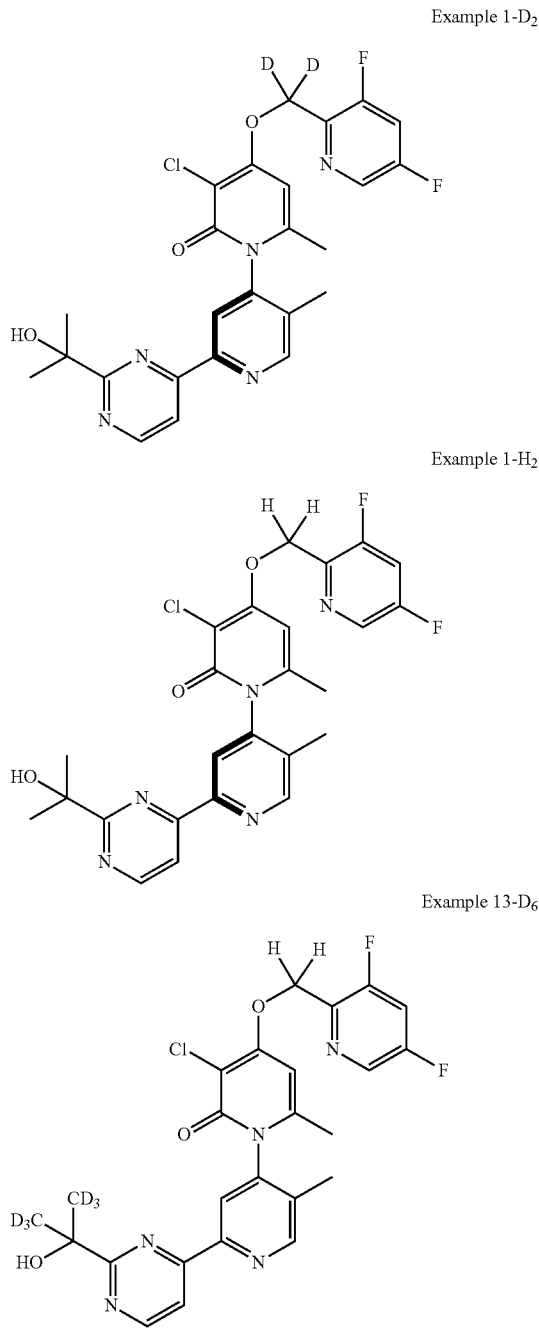

Example 1-D₂

Example 1-H₂

Example 13-D₆

IV pharmacokinetics of Example 1 were measured in male SD rats at 0.1, 0.3 and 1.0 mpk doses to evaluate the rate of clearance at each dose. As a comparator, (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one was evaluated. For clarity, this comparator is labeled in FIGS. 1-3 and Table 3 as Example 1-H₂ and (P)-3-chloro-4-((3,5-difluoropyridin-2-yl)methoxy-d₂)-2'-(2-(2-hydroxypropan-2-yl)pyrimidin-4-yl)-5',6-dimethyl-2H-[1,4'-bipyridin]-2-one is labeled as Example 1-D₂. Example 13 has deuterium incorporated at a different position than Example 1-D₂ and was evaluated at 1 mpk IV. For clarity, this is labeled as Example 13-D₆ in Table 3 and FIG. 3. Pharmacokinetic experiments comparing Example 1-H₂ and Example 1-D₂ were performed at the same time using the same cohort of animals. The pharmacokinetic properties of Example 13-D₆ was evaluated separately and compared to the data for Example 1-H₂.

TABLE 3

Calculated IV clearance for Example 1-D₂, Example 1-H₂ and Example 13-D₆ in male SD rats

| Example | IV clearance 0.1 mpk | IV clearance 0.3 mpk | IV clearance 1 mpk |
|---|---|---|---|
| Example 1-D₂ | 16 ± 4, P = 0.0265 | 12 ± 3, P = 0.0252 | 9.5 ± 1.4, P = 0.0015 |
| Example 1-H₂ | 24 ± 4 | 23 ± 7 | 24 ± 5 |
| Example 13-D₆ | ND | ND | 25 ± 7, P = 0.8071 |

Ranges in values represents one standard deviation. Two tailed P values were determined by comparison to Example 1-H₂ at the given dose using unpaired parametric t-test (GraphPad Prism Version 8.1.0).

Figure 2:
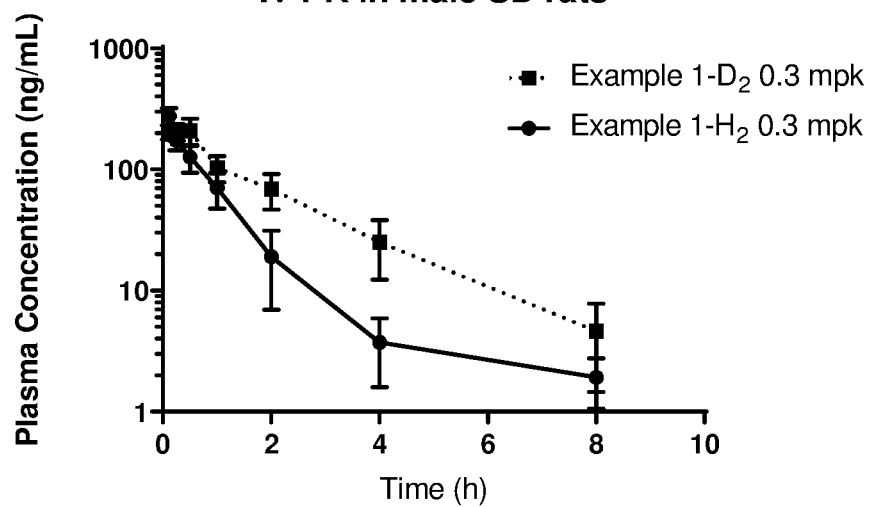
FIG. 2 shows the Plasma time-course data for Example 1-$D_2$ and Example 1-$H_2$ at 0.3 mpk IV.
Figure 3:
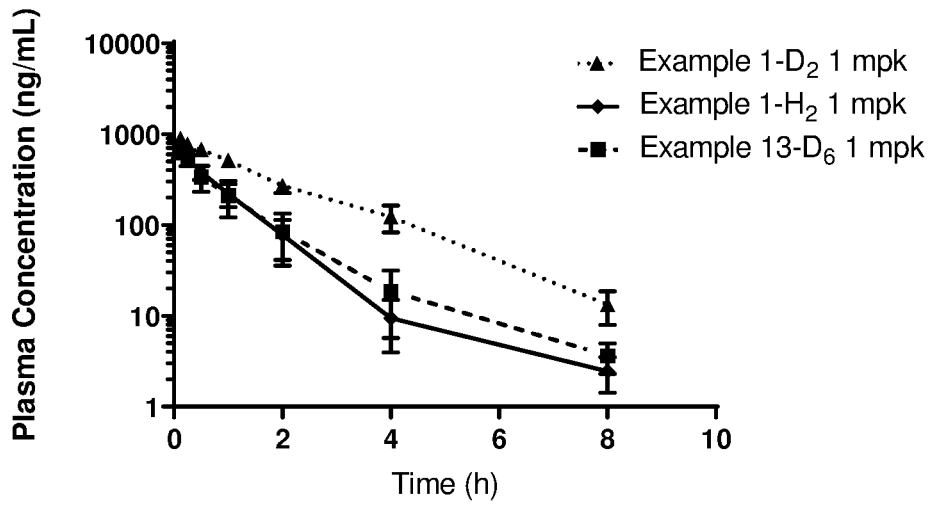
FIG. 3 shows the Plasma time-course data for Example 1-$D_2$, Example 1-$H_2$ and Example 13-$D_6$ at 1 mpk IV.

As can be seen from FIGS. 1-3 and Table 3, the deuterium substitution at position A in Formula (I) results in a statistically significant reduction in clearance for this particular R1 group at all 3 doses. Deuterium substitution at the B position in Formula (I) had no significant effect on clearance in the experiment.

Example 18: PO Pharmacokinetics of Example 1 in Male SD Rats

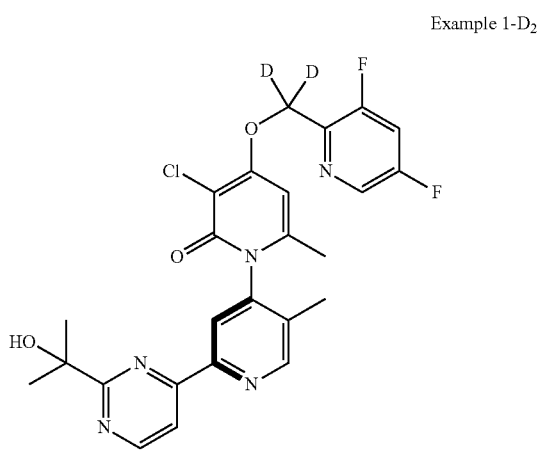

Example 1-D₂

Example 1-H₂

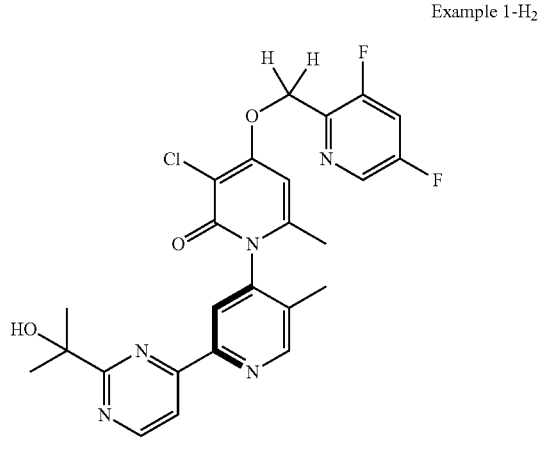

Figure 4:
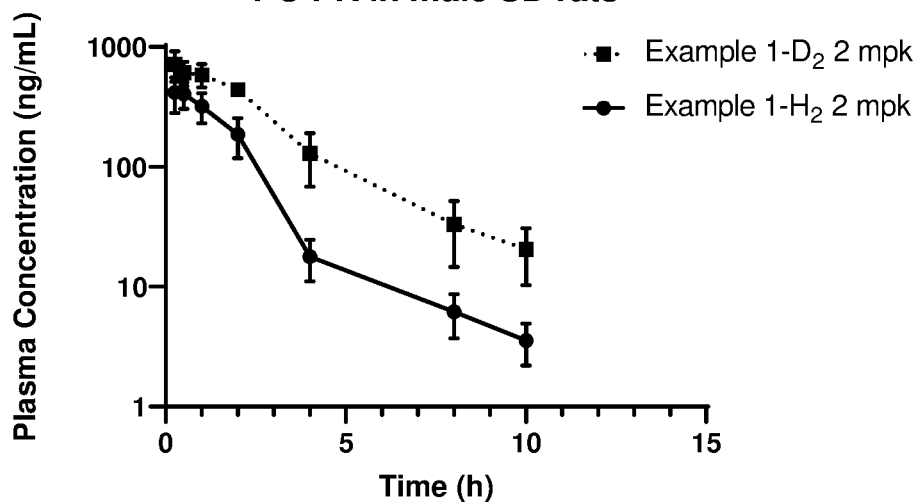
FIG. 4 shows the Plasma time-course data for Example 1-$D_2$ and Example 1-$H_2$ at 2 mpk orally (PO).

PO pharmacokinetics of Example 1 were measured in male SD rats at 2 mpk to evaluate the exposure at this dose. As a comparator, (P)-3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one was evaluated. For clarity, this comparator is labeled in FIG. 4 and Table 4 as Example 1-H₂ and (P)-3-chloro-4-((3,5-difluoropyridin-2-yl)methoxy-d₂)-2'-(2-(2-hydroxypropan-2-yl)pyrimidin-4-yl)-5',6-dimethyl-2H-[1,4'-bipyridin]-2-one is labeled as Example 1-D₂.

TABLE 4

Calculated PO AUC for Example
1-D₂ and Example 1-H₂ in male SD rats

| Example | AUC$_{0-10\ hr}$ |
|---|---|
| Example 1-D₂ | 2025 ± 120, P = 0.0005 |
| Example 1-H₂ | 854 ± 228 |

Ranges in values represents one standard deviation. Two tailed P values were determined by comparison to Example 1-H₂ at the given dose using unpaired parametric t-test (GraphPad Prism Version 8.1.0).

These data demonstrate the deuterium substitution at the A position results in significantly higher exposure of the compound of Example 1 after oral dosing.

Example 19: Determination of IV Pharmacokinetic Parameters of Example 3 in Male SD Rats Example 3-D₂

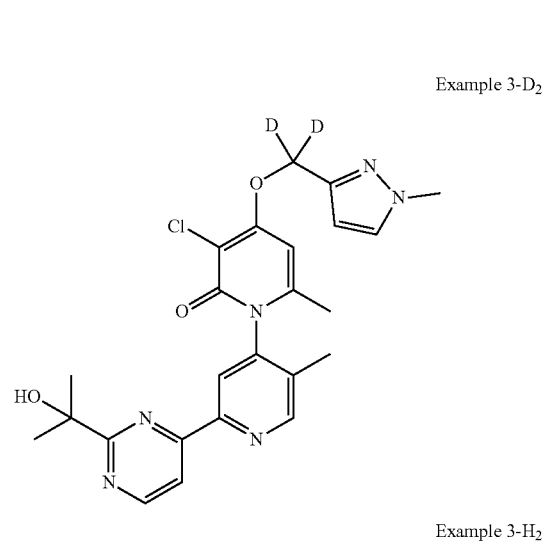

Example 3-H₂

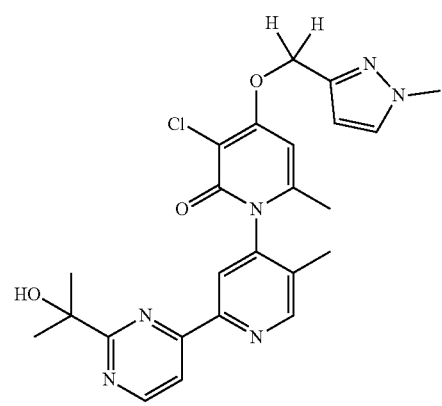

Figure 5:
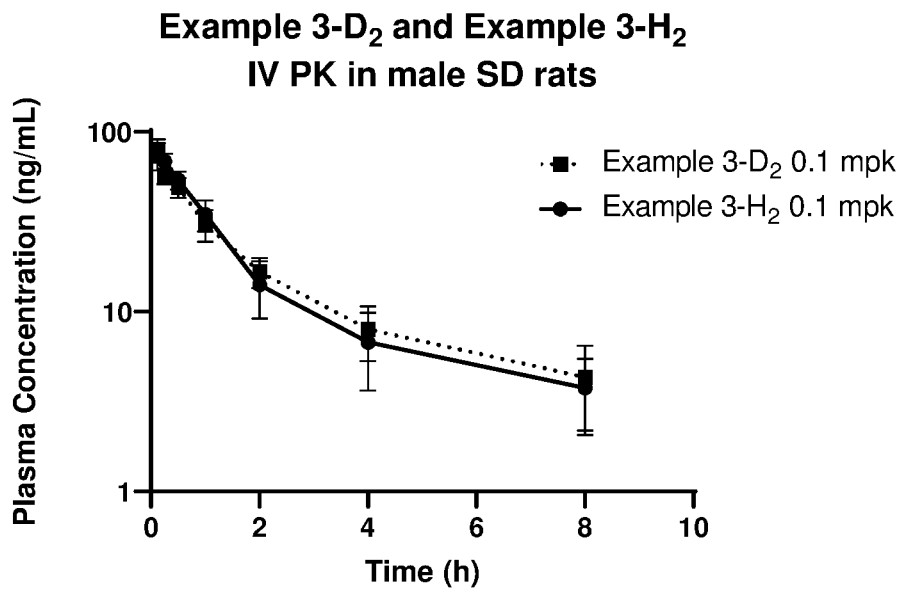
FIG. 5 shows the Plasma time-course data for Example 3-$D_2$ and Example 3-$H_2$ at 0.1 mpk IV.
Figure 6:
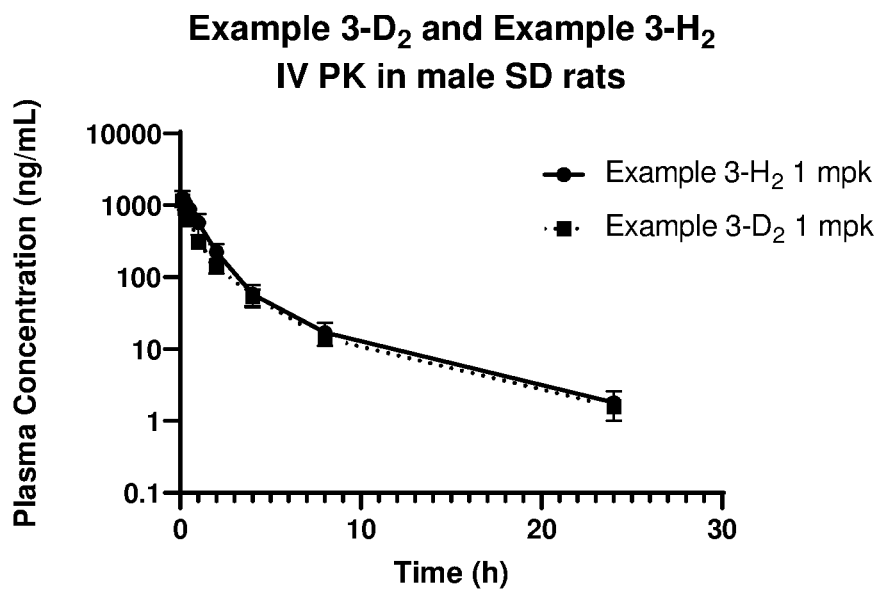
FIG. 6 shows the Plasma time-course data for Example 3-$D_2$ and Example 3-$H_2$ at 1 mpk IV.
Figure 7:
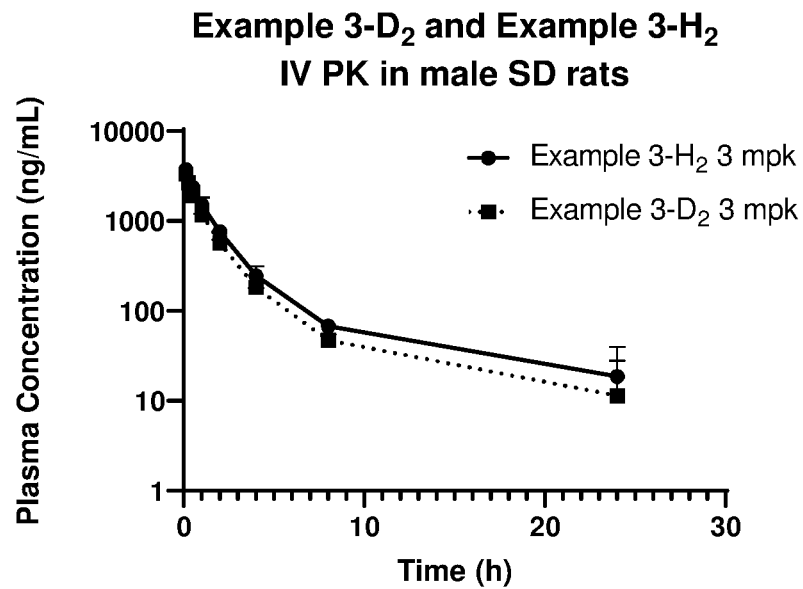
FIG. 7 shows the Plasma time-course data for Example 3-$D_2$ and Example 3-$H_2$ at 3 mpk IV.

IV pharmacokinetics of Example 3 was measured in male SD rats at 0.1, 1.0 and 3.0 mpk doses to evaluate the rate of clearance at each dose. As a comparator, 3-chloro-2'-(2-(2-hydroxypropan-2-yl)pyrimidin-4-yl)-5',6-dimethyl-4-((1-methyl-1H-pyrazol-3-yl)methoxy)-2H-[1,4'-bipyridin]-2-one was evaluated. For clarity, this comparator is labeled in FIGS. 5-7 and Table 4 as Example 3-H₂ and 3-chloro-2'-(2-(2-hydroxypropan-2-yl)pyrimidin-4-yl)-5',6-dimethyl-4-((1-methyl-1H-pyrazol-3-yl)methoxy-d₂)-2H-[1,4'-bipyridin]-2-one is labeled as Example 3-D₂.

TABLE 4

Calculated IV clearance for Example
3-D₂ and Example 3-H₂ in male SD rats

| Example | IV clearance 0.1 mpk | IV clearance 1 mpk | IV clearance 3 mpk |
|---|---|---|---|
| Example 3-D₂ | 12 ± 3, P = 0.762 | 13 ± 2, P = 0.06 | 9 ± 1, P = 0.300 |
| Example 3-H₂ | 13 ± 3 | 9 ± 2 | 8 ± 1 |

Ranges in values represents one standard deviation. Two tailed P values were determined by comparison to Example 3-H₂ at the given dose using unpaired parametric t-test (GraphPad Prism Version 8.1.0).

In this example, in contrast to the results obtained from Example 1, there is no statistically significant reduction in clearance at any of the IV doses examined.

Example 20: Determination of IV PK Parameters of Example 5 in Male SD Rats

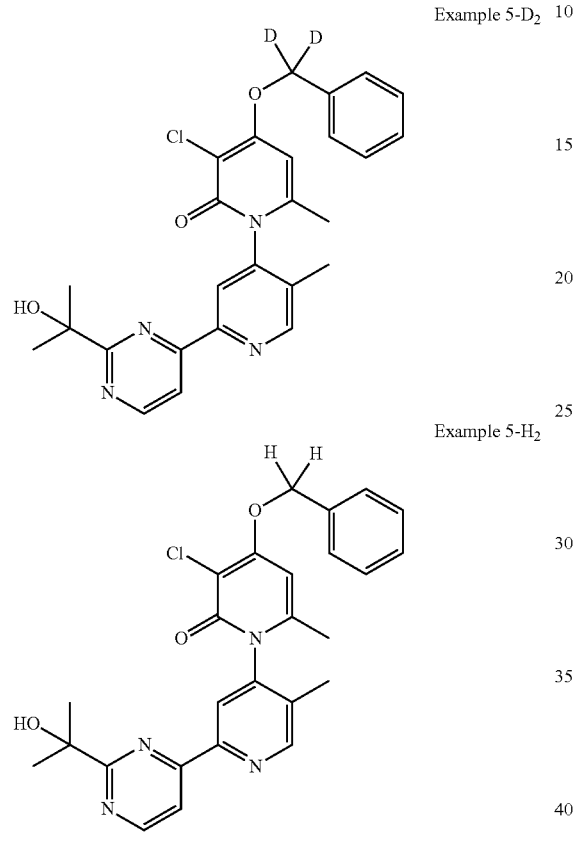

Example 5-D$_2$

Example 5-H$_2$

Figure 8:
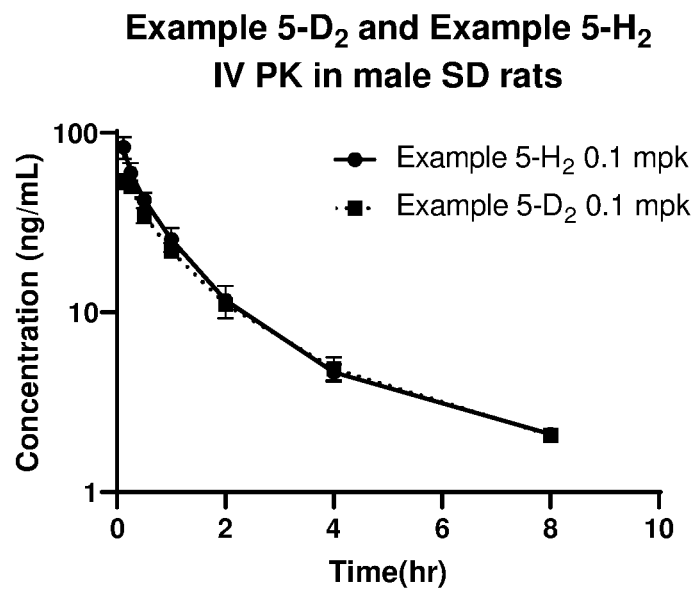
FIG. 8 shows the Plasma time-course data for Example 5-$D_2$ and Example 5-$H_2$ at 0.1 mpk IV.
Figure 9:
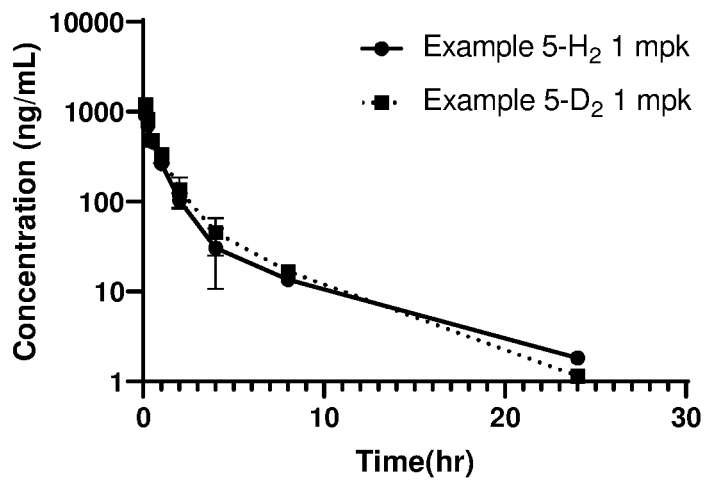
FIG. 9 shows the Plasma time-course data for Example 5-$D_2$ and Example 5-$H_2$ at 1 mpk IV.

IV pharmacokinetics of Example 5 was measured in male SD rats at 0.1 and 1.0 mpk doses to evaluate the rate of clearance at each dose. As a comparator, 3-chloro-2'-(2-(2-hydroxypropan-2-yl)pyrimidin-4-yl)-5',6-dimethyl-4-(phenylmethoxy)-2H-[1,4'-bipyridin]-2-one was evaluated. For clarity, this comparator is labeled in FIGS. 8 and 9 and Table 5 as Example 5-H$_2$ and 3-chloro-2'-(2-(2-hydroxypropan-2-yl)pyrimidin-4-yl)-5',6-dimethyl-4-(phenylmethoxy-d$_2$)-2H-[1,4'-bipyridin]-2-one is labeled as Example 5-D$_2$.

TABLE 5

Calculated IV clearance for Example 5-D$_2$ and Example 5-H$_2$ in male SD rats

| Example | IV clearance 0.1 mpk | IV clearance 1 mpk |
|---|---|---|
| Example 5-D$_2$ | 18 ± 1, P = 0.08 | 13 ± 2, P = 0.07 |
| Example 5-H$_2$ | 16 ± 2 | 15 ± 2 |

Ranges in values represents one standard deviation. Two tailed P values were determined by comparison to Example 5-H$_2$ at the given dose using unpaired parametric t-test (GraphPad Prism Version 8.1.0).

In this example, in contrast to the results obtained from Example 1, there is no statistically significant reduction in clearance at either of the IV doses examined.

Example 21: Determination of IV PK Parameters of Example 7 in Male SD Rats

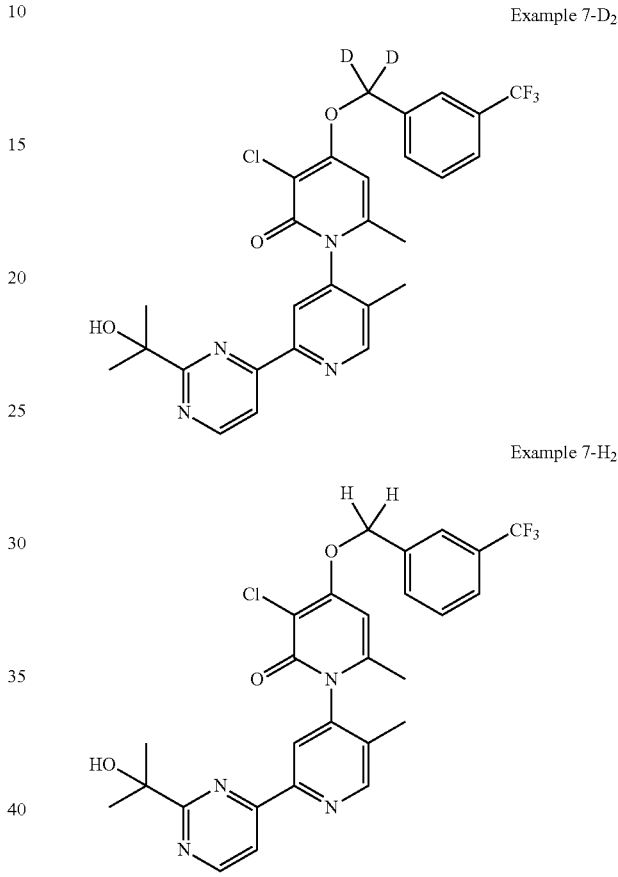

Example 7-D$_2$

Example 7-H$_2$

Figure 10:
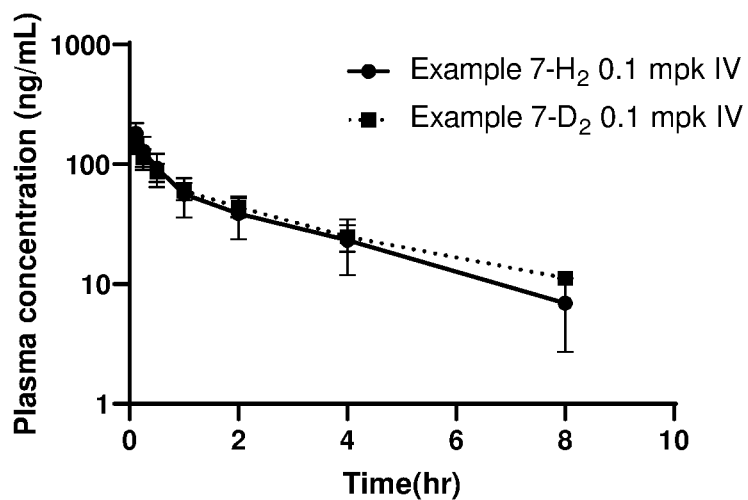
FIG. 10 shows the Plasma time-course data for Example 7-$D_2$ and Example 7-$H_2$ at 0.1 mpk IV.
Figure 11:
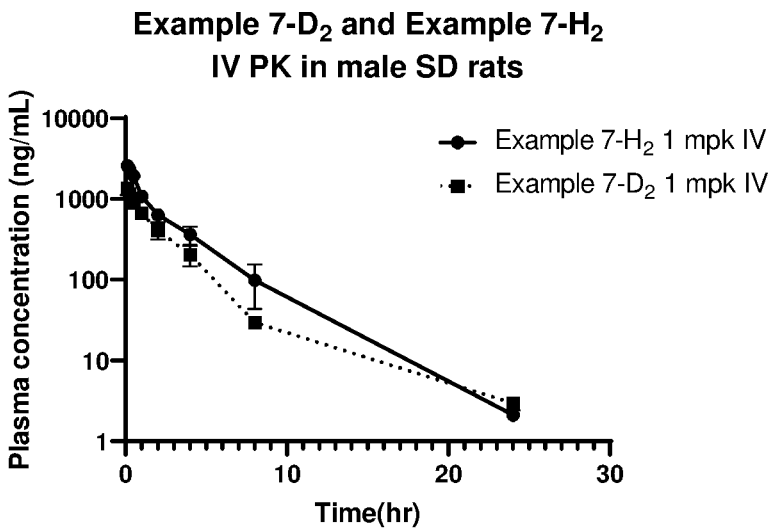
FIG. 11 shows the Plasma time-course data for Example 7-$D_2$ and Example 7-$H_2$ at 1 mpk IV.

IV pharmacokinetics of Example 7 was measured in male SD rats at 0.1 and 1.0 mpk doses to evaluate the rate of clearance at each dose. As a comparator, 3-chloro-2'-(2-(2-hydroxypropan-2-yl)pyrimidin-4-yl)-5',6-dimethyl-4-((3-(trifluoromethyl)phenyl)methoxy)-2H-[1,4'-bipyridin]-2-one was evaluated. For clarity, this comparator is labeled in FIGS. 10 and 11 and Table 6 as Example 7-H$_2$ and 3-chloro-2'-(2-(2-hydroxypropan-2-yl)pyrimidin-4-yl)-5',6-dimethyl-4-((3-(trifluoromethyl)phenyl)methoxy-d$_2$)-2H-[1,4'-bipyridin]-2-one is labeled as Example 7-D$_2$.

TABLE 6

Calculated IV clearance for Example 7-D$_2$ and Example 7-H$_2$ in male SD rats

| Example | IV clearance 0.1 mpk | IV clearance 1 mpk |
|---|---|---|
| Example 7-D$_2$ | 4.9 ± 0.5, P = 0.76 | 6 ± 1, P = 0.009 |
| Example 7-H$_2$ | 7 ± 4 | 3.1 ± 0.3 |

Ranges in values represents one standard deviation. Two tailed P values were determined by comparison to Example 7-H$_2$ at the given dose using unpaired parametric t-test (GraphPad Prism Version 8.1.0).

In this example, in contrast to the results obtained from Examples 1, 3 and 5, there is no statistically significant reduction in clearance at the 0.1 mpk dose, perhaps owing to the higher variability within the 0.1 mpk dose group with Example 1-H$_2$, but the deuterated material has a significantly higher clearance at 1.0 mpk. In both cases, there is no clear improvement in clearance in deuterium substitution for this example.

Example 22: Determination of IV PK Parameters of Example 9 in Male SD Rats

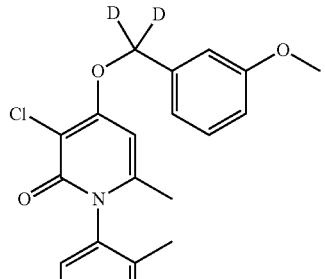

Example 9-D$_2$

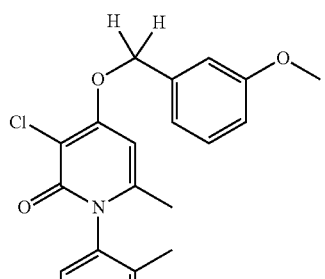

Example 9-H$_2$

Figure 12:
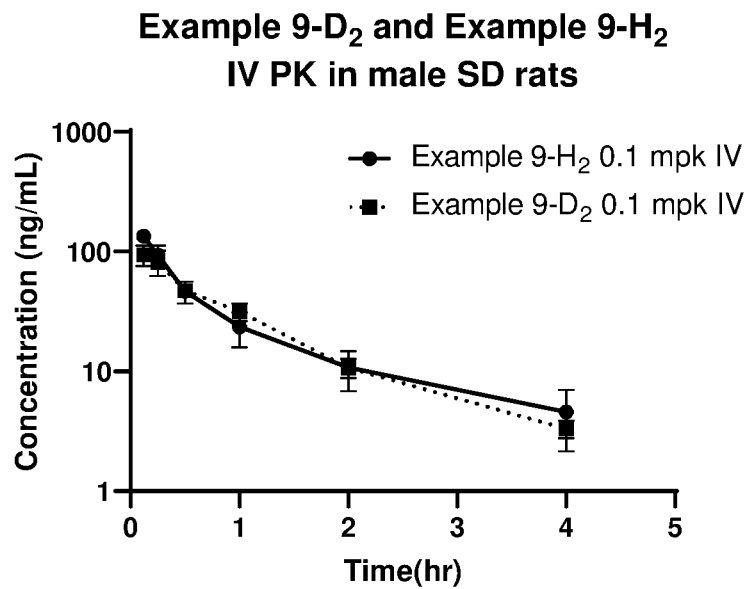
FIG. 12 shows the Plasma time-course data for Example 9-$D_2$ and Example 9-$H_2$ at 0.1 mpk IV.
Figure 13:
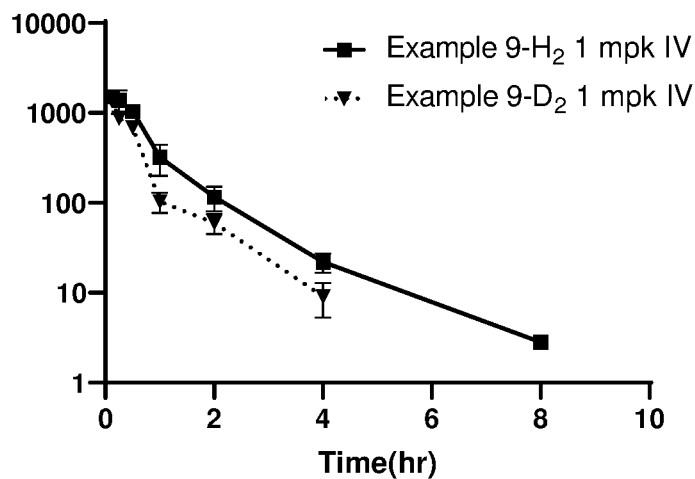
FIG. 13 shows the Plasma time-course data for Example 9-$D_2$ and Example 9-$H_2$ at 1 mpk IV.

IV pharmacokinetics of Example 9 was measured in male SD rats at 0.1 and 1.0 mpk doses to evaluate the rate of clearance at each dose. As a comparator 3-chloro-2'-(2-(2-hydroxypropan-2-yl)pyrimidin-4-yl)-4-((3-methoxyphenyl)methoxy)-5',6-dimethyl-2H-[1,4'-bipyridin]-2-one was evaluated. For clarity, this comparator is labeled in FIGS. 12 and 13 and Table 7 as Example 9-H$_2$ and 3-chloro-2'-(2-(2-hydroxypropan-2-yl)pyrimidin-4-yl)-4-((3-methoxyphenyl)methoxy-d$_2$)-5',6-dimethyl-2H-[1,4'-bipyridin]-2-one is labeled as Example 9-D$_2$.

TABLE 7

Calculated IV clearance for Example 9-D$_2$ and Example 9-H$_2$ in male SD rats

| Example | IV clearance 0.1 mpk | IV clearance 1 mpk |
|---|---|---|
| Example 9-D$_2$ | 17 ± 3, P = 0.49 | 18 ± 2, P = 0.0025 |
| Example 9-H$_2$ | 16 ± 3 | 12 ± 2 |

Ranges in values represents one standard deviation. Two tailed P values were determined by comparison to Example 9-H$_2$ at the given dose using unpaired parametric t-test (GraphPad Prism Version 8.1.0)

In this example there is no difference in clearance with deuterium substitution at the 0.1 mpk dose and a more rapid clearance of the deuterated material at the 1 mpk dose.

Example 23: Determination of IV PK Parameters of Example 11 in Male SD Rats

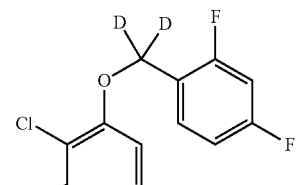

Example 11-D$_2$

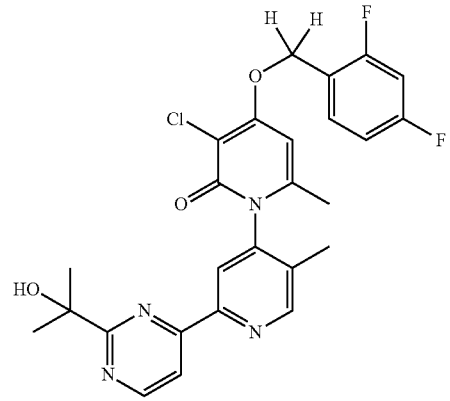

Example 11-H$_2$

Figure 14:
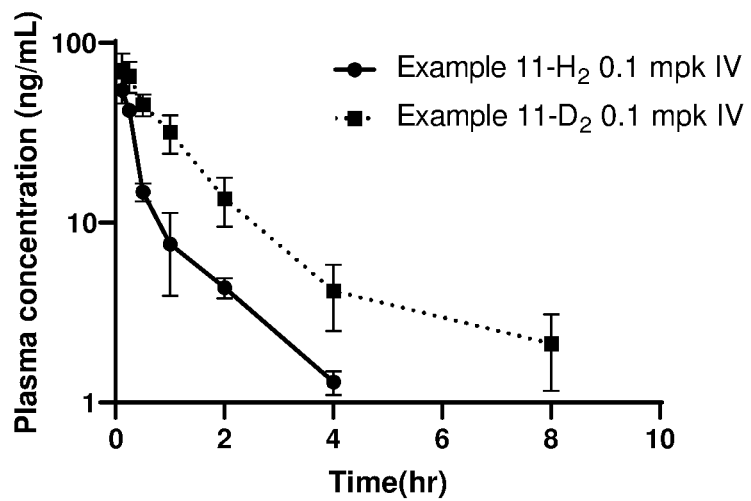
FIG. 14 shows the Plasma time-course data for Example 11-$D_2$ and Example 11-$H_2$ at 0.1 mpk IV.
Figure 15:
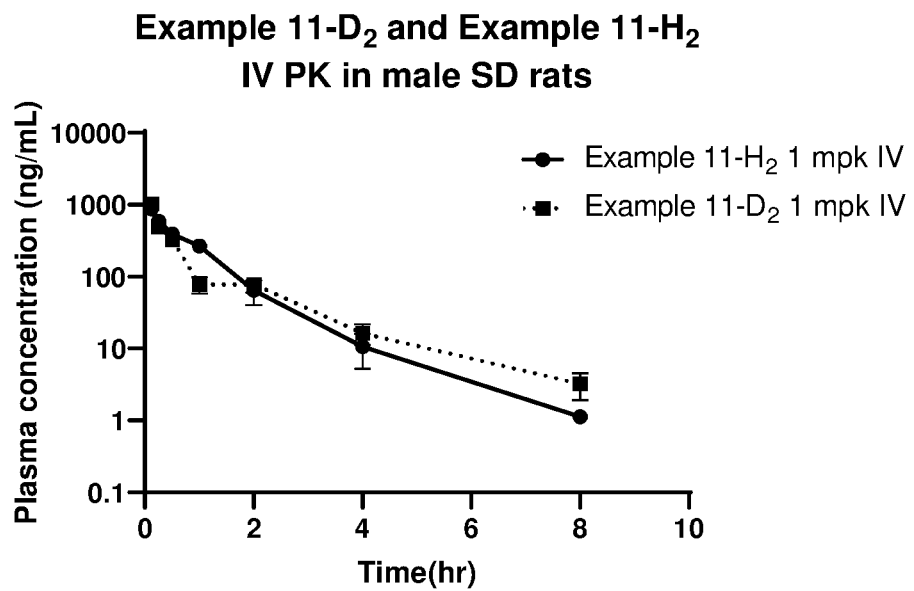
FIG. 15 shows the Plasma time-course data for Example 11-$D_2$ and Example 11-$H_2$ at 1 mpk IV.

IV pharmacokinetics of Example 11 was measured in male SD rats at 0.1 and 1.0 mpk doses to evaluate the rate of clearance at each dose. As a comparator, 3-chloro-4-((2,4-difluorophenyl)methoxy-d$_2$)-2'-(2-(2-hydroxypropan-2-yl)pyrimidin-4-yl)-5',6-dimethyl-2H-[1,4'-bipyridin]-2-one was evaluated. For clarity, this comparator is labeled in FIGS. 13 and 14 and Table 8 as Example 11-H$_2$ and 3-chloro-4-((2,4-difluorophenyl)methoxy-d$_2$)-2'-(2-(2-hydroxypropan-2-yl)pyrimidin-4-yl)-5',6-dimethyl-2H-[1,4'-bipyridin]-2-one is labeled as Example 11-$D_2$.

TABLE 8

Calculated IV clearance for Example 9-$D_2$ and Example 9-$H_2$ in male SD rats

| Example | IV clearance 0.1 mpk | IV clearance 1 mpk |
|---|---|---|
| Example 11-$D_2$ | 16 ± 5, P = 0.0008 | 25 ± 3, P = 0.052 |
| Example 11-$H_2$ | 40 ± 4 | 22 ± 2 |

Ranges in values represents one standard deviation. Two tailed P values were determined by comparison to Example 11-$H_2$ at the given dose using unpaired parametric t-test (GraphPad Prism Version 8.1.0).

In this example deuterium replacement results in a clear reduction in clearance at the 0.1 mpk dose but not a statistically significant reduction at 1 mpk. The clearance of Example 11-$H_2$ shows a strong dose dependence suggesting the saturation or inhibition of clearance at higher IV doses, while Example 11-$D_2$ behaves differently.

The data from the preceding examples demonstrate that within this chemical series, deuterium substitution at the A position of Formula (I) can have differing results depending on the selection of $R_1$ group. In some cases, there is no clear improvement in clearance, in some cases there are non-linear pharmacokinetics and in some cases deuterium substitution results in higher clearance. In one case, i.e., the compound of Example 1, there is a clear and consistent reduction in clearance with deuterium substitution at position A across doses. Example 1 also showed increased exposure after PO dosing as measured by AUC. Deuterium substitution at position B, however, did not result in a statistically significant reduction in clearance as shown by comparison to Example 13.

Example 24: p38 Inhibitory Potency and p38/MK2 Substrate Selectivity

This study evaluated the potency of the compounds described herein in inhibiting the p38 pathway. p38 activates MK2 and PRAK via phosphorylation, which both then interact with Hsp27, leading to increased inflammation and decreased ability to manage shock. The study measured the amount of the inventive compound necessary to inhibit activation of MK2 and PRAK by half. This is a measurement of how effective the inventive compound is in helping to lower inflammatory response, which helps treat many diseases, including autoimmune conditions, lymphoma, and rheumatoid arthritis. The novel, MK2 substrate-selective inhibitory mechanism of compounds is evaluated in enzyme assays comparing inhibitor potency in blocking p38/MK2 versus p38/PRAK induced phosphorylation of an HSP-27 derived peptide substrate. The ability of compounds to inhibit activated phospho-p38α is evaluated using a p38α/MK2 and a p38α/PRAK cascade assay format. The kinase activity of p38α is determined by its ability to phosphorylate GST-MK2 or GST-PRAK. Activation of MK2 or PRAK by p38α is quantitated by measuring the phosphorylation of a fluorescently-labeled, MK2/PRAK specific peptide substrate, Hsp27 peptide (FITC-KKKALSRQLSVAA, American Peptide catalog number 222 310945, Sunnyvale, CA). The phosphorylation of the Hsp27 peptide is quantified using IMAP technology (Molecular Devices, Sunnyvale CA). Kinase reactions are carried out in a 384-well plate (Greiner, 781280) in 20 mM HEPES pH 7.5, 10 mM MgCl2, 0.01% Triton X-100, 0.01% BSA, 1 mM DTT, and 2% DMSO. The inhibitor concentration is varied between 0.02-30,000 nM, while the Hsp27 peptide substrate and MgATP are held constant at 1 µM and 10 µM, respectively. Activated p38α is added to a final concentration of 30 pM for reactions with nonphosphorylated 1 nM GST-MK2 in the cascade reaction. For the p38α/PRAK cascade, unactivated GST-PRAK is held constant at 10 nM while p38α is added in to a final concentration of 200 pM. Kinase reactions are incubated at room temperature and quenched after 120 minutes by the addition of IMAP Binding Solution. Under these conditions, approximately 20% of the substrate Hsp27 peptide is phosphorylated. Reactions are initiated by the addition of activated p38α except for preincubation experiments, where reactions are initiated by the addition of Hsp27 peptide and MgATP. Preincubation of p38α with inhibitor or p38α with unactivated GST-MK2 or unactivated GST-PRAK and inhibitor are performed at 2× final assay concentrations at room temperature 240 minutes prior to adding ATP and Hsp27 peptide to initiate catalysis. The p38α compound inhibitory potency is quantitated from dose-response $IC_{50}$ values or Ki values from p38α/MK2 cascade assays while the substrate selectivity is calculated as a ratio of p38α/PRAK:p38α/MK2 $IC_{50}$ values. Species compounds of Formula (I), described hereinabove, evaluated in this assay, are expected to provide a therapeutic benefit in the treatment of p38 MAP Kinase mediated diseases, such as autoimmune diseases and lymphoma.

Example 1-$D_2$ and Example 1-$H_2$, as described in Example 17, were tested in accordance with the above described assay, yielding $IC_{50}$ values described in Table 9.

TABLE 9

| Example Number | p38/MK2 cascade-Caliper ($IC_{50}$) +++ indicates ≤0.01 µM ++ indicates 0.01-0.1 µM + indicates 0.1-1 µM − indicates >1 µM | p38/PRAK cascade-Caliper ($IC_{50}$) +++ indicates ≤0.01 µM ++ indicates 0.01-0.1 µM + indicates 0.1-1 µM − indicates >1 µM | PRAK/MK2 ratio |
|---|---|---|---|
| 1-$H_2$ | +++ | − | >400 |
| 1-$D_2$ | +++ | − | >400 |

Example 25: Determination of the In Vitro Metabolite Profile of Example 1 in Hepatocytes This study evaluated and compared the in vitro metabolite profile of Example 1-$D_2$ and Example 1-$H_2$, as described in Example 17, in cryopreserved hepatocytes from rat (SHQY; Catalog #BQR1000.H15), dog (SHQY; Catalog #BQD1000.H15), minipig (BIOIVT; Catalog #M00615), monkey (XENOTECH; Catalog #P2000H15), and human (SHQY; Catalog #BQHPCH10). Briefly, each test compound (final concentration of 10 µM containing 0.1% DMSO) was incubated with rat, dog, minipig, monkey, or human hepatocytes (final viable cell density of 1×10⁶ cells/mL) at 37° C. with 5% $CO_2$ in HI hepatocyte maintenance media (BIOIVT; Catalog #Z99009) for 120 minutes. Reactions were initiated by combining 200 μL of pre-warmed 2× dosing solution containing 20 μM test compound and 0.2% DMSO in HI maintenance media with 200 μL of pre-warmed hepatocyte solution containing 2×10$^6$ cells/mL in HI maintenance media. Samples were taken at 0 minutes ($T_0$) and 120 minutes ($T_{120}$) by quenching the reaction with 1200 μL acetonitrile. After quenching, the samples were sonicated for 2 minutes and then centrifuged at 1400 rpm for 5 minutes. A 1400-μL aliquot of the supernatant was evaporated under a stream of $N_2$ until dry. The dried extracts were then reconstituted with 200 μL acetonitrile: $H_2O$ (1:3 v/v), vortexed for 2 minutes and centrifuged at 14000 rpm for 5 minutes. A 2-μL aliquot of the supernatant was injected onto a Xevo UPLC-UV-G2-S Q-Tof system (Waters®) with positive-ion electrospray ionization for analysis. Chromatographic separation was achieved on an Acquity age of the O-dealkylation product M387 formed for Example 1-$D_2$ relative to Example 1-$H_2$. In contrast, there were no obvious quantitative differences between the deuterated and non-deuterated forms of the 4 hydroxylation products.

In this example deuterium replacement did not result in the introduction of any novel metabolites following incubation in hepatocytes from different species, but there was an apparent attenuation in both the loss of parent compound and the formation of M387, which is the product of oxidative 0-dealkylation at the benzylic carbon of the 3,5-difluoropyridin-2-yl)methoxy moiety (i.e., the site of deuteration). The results obtained for Example 1-$D_2$ relative to Example 1-$H_2$ are consistent with a deuterium kinetic isotope effect for the deuterated form.

TABLE 10

Major metabolites of Example 1-$D_2$ and Example 1-$H_2$ after incubation in hepatocytes from rat, dog, minipig, monkey, and human

| Test Article | Analyte | Found m/z | Mass Shift | Biotransformation | R.T. (min) | UV % at 280-290 nm or observed (+ or --) * | | | | |
|---|---|---|---|---|---|---|---|---|---|---|
| | | | | | | Rat | Dog | Minipig | Monkey | Human |
| Example 1-$D_2$ | Parent-$T_{0\ min}$ | 516.1583 | 0 | n/a | 4.99 | 100.0% | 100.0% | 100.0% | 100.0% | 100.0% |
| | Parent-$T_{120\ min}$ | 516.1583 | 0 | n/a | 4.99 | 84.3% | 96.0% | 81.1% | 96.6% | 88.2% |
| | $M_{387}$ | 387.1230 | −129.0353 | O-dealkylation | 4.23 | 4.1% | + | 1.7% | + | + |
| | $M_{532b}$ | 532.1525 | 15.9942 | Hydroxylation | 4.57 | -- | -- | + | -- | + |
| | $M_{532c}$ | 532.1525 | 15.9942 | Hydroxylation | 4.65 | 1.2% | + | + | + | 1.2% |
| | $M_{532d}$ | 532.1525 | 15.9942 | Hydroxylation | 4.72 | -- | -- | 1.6% | + | 1.4% |
| | $M_{532e}$ | 532.1525 | 15.9942 | Hydroxylation | 4.84 | + | + | 2.8% | 1.3% | + |
| Example 1-$H_2$ | Parent-$T_{0\ min}$ | 514.1457 | 0 | n/a | 4.99 | 100.0% | 100.0% | 100.0% | 100.0% | 100.0% |
| | Parent-$T_{120\ min}$ | 514.1457 | 0 | n/a | 4.99 | 82.7% | 87.0% | 70.0% | 85.7% | 84.8% |
| | $M_{563}$ | 563.1544 | 49.0087 | O-dealkylation + Glucuronidation | 3.80 | 1.06% | + | + | + | -- |
| | $M_{387}$ | 387.1230 | −127.0227 | O-dealkylation | 4.23 | 16.2% | 4.1% | 14.4% | 4.8% | 3.5% |
| | $M_{530b}$ | 530.1392 | 15.9935 | Hydroxylation | 4.57 | + | -- | -- | -- | + |
| | $M_{530c}$ | 530.1392 | 15.9935 | Hydroxylation | 4.65 | 1.1% | + | + | + | 1.3% |
| | $M_{530d}$ | 530.1392 | 15.9935 | Hydroxylation | 4.72 | -- | -- | 1.6% | -- | 1.5% |
| | $M_{530e}$ | 530.1392 | 15.9935 | Hydroxylation | 4.84 | + | + | 2.4% | 1.5% | + |

* All percentages were calculated based on the detected UV absorption relative to that of parent in T0 min samples (normalized as 100%)
--: not detected or trace
+: only detected by MS
n/a: not applicable UPLC®BEH $C_{18}$ column (2.1×50 mm, 1.7 μm; Waters®) by gradient elution using varying proportions of mobile phase A ($H_2O$ with 0.1% formic acid) and mobile phase B (acetonitrile with 0.1% formic acid) at a constant flow rate of 400 μL/minute over a total run time of 10 minutes. LC-UV-MS extract ion chromatograms (EIC) of the $T_{120}$ samples were compared to the $T_0$ samples to identify the major putative metabolites which were named as $M_{m/z}$.

Figure 16:
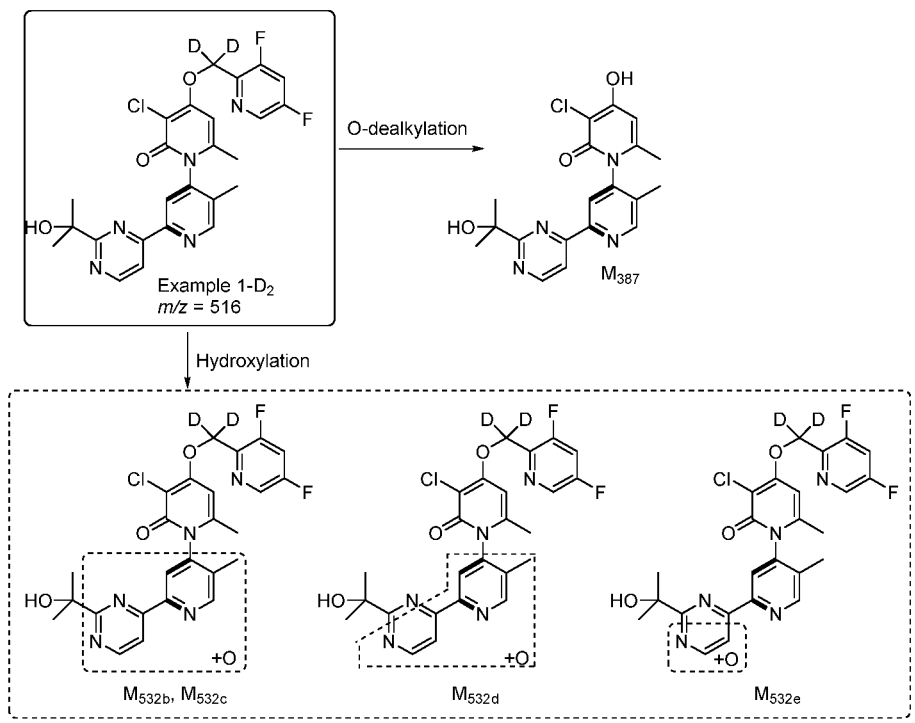
FIG. 16 shows the proposed metabolic pathways for Example 1-$D_2$ in rat, dog, minipig, monkey, and human hepatocytes.
Figure 17:
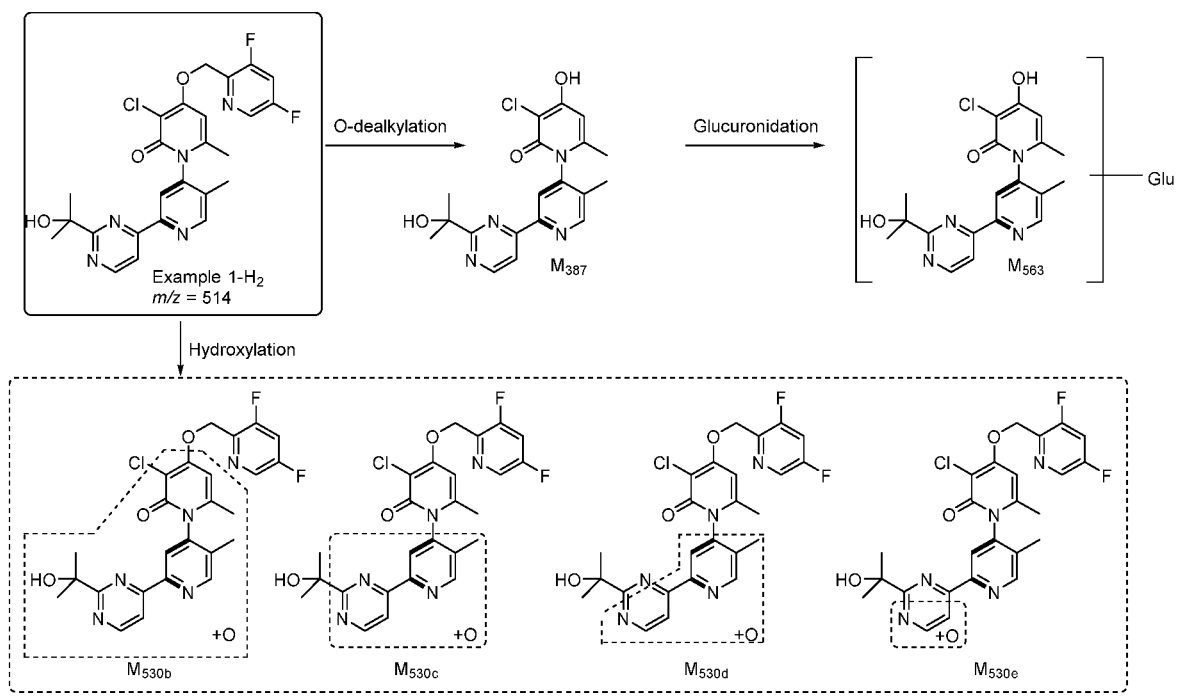
FIG. 17 shows the proposed metabolic pathways for Example 1-$H_2$ in rat, dog, minipig, monkey, and human hepatocytes.

As shown in Table 10 and FIG. 16, Example 1-$D_2$ was transformed into a total of 5 metabolites which included an O-dealkylation product (M387) and 4 hydroxylation products (M532b, M532c, M532d, and M532e). Metabolites representing these same 5 biotransformations were also observed for Example 1-$H_2$, namely M387, M530b, M530c, M530d, and M530e, plus a product of O-dealkylation and glucuronidation (M563) (Table 10 and FIG. 17). Hence, each metabolite of Example 1-$D_2$ was represented after incubation of hepatocytes with Example 1-$H_2$. Apparent quantitative differences were, however, observed between Example 1-$D_2$ and Example 1-$H_2$ in hepatocytes. Specifically, a comparison of the percentages of parent compound and of each metabolite at the end of the 120-minute incubation showed that there was a consistently larger percentage of parent remaining and a consistently smaller percent-

The invention claimed is:

1. A compound having the structure:

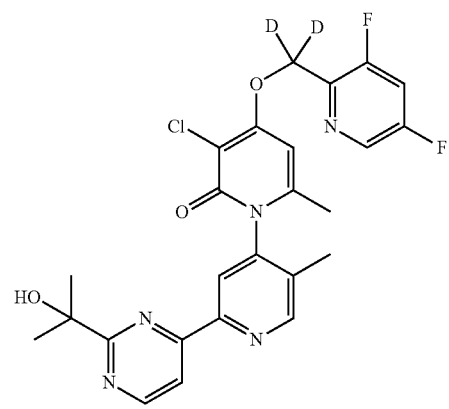 [SMILES: [2H]C([2H])(Oc1cc(C)n(-c2cc(-c3ccnc(C(C)(C)O)n3)ncc2C)c(=O)c1Cl)c1ncc(F)cc1F]

3-Chloro-4-((3,5-difluoropyridin-2-yl)methoxy-$d_2$)-2'-(2-(2-hydroxypropan-2-yl)pyrimidin-4-yl)-5',6-dimethyl-2H-[1,4'-bipyridin]-2-one, or a pharmaceutically acceptable salt thereof, wherein 3-Chloro-4-((3,5-difluoropyridin-2-yl) methoxy-d$_2$)-2'-(2-(2-hydroxypropan-2-yl)pyrimidin-4-yl)-5',6-dimethyl-2H-[1,4'-bipyridin]-2-one, or a pharmaceutically acceptable salt thereof, is a single atropisomer and wherein the single atropisomer is (P)-3-Chloro-4-((3,5-difluoropyridin-2-yl) methoxy-d$_2$)-2'-(2-(2-hydroxypropan-2-yl)pyrimidin-4-yl)-5',6-dimethyl-2H-[1,4'-bipyridin]-2-one, or a pharmaceutically acceptable salt thereof.

2. A composition comprising the compound of claim 1, wherein the isotopic enrichment at each position labeled in the structure is equal to or greater than 70%.

3. The composition of claim 2, wherein the isotopic enrichment at each position labeled in the structure is equal to or greater than 80%.

4. The composition of claim 2, wherein the isotopic enrichment at each position labeled in the structure is equal to or greater than 90%.

5. The composition of claim 2, wherein the isotopic enrichment at each position labeled in the structure is equal to or greater than 95%.

6. The composition of claim 2, wherein the isotopic enrichment at each position labeled in the structure is equal to or greater than 99%.

7. A pharmaceutical composition comprising a therapeutically effective amount of a compound of claim 1, a pharmaceutically acceptable salt thereof, or a combination thereof; and a pharmaceutically acceptable excipient.

* * * * *